US006924276B2

(12) United States Patent
Sorenson

(10) Patent No.: US 6,924,276 B2
(45) Date of Patent: Aug. 2, 2005

(54) DIACID-SUBSTITUTED HETEROARYL DERIVATIVES AS MATRIX METALLOPROTEINASE INHIBITORS

(75) Inventor: Roderick Joseph Sorenson, Ann Arbor, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 141 days.

(21) Appl. No.: 10/224,234

(22) Filed: Aug. 20, 2002

(65) Prior Publication Data

US 2003/0087924 A1 May 8, 2003

Related U.S. Application Data

(60) Provisional application No. 60/318,488, filed on Sep. 10, 2001.

(51) Int. Cl.[7] ................ A61K 31/33; C07D 331/00; C07D 333/00; C07D 317/00

(52) U.S. Cl. ................ 514/183; 514/438; 549/1; 549/29; 549/64; 549/66; 549/200; 549/434; 549/430

(58) Field of Search .................... 514/183, 438; 549/1, 29, 64, 66, 200, 434, 430

(56) References Cited

U.S. PATENT DOCUMENTS

| | | | |
|---|---|---|---|
| 3,127,416 A | 3/1964 | Liechti et al. ........... 260/332.2 |
| 3,255,199 A | 6/1966 | Maeder et al. ................. 523/64 |
| 3,925,460 A | 12/1975 | Henrick et al. ......... 260/468 H |
| 3,928,413 A | 12/1975 | Henrick et al. ......... 260/476 R |
| 3,932,436 A | 1/1976 | Grohe et al. |
| 4,010,174 A | 3/1977 | Grohe et al. |
| 4,093,622 A | 6/1978 | Henrick et al. ......... 260/295 R |
| 5,130,317 A | 7/1992 | Baader et al. |
| 5,260,323 A | 11/1993 | Baader et al. |
| 5,519,038 A | 5/1996 | Baader et al. |
| 5,948,780 A * | 9/1999 | Peterson et al. ........ 514/255.01 |
| 6,008,243 A | 12/1999 | Bender et al. |
| 6,232,338 B1 | 5/2001 | Davies et al. |
| 6,380,214 B1 | 4/2002 | Gant et al. .................. 514/314 |
| 2002/0151555 A1 | 10/2002 | Barvian et al. |
| 2002/0151558 A1 | 10/2002 | Andrianiara et al. |
| 2002/0156061 A1 | 10/2002 | Barvian et al. |
| 2002/0156069 A1 | 10/2002 | Picard et al. |
| 2002/0161000 A1 | 10/2002 | Barvian et al. |
| 2002/0193377 A1 | 12/2002 | Andrianiara et al. |
| 2003/0004172 A1 | 1/2003 | Harter et al. |
| 2003/0130278 A1 | 7/2003 | Gaudilliere et al. |
| 2003/0229103 A1 | 12/2003 | Weithmann et al. |

FOREIGN PATENT DOCUMENTS

| | | |
|---|---|---|
| CH | 437347 | 11/1967 |
| EP | 0359454 | 3/1990 |
| EP | 0387725 | 9/1990 |
| EP | 0418797 B1 | 8/1994 |
| EP | 0463592 B1 | 8/1994 |
| EP | 0935963 | 8/1999 |
| EP | 1138680 | 10/2001 |
| JP | 05303181 * | 11/1993 |
| JP | 8269008 | 10/1998 |
| NL | 6513852 | 4/1966 |
| WO | 9408577 * | 4/1994 |
| WO | 9610617 | 4/1996 |
| WO | 9706138 | 2/1997 |
| WO | 9730975 | 8/1997 |
| WO | 9852558 | 11/1998 |
| WO | WO 00/00486 | 1/2000 |
| WO | WO 00/09485 | 2/2000 |
| WO | 0030683 | 6/2000 |
| WO | 0053573 | 9/2000 |
| WO | WO 01/12611 | 2/2001 |
| WO | WO 01/62750 A1 | 8/2001 |
| WO | WO 01/63244 | 8/2001 |
| WO | WO 02/34726 | 5/2002 |
| WO | WO 02/34753 | 5/2002 |
| WO | WO 02/064547 | 8/2002 |
| WO | WO 02/064568 | 8/2002 |
| WO | WO 02/064571 | 8/2002 |
| WO | WO 02/064572 | 8/2002 |
| WO | WO 02/064578 | 8/2002 |
| WO | WO 02/064595 | 8/2002 |
| WO | WO 02/064598 | 8/2002 |
| WO | WO 02/064599 | 8/2002 |
| WO | WO 03/032999 | 4/2003 |
| WO | WO 03/033478 | 4/2003 |
| WO | WO 03/049738 A1 | 6/2003 |

OTHER PUBLICATIONS

Chemical Abstract DN 106:83869, also cited as Khimiya Get.Soed.,6,826–36(1986).*
Skotnicki et al, PubMed Abstract 14579524, also cited as Curr.Opin.Drug Discov. Devel. 6/5, 742–59(2003).*
Trifilieff et al, PubMed Abstract 11934805, also cited as Br. J. Pharmacol. 135/7, 1655–64(2002).*
Cecil Textbook of Medicine, 2oth Edition, vol. 1, pp. 1004–1010(1996).*
Uckun et al, Current Cancer Drug Targets, 1, 59–71(2001).*
Nozaki et al, PubMed Abstract 14524529, also cited as Clin Exp. Metastasis,20/5,407–12(2003).*

(Continued)

Primary Examiner—Richard L. Raymond
Assistant Examiner—Sudhaker B. Patel
(74) Attorney, Agent, or Firm—Pfizer Inc.; Claude F. Purchase, Jr.

(57) ABSTRACT

The invention provides dicarboxylic acid-substituted heteroaryl derivatives of the formula

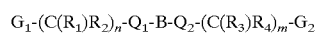

$$G_1\text{-}(C(R_1)R_2)_n\text{-}Q_1\text{-}B\text{-}Q_2\text{-}(C(R_3)R_4)_m\text{-}G_2 \qquad I$$

or a pharmaceutically acceptable salt thereof, wherein $G_1$, $G_2$, $R_1$, $R_2$, $R_3$, $R_4$, n, m, $Q_1$, $Q_2$, and B are as defined in the specification. The invention compounds are inhibitors of matrix metalloproteinase enzymes, including MMP-13. This invention also provides pharmaceutical compositions and methods of treating diseases mediated by MMP-13, including arthritis, asthma, heart disease, atherosclerosis, and osteoporosis, or a pharmaceutically acceptable salt thereof.

14 Claims, No Drawings

OTHER PUBLICATIONS

Samanfaray et al, PubMed Abstract 14569466, also cited as J. Cancer Res. Clin. Oncol., Oct. 16, 2003.*

Letavic et al, PubMed Abstract 12951101, also cited as Bioorg. Med. Chem. Lett., 13/19,3243–6(2003).*

Fernabdes et al, PubMed Abstract 12082286, also cited as Biorheology,39/1–2, 237–46(2002).*

Chemical Abstract DN 106:83869, also cited as Khimiya Get.Soed.,6,826–36(1986).*

Chemical Abstract DN 121:50115, also cited as WO 9408577.*

Chemical Abstract DN121:217479, also cited as JP 05303181.*

Chemical Abstract CHEMCATS: Abstract No. 2001: 455599 for Enamine Product Listing Order No. TO502–9497, published May 15, 2001.

Chemical Abstract CAPLUS: Abstract No. 2000:645983 for Honma, et al., "Prepaaration of [2.2.1] and [3.1.1]bicyclo-heptane antagonistic to both PGD2/TXA2 receptors", PCT International application publication No. WO 2000053573 AI, published Sep. 14, 2000.

Chemical Abstract CAPLUS: Abstract No. 1998:776671 for Ranges et al., "Inhibition of p38 kinase activity by aryl ureas", PCT International application publication No. WO 98/52558 A1, published Nov. 26, 1998.

Chemical Abstract CAPLUS: Abstract No. 1998:223896 for Kanoaka, et al., "Synthesis and evaluation of nitro 5–dea-zaflavin–pyrrolecarboxamide(s) hybrid molecules as novel DNA targeted bioreductive antitumor agents", Bioorg. Med. Chem, 1998;6(3):301–314.

Chemical Abstract CAPLUS: Abstract No. 1997:18107 for Matsunaga, et al., "Preparation of distamycin derivatives as anticancer agents", Japanese patent No. JP 08269008 A2, published Oct. 15, 1998.

Chemical Abstract CAPLUS: Abstract No. 1995:445273 for Xie et al., "Protein kinase C–alpha inhibitors; structure–activity relationships in bis–indole series", Bioorg. Med. Chem. Lett. 1995;5(5):497–500.

Chemical Abstract CAPLUS: Abstract No. 1994:436147 for Parrick, et al., "The synthesis of radiosensitizers designed to bind to the minor groove of duplex DNA", J. Chem. Soc., Perkin Trans. I, 1993;(22):2681–2685.

Chemical Abstract CAPLUS: Abstract No. 1994:408949 for Parrick, et al., "Targeting radiosensitizers to DNA by minor groove binding: nitroarenes based on netropsin and dista-mycin", Bioorg. Med. Chem. Lett., 1993;3(8):1697–702 [sic].

Chemical Abstract CAPLUS: Abstract No. 1991:143124 for Goda, et al., "Preparation of thiophene–2, 5–dicarboxylic acid diesters, tetrahydrothiophene–2, 5–dicarboxylic acid diesters and dibenzoxazolythiophenes", European patent application No. EP 387725 A2/A3, published Sep. 19, 1990.

Derwent Abstract No. 2000–451668/39 for Yagami, et al., "Use of a thromboxane A2 antagonist or synthase inhibitor for treating central nervous system diseases e.g. Alzheimer type dementia", PCT International application Publication No. WO 200030683 A1, published Jun. 2, 2000.

Derwent Abstract No. 97–164896/15 for Boyle, et al., "4–Mercapto–pyrrolidine derives. —are farnesyl–protein transferase inhibitors useful for the treatment of cancer", PCT International application publication No. WO 9706138 A1, published Feb. 20, 1997.

Derwent Abstract No. 90–283971/38 for Sumitomo Seika Chem., "New (tetra:hydro) thiophene–2, 5–dicarboxylic acid diester cpds, used in prepn. of 2,5–dibenzoxazolylth-iophene with ortho–amino:phenol cpd.", EP 387 725 A, published Sep. 19, 1990.

Beilstein Institute Abstract: Registry No. 5131630, entered Aug. 28, 1992.

Beilstein Institute Abstract: Registry No. 8241589, entered Feb. 29, 2000.

Beilstein Institute Abstract: Registry No. 319664, entered Jun. 27, 1988.

Beilstein Institute Abstract: Registry No. 4211848, entered Oct. 23, 1991.

Beilstein Institute Abstract: Registry No. 8526650, entered Jul. 18, 2000.

Beilstein Institute Abstract: Registry No. 4211276, entered Oct. 23, 1991.

Beilstein Institute Abstract: Registry No. 4213605, entered Oct. 23, 1991.

Chemical Abstract CAOLD: Abstract No. CA64:3741h for "2,5–di(2–benzoxazoly) thiophenes", U.S. Appl. No. 3255199, issued Jun. 7, 1966.

Chemical Abstract CHEMCATS: Abstract No. 2001:240881 for ChemDiv, Inc. Product Library order No. 000L–2645 and for Nanosyn Combinatorial Synthesis Inc.'s Pharma Library Collection Order No. NS38811, published Apr. 26, 2001.

Chemical Abstract CAPLUS: Abstract No. 1997:579701 for Dervan, et al., "Preparation of polypyrrole and polyimida-zole carboxamide building blocks for solid–phase synthesis of polyamides", PCT International application publication No. WO 9730975, published Aug. 28, 1997.

Chemical Abstract CAPLUS: Abstract No. 1978:546779 for Henrick, et al., "Pyridine esters of cyclopropanecarboxylic acid", U.S. Appl. No. 4093622, issued Jun. 6, 1978.

Chemical Abstracts CA: Abstract No. 88:131945 for Reed et al., "Citrus red mites: evaluation of control obtained with a new class of miticides containing the cyclopropane moiety", J. Econ. Entomol., 1978;71(1):93–96.

Chemical Abstracts CA: Abstract No. 85:105335 for Hen-rick et al., "Ovicidal activity and its relation to chemical structure for the two–spotted spider mite (*Tetranychus Urti-cae* Koch) in a new class of miticides containing the cyclopropyl group", J. Agric. Food Chemical, 1976;24(5):1023–1029.

Chemical Abstract CAPLUS: Abstract No. 1975:496546 for Henrick, et al., "Cyclopropane compounds", U.S. Appl. Nos. 3928413 and 3925460, issued Dec. 23, 1975 and Dec. 9, 1975, respectively.

Chemical Abstract CAPLUS: Abstract No. 1991:143124 for Goda, et al., "Preparation of thiophene–2,5–dicarboxylic acid diesters, tetrahydrothiophene–2,5–dicarboxylic acid diesters and dibenzoxazolylthiophenes", Eur. Patent Appli-cation No. EP 387725, published Sep. 19, 1990.

Chemical Abstracts CAPLUS: Abstract No. 1968:410351 for Liechti, et al., "Dichlorotetrahydrothiophene–2, 5–dicar-boxylic acid dichlorides", Swiss Patent No. CH437347, issued Nov. 30, 1967.

Chemical Abstracts CAOLD: Abstract No. CA61:643h for CIBA Ltd., "Dicarboxylic acid dichlorides (chlorinated)", U.S. Appl. No. 3127416, issued Mar. 31, 1964.

Chemical Abstract CAPLUS: Abstract No. 1967:19851 for CIBA Ltd., "Oxazole derivatives, optical brightening agents", Dutch patent No. NL6513852, issued Apr. 28, 1966.

Chemical Abstract CA: Abstract No. 105:190736 for Baldwin et al., "Total synthesis of antitumor agent AT–125, (alphaS, 5S)–alpha–amino–3–chloro–4, 5–dihydro–5–isoxazoleacetic acid", Tetrahedron, 1985;41(22):5241–5260.

Chemical Abstract CHEMCATS Abstract No. 2001:121492 for Nanosyn Combinatorial Synthesis Inc.'s Pharma Library Collection Order No. NS2477, published May 14, 2001.

Chemical Abstract CA: Abstract No. 112:139933 for Cai, et al., "New liquid–crystalline aromatic polyesters derived from thiophenes", Polym. Mater. Sci. English, 1989;61:383–387.

Chemical Abstract CA: Abstract No. 86:181002 for Dewar et al., "Effect of structure on the stability of nematic mesophases", Liquid Crystalline Ordered Fluids, 1973;2:733–741.

Chemical Abstract CA: Abstract No. 83:211550 for Dewar et al., "Factors influencing the stabilities of nematic liquid crystals", J. Am. Chem. Soc., 1975;97(23):6658–6662.

Chemical Abstract CAPLUS: Abstract No. 1997:247953 for Boyle, et al., "Preparation of 2–aminomethyl–4–mercaptopyrrolidines and analogs as farnesyl transferase inhibitors", PCT International application publication No. WO9706138, published Feb. 20, 1997.

Chemical Abstract CAPLUS: Abstract No. 1991:143124 for Goda, et al., "Preparation of thiophene–2, 5–dicarbolylic acid diesters, tetrahydrothiophene–2, 5–dicarboxylic acid diesters and dibenzoxazolylthiophenes", European Patent Application No. EP387725, published Sep. 19, 1990.

Chemical Abstract CA: Abstract No. 114:42352 for Yon-Hin et al., "An efficient route to vinylporphyrins", Can. J. Chem. 1990;68(10):1867–1875.

Chemical Abstract CA: Abstract No. 106:49840 for Smith et al., "Total synthesis of derivatives of protoporphyrin IX regioselectively labeled with carbon–13 in the methyls", J. Organic Chemical [sic], 1986;51(24):4667–4676.

Chemical Abstract CA: Abstract No. 104:108952 for Smith et al., "Methyl deuteration reactions in vinylporphyrins: protoporphyrins IX, III, and XIII", J. Organic Chemical [sic], 1986;51(5):666–671.

Chemical Abstract CA: Abstract No. 100:50827 for Smith et al., "Neighboring group participation in the pyrrole series", J. Organic Chemical [sic], 1983;48(23):4296–4302.

Chemical Abstract CA: Abstract No. 87:117829 for Buldain et al., J. Organic Chemical [sic], 1977;42(18):2953–2956.

Chemical Abstract CA: Abstract No. 86:181002 for Dewar, et al., "Effect of structure on the stability of nematic mesophases", Liquid Crystalline Ordered Fluids, 1973;2:733–741.

Chemical Abstract CA: Abstract No. 83:21150 for Dewar et al., "Factors influencing the stabilities of nematic liquid crystals", J. Am. Chem. Soc., 1975;97(23):6658–6652.

Chemical Abstract CHEMCATS: Abstract No. 2001:569621 for Enamine Product Listing order No. T0502–9497, published May 15, 2001.

Chemical Abstract CA: Abstract No. 112:139933 for Cai, et al., "New liquid–crystalline aromatic polyesters derived from thiophenes", Polym. Mater. Sci. English, 1989;61:383–387.

Chemical Abstract CHEMCATS: Abstract No. 2001:571238 for Enamine Product Listing Order No. T0503–3105, published May 15, 2001.

Chemical Abstract CAPLUS: Abstract No. 1990:552387 for Kelly, et al., "CC–1065 analogs having two CPI subunits useful as antitumor agents and ultraviolet light absorbers", European Patent Application No. EP359454, published Mar. 21, 1990.

Chemical Abstract CAPLUS: Abstract No. 1996:449419 for Kreuder, et al., "Poly (paraphenylene vinylene) derivatives and their use as electroluminescent materials", PCT International Publication No. WO9610617, published Apr. 11, 1996.

Chemical Abstract CA: Abstract No. 115:61595 for Cai et al., "New thermotropic liquid crystals derived from thiophenes", Liquid Crystalline, 1991;9(5):617–634.

Chemical Abstract CAPLUS: Abstract No. 1991:143124 for Goda et al., "Preparation of thiophene–2, 5–dicarboxylic acid diesters, tetrahydrothiophene–2, 5–dicarboxylic acid diesters and dibenzoxazolylthiophenes", European Patent Application No. EP387725, published Sep. 19, 1990.

Chemical Abstract CA: Abstract No. 112:139933 for Cai et al., "New liquid–crystalline aromatic polyesters derived from thiophenes", Polym. Mater. Sci. English, 1989;61:383–387.

Beilstein Institute Abstract: Registry No. 152320, entered Jun. 27, 1988.

Beilstein Institute Abstract: Registry No. 163097, entered Jun. 27, 1988.

Beilstein Institute Abstract: Registry No. 163098, entered Jun. 27, 1988.

Beilstein Institute Abstract: Registry No. 478601, entered Nov. 28, 1998.

Beilstein Institute Abstract: Registry No. 4411575, entered Dec. 2, 1991.

Beilstein Institute Abstract: Registry No. 4502615, entered Dec. 2, 1991.

Beilstein Institute Abstract: Registry No. 162266, entered Nov. 29, 1988.

Beilstein Institute Abstract: Registry No. 168034, entered Jun. 27, 1988.

Beilstein Institute Abstract: Registry No. 176297, entered Jun. 27, 1988.

Beilstein Institute Abstract: Registry No. 176298, entered Jun. 27, 1988.

Beilstein Institute Abstract: Registry No. 176306, entered Jun. 27, 1988.

Beilstein Institute Abstract: Registry No. 1378165, entered Nov. 29, 1988.

M. W. Roomi, et al., "The Hantzsch pyrrole synthesis", Canadian Journal of Chemistry, vol. 48, 1970, pp. 1689–1697.

Ralph P. Robinson, et al., "Design and Synthesis of 2–Oxo–imidazolidine–4–carboxylic Acid Hydroxyamides as Potent Matrix Metalloproteinase–13 Inhibitors", Biorganic & Medicinal Chemistry Letters 11 (2001), pp. 1211–1213.

European Search Report, Serial No. 02255922.3–2217, 2003.

Office Action mailed Jun. 16, 2003 in U.S. Appl. No. 10/264,764.

Chen, et al., "Structure–Based Design of a Novel, Potent, and Selective Inhibitor for MMP–13 Utilizing NMR Spectroscopy and Computer–Aided Molecular Design" JACS, 2000; 122:9648–9654.

Lovejoy, et al., "Crystal structures of MMP–1 and –13 reveal the structural basis for selectivity of collagenase inhibitors", Nature Structural Biol., 1999; 6:217–221.

Moy, et al., High–resolution solution structure of the catalytic fragment of human collagenase–3 (MMP–13) complexed with a hydroxamic acid inhibitor, J. Mol. Biol., 2000; 302:671–689.

Mitchell, et al., "Cloning, Expression, and Type II Collagenolytic Activity of Matrix Metalloproteinase–13 from Human Osteoarthritic Cartilage", J. Clin. Invest., 1996; 97(3):761–768.

Neuhold, et al., "Postnatal expression in hyaline cartilage of constitutively active human collagenase–3 (MMP–13) induces osteoarthritis in mice", J. Clin. Invest., 2001; 107: 35–44.

Dahlberg, et al., Selective Enhancement of Collagenase–Mediated Cleavage of Resident Type II Collagen in Cultured Osteoarthritic Cartilage and Arrest with a Synthetic Inhibitor that Spares Collagenase 1 (Matrix Metalloproteinase 1), Arthrit. & Rheum., 2000; 43(3): 673–682.

Billinghurst, et al., "Comparison of the Degradation of Type II Collagen and Proteoglycan in Nasal and Articular Cartilages Induced by Interleuken–1 and the Selective Inhibition of Type II Collagen Cleavage by Collagenase", Arthrit. & Rheum., 2000; 43(3): 664–672.

Billinghurst, et al., "Enhanced Cleavage of Type II Collagen by Collagenases in Osteoarthritic Articular Cartilage", J. Clin. Invest., 1997; 99:1534–1545.

Hirota, et al., "Novel Synthesis of Pyrido[3,4–d]pyrimidines, Pyrido[2,3–d]–pyrimidines, and Quinazolines via Palladium–Catalyzed Oxidative coupling", Heterocycles, 1994; 37(1):563–570.

Kanaoka et al., "Synthesis and Evaluation of Nitro 5–Deazaflavin–pyrrolecarboxamide(s) Hybrid Molecules as Novel DNA Targeted Bioreductive Antitumor Agents", Bioorganic & Medicinal Chemistry, vol. 6, 1998, pp. 301–314 (cited by previously disclosed Chemical Abstract CAPLUS: Abstract No. 1998:223896).

Xie et al., "Protein Kinase C–alpha Inhibitors: Structure–Activity Relationships in Bis–Indole Series", Biorganic & Medicinal Chemistry Letters, vol. 5, No. 5, 1995, pp. 497–500 (cited by previously disclosed Chemical Abstract CAPLUS: Abstract No. 1995:445273).

Parrick et al., "The Synthesis of Radiosensitizers Designed to Bind to the Minor Groove of Duplex DNA", J. Chem. Soc. Perkin Trans 1, (22), 1993, pp. 2681–2685 (cited by previously disclosed Chemical Abstract CAPLUS: Abstract No. 1994:436147).

Parrick et al., "Targeting Radiosensitizers to DNA by Minor Groove Binding: Nitroarenes Based on Netropsin and Distarnycin", Biorganic & Medicinal Chemistry Letters, vol. 3, No. 8, 1993, pp. 1697–1702 (cited by previously disclosed Chemical Abstract CAPLUS: Abstract No. 1994:408949).

Reed and Moreno, "Citrus Red Mites: Evaluation of Control Obtained with a New Class of Miticides Containing the Cyclopropane Moiety", J. Econ. Entomol., vol. 71, No. 1, 1978, pp. 93–96 (cited by previously disclosed Chemical Abstract CA: Abstract No. 88:131945).

Henrick et al., "Ovicidal Activity and Its Relationship to Chemical Structure for the Two–Spotted Spider Mite (Tetranychus urticae Koch) in a New Class of Miticides Containing the Cyclopropyl Group", J. Agric. Food Chem., vol. 24, No. 5, 1976, pp. 1023–1029 (cited by previously disclosed Chemical Abstract CA: Abstract No. 85:105335).

Baldwin et al., "Total Synthesis of Antitumor Agent AT–125, ($_\alpha$S,5S)–$_\alpha$–Amino–3–chloro–4, 5–dihydro–5–isoxazoleacetic Acid", Tetrahedron, vol. 41, No. 22, 1985, pp. 5241–5260 (cited by previously disclosed Chemical Abstract CA: Abstract No. 105: 190736).

Dewar and Riddle, "Factors Influencing the Stabilities of Nematic Liquid Crystals", J. Am. Chem. Soc., vol. 97, No. 23, 1975, pp. 6658–6662 (cited by previously disclosed Chemical Abstract CA: Abstract No. 83:211550).

Yon–Hin et al., "An efficient route to vinylporphyrins", Can J. Chem., vol. 68, No. 10, 1990, pp. 1867–1875 (cited by previously disclosed Chemical Abstract CA: Abstract No. 114:42352).

Smith et al., "Total Synthesis of Derivatives of Protoporphyrin IX Regioselectively Labeled with Carbon–13 in the Methyls", J. Org. Chem., vol. 51, No. 24, 1986, pp. 4667–4676 (cited by previously disclosed Chemical Abstract CA: Abstract No. 196:49840).

Smith et al., "Methyl Deuteration Reactions in Vinylporphyrine: Protoporphyrins IX, III, and XIII", J. Org. Chem., vol. 51, No. 5, 1986, pp. 666–671 (cited by previously disclosed Chemical Abstract CA: Abstract No. 104:108952).

Smith et al., "Neighboring Group Participation in the Pyrrole Series", J. Org. Chem., vol. 48, No. 23, 1983, pp. 4296–4302 (cited by previously disclosed Chemical Abstract CA: Abstract No. 100:50827).

Buldain et al., "Synthesis of Tricarboxylic Porphyrin Enzymically Formed from Coproporphyrinogen IV", J. Org. Chem., vol. 42, No. 18, 1977, pp. 2953–2956 (cited by previously disclosed Chemical Abstract CA: Abstract No. 87:117829).

Dewar et al., "Effect of Structure on the Stability of Nematic Mesophases", Liquid Crystalline Ordered Fluids, vol. 2, 1973, pp. 733–741, (cited by previously disclosed Chemical Abstract CA: Abstract No. 86:181002).

Cai et al., "New Liquid Crystalline Aromatic Polyesters Derived from Thiophenes", Polym. Mater. Sci. English, vol. 61, 1989, pp. 383–387 (cited by previously disclosed Chemical Abstract CA: Abstract No. 112:139933).

Cai and Samulski, "New thermotropic liquid crystals derived from thiophenes," Liquid Crystals, vol. 9, No. 5, 1991, pp. 617–634 (cited by previously disclosed Chemical Abstract CA: Abstract No. 115:61595).

* cited by examiner

DIACID-SUBSTITUTED HETEROARYL DERIVATIVES AS MATRIX METALLOPROTEINASE INHIBITORS

CROSS-REFERENCE TO RELATED APPLICATIONS

This application claims benefit of priority from U.S. Provisional Patent Application Number 60/318,488, filed Sep. 10, 2001.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION (1) Field of the Invention

The present invention relates to inhibitors of the enzyme matrix metalloproteinase-13 ("MMP-13"), pharmaceutical compositions comprising said inhibitors, and methods of treating diseases responsive to inhibition of MMP-13 comprising administering said inhibitors. The preceding statement is meant to be illustrative of the field of the invention only, and should not be construed to limit the scope of the present invention, which is fully, clearly, concisely, and exactly described below.

(2) Description of the Related Art

Matrix metalloproteinases (sometimes referred to as "MMPs") are naturally-occurring (i.e., endogenous) enzymes found in most mammals. Over-expression and activation of MMPs or an imbalance between MMPs and natural endogenous tissue inhibitors of MMPs (sometimes referred to as "TIMPs") have been suggested as factors in the pathogenesis of diseases characterized by the breakdown of extracellular matrix or connective tissues.

Stromelysin-1 and gelatinase A are members of the matrix metalloproteinase ("MMP") family. Other members of the MMP family include fibroblast collagenase ("MMP-1"), neutrophil collagenase ("MMP-8"), gelatinase B ("92 kDa gelatinase" or "MMP-9"), stromelysin-2 ("MMP-10"), stromelysin-3 ("MMP-11"), matrilysin ("MMP-7"), collagenase-3 ("MMP-13"), and other newly discovered membrane-associated matrix metalloproteinases (Sato H., Takino T., Okada Y., Cao J., Shinagawa A., Yamamoto E., and Seiki M., *Nature*, 1994;370:61–65). Overactivity of these enzymes has been implicated in a number of diseases which result from breakdown of connective tissue or extracellular matrix, including such diseases as rheumatoid arthritis, osteoarthritis, osteoporosis, periodontitis, multiple sclerosis, gingivitis, corneal epidermal and gastric ulceration, atherosclerosis, neointimal proliferation which leads to restenosis and ischemic heart failure, stroke, renal disease, macular degeneration, and tumor metastasis. Inhibition of MMPs is now a recognized method for preventing and treating these diseases and other diseases responsive to inhibition of MMPs, as MMP inhibitors curtail and/or eliminate the breakdown of connective tissues or extracellular matrices that is intrinsic to these disease states.

MMPs contain a catalytic zinc cation that typically must coordinate to a functional group in a substrate before cleavage of the substrate by the MMP can occur. This catalytic zinc is usually the focal point for inhibitor design. For example, the modification of substrate mimics by introducing zinc-chelating groups has generated potent inhibitors such as peptide hydroxamates and thiol-containing peptides. Peptide hydroxamates and TIMPs have been used successfully to treat animal models of cancer and inflammation. MMP inhibitors have also been used to prevent and treat congestive heart failure and other cardiovascular diseases, as described in U.S. Pat. No. 5,948,780.

A major limitation on the use of currently known MMP inhibitors is their lack of specificity for any particular MMP enzyme. Further, recent studies have shown that MMP inhibitors also inhibit the production of tumor necrosis factor alpha ("TNF-α") by inhibiting TNF-α converting enzyme ("TACE"), which is also known as TNF-α convertase. Recent data has established that specific MMP enzymes are associated with some diseases, but are not associated with others. A nonselective inhibitor of MMPs may potentially inhibit MMPs that are not involved in the process of the particular disease being treated, thereby "diluting" the inhibitor's effectiveness and, further, possibly leading to undesirable side effects in vivo.

The MMPs are generally categorized based on their substrate specificity, and indeed the collagenase subfamily of MMP-1, MMP-8, and MMP-13 preferentially cleave native interstitial collagens, and thus usually are associated only with diseases linked to such interstitial collagen tissue. Nevertheless, it seems some diseases may involve overactivity of only one MMP. This is indicated by the recent discovery that MMP-13 alone is over expressed in breast carcinoma, while MMP-1 alone is over expressed in papillary carcinoma (see Chen et al., *J. Am. Chem. Soc.*, 2000;122:9648–9654).

A selective inhibitor of MMP-13 would thus be valuable. However, there appears to be only one highly selective inhibitor of MMP-13, namely WAY-170523 reported by Chen et al., Supra., 2000. The need continues to find new low molecular weight compounds that are potent and selective MMP inhibitors, and that have an acceptable therapeutic index of toxicity/potency, which makes them amenable for use clinically in the prevention and treatment of the associated disease states.

One aspect of the present invention is a group of MMP-13 inhibitor compounds characterized as being diacid-substituted heteroaryl derivatives. A further aspect of this invention is MMP-13 inhibitor compounds that are selective inhibitors of MMP-13. All that is needed to practice the invention is to administer from 1 to 6 times daily to a patient in need of treatment, a therapeutically effective amount of a compound of the invention. Determination of dosage forms, amounts of a compound to administer, routes of administration, and identification of patients in need of treatment is discussed below and is within the average skill in veterinary or medical arts.

The preceding description is for background purposes only, and is not to be construed, in part or in whole, as an admission of prior art.

BRIEF SUMMARY OF THE INVENTION

This invention provides diacid-substituted heteroaryl derivatives that are inhibitors of matrix metalloproteinase-13 enzymes. The invention is more particularly directed to a compound of Formula I

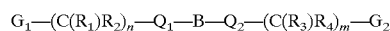

$$G_1\text{—}(C(R_1)R_2)_n\text{—}Q_1\text{—}B\text{—}Q_2\text{—}(C(R_3)R_4)_m\text{—}G_2 \qquad I$$

or a pharmaceutically acceptable salt thereof, wherein:

$G_1$ and $G_2$ are independently selected from:
- hydrogen,
- $C_1$–$C_{12}$ alkyl,
- substituted $C_1$–$C_{12}$ alkyl,
- $C_2$–$C_{12}$ alkenyl,
- substituted $C_2$–$C_{12}$ alkenyl,
- $C_2$–$C_{12}$ alkynyl,
- substituted $C_2$–$C_{12}$ alkynyl,
- $C_3$–$C_{12}$ cycloalkyl,
- substituted $C_3$–$C_{12}$ cycloalkyl,
- phenyl,
- substituted phenyl,
- naphthyl,
- substituted naphthyl,
- heteroaryl, and
- substituted heteroaryl;

$R_1$, $R_2$, $R_3$, and $R_4$ are independently, at each occurrence, selected from:
- hydrogen,
- methyl,
- cyano, and
- fluoro, or $R_1$ and $R_2$, or $R_3$ and $R_4$ may be taken together with the carbon atom to which they are each attached to form C=O;

n and m are independently an integer of from 1 to 3;

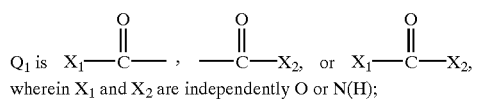

wherein $X_1$ and $X_2$ are independently O or N(H);

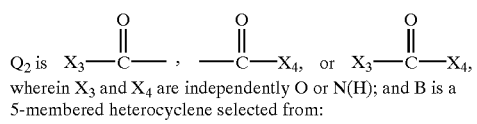

wherein $X_3$ and $X_4$ are independently O or N(H); and B is a 5-membered heterocyclene selected from:

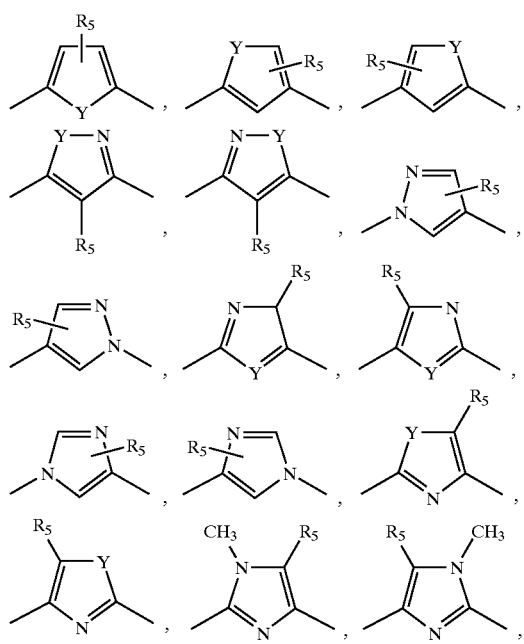

-continued

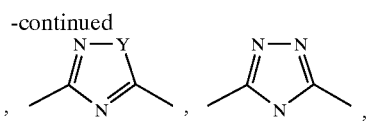

wherein Y is O, S, or N—$CH_3$; and $R_5$ is selected from:
- hydrogen,
- $C_1$–$C_{12}$ alkyl,
- substituted $C_1$–$C_{12}$ alkyl,
- $C_2$–$C_{12}$ alkenyl,
- substituted $C_2$–$C_{12}$ alkenyl,
- $C_2$–$C_{12}$ alkynyl,
- substituted $C_2$–$C_{12}$ alkynyl,
- $C_3$–$C_{12}$ cycloalkyl,
- substituted $C_3$–$C_{12}$ cycloalkyl,
- phenyl,
- substituted phenyl,
- benzyl,
- substituted benzyl,
- O—$R_6$, wherein $R_6$ is hydrogen, $C_1$–$C_{12}$ alkyl, phenyl, or benzyl,
- S—$R_6$, wherein $R_6$ is hydrogen, $C_1$–$C_{12}$ alkyl, phenyl, or benzyl,
- C(O)—$R_6$, wherein $R_6$ is hydrogen, $C_1$–$C_{12}$ alkyl, phenyl, or benzyl,
- $CO_2R_6$, wherein $R_6$ is hydrogen, $C_1$–$C_{12}$ alkyl, phenyl, or benzyl,
- C(O)—N(H)$OR_6$, wherein $R_6$ is hydrogen, $C_1$–$C_{12}$ alkyl, phenyl, or benzyl,
- C(=$NOR_6$)—H, wherein $R_6$ is hydrogen, $C_1$–$C_{12}$ alkyl, phenyl, or benzyl,
- C(=$NOR_6$)—$CH_3$, wherein $R_6$ is hydrogen, $C_1$–$C_{12}$ alkyl, phenyl, or benzyl,
- $CH_2OR_6$, wherein $R_6$ is hydrogen, $C_1$–$C_{12}$ alkyl, phenyl, or benzyl,
- $CH_2N(R_6)R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A)

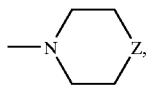

(A)

wherein Z is $CH_2$, O, S, or N—R, wherein R is H or $CH_3$,

C(H)F—OH, $CF_2$—OH,

O—C(O)—$R_6$, wherein $R_6$ is hydrogen, $C_1$–$C_{12}$ alkyl, phenyl, or benzyl, C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, N($R_6$)—C(O)—$R_7$, wherein $R_6$ and $R_7$ are independently hydrogen, $C_1$–$C_{12}$ alkyl, phenyl, or benzyl, N(H)—C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, N(H)—C(O)—$OR_6$, wherein $R_6$ is independently hydrogen, $C_1$–$C_{12}$ alkyl, phenyl, or benzyl, N(H)—S(O)$_2$—($C_1$–$C_{12}$ alkyl), O—C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, $NO_2$, $N_3$, N(H)—C(N$R_8$)—N($R_6$)$R_7$, wherein $R_6$ and $R_7$ are independently hydrogen, $C_1$–$C_4$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and $R_8$ is hydrogen, hydroxy, methoxy, or CN,

CN, halo,

S(O)—($C_1$–$C_{12}$ alkyl),

S(O)$_2$—($C_1$–$C_{12}$ alkyl),

S(O)$_2$—N($R_6$)—($R_7$), wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and S(O)$_2$CF$_3$, wherein at least one of $R_1$, $R_2$, $R_3$, $R_4$, or $R_5$ is not hydrogen, or at least one of $G_1$ or $G_2$ is substituted $C_1$–$C_{12}$ alkyl, substituted $C_2$–$C_{12}$ alkenyl, substituted $C_2$–$C_{12}$ alkynyl, substituted $C_3$–$C_{12}$ cycloalkyl, substituted phenyl, substituted naphthyl, or substituted heteroaryl.

A preferred embodiment of the present invention is a compound of Formula II

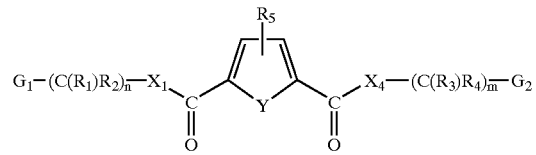

II or a pharmaceutically acceptable salt thereof, wherein Y is O, S, or N—$CH_3$, and $G_1$, $G_2$, $R_1$, $R_2$, $R_3$, $R_4$, n, m, $X_1$, $X_4$, and $R_5$ are as defined above for Formula I.

More preferred is a compound of Formula II, or a pharmaceutically acceptable salt thereof, wherein Y is S and $G_1$, $G_2$, $R_1$, $R_2$, $R_3$, $R_4$, n, m, $X_1$, $X_4$, and $R_5$ are as defined above for Formula I.

Still more preferred is a compound of Formula II, or a pharmaceutically acceptable salt thereof, wherein Y is S, $G_1$ and $G_2$ are independently phenyl or substituted phenyl, and $R_1$, $R_2$, $R_3$, $R_4$, n, m, $X_1$, $X_4$, and $R_5$ are as defined above for Formula I.

Still more preferred is a compound of Formula II, or a pharmaceutically acceptable salt thereof, wherein Y is S, $G_1$ and $G_2$ are independently substituted phenyl, n and m are each 1, and $R_1$, $R_2$, $R_3$, $R_4$, $X_1$, $X_4$, and $R_5$ and are as defined above for Formula I.

Still more preferred is a compound of Formula II, or a pharmaceutically acceptable salt thereof, wherein Y is S, $G_1$ and $G_2$ are independently substituted phenyl, wherein the substituents are selected from 1,2-methylenedioxy, methoxy, ethoxy, —O—C(O)$CH_3$, carboxy, carbomethoxy, and carboethoxy, n and m are each 1, and $R_1$, $R_2$, $R_3$, $R_4$, $X_1$, $X_4$, and $R_5$ are as defined above for Formula I.

Still more preferred is a compound of Formula II, or a pharmaceutically acceptable salt thereof, wherein Y is S, n and m are each 1, $G_1$ and $G_2$ are each

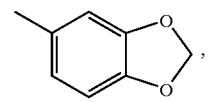

$R_5$ is hydrogen or OMe, and $R_1$, $R_2$, $R_3$, $R_4$, $X_1$, and $X_4$ are as defined above for Formula I.

Still more preferred is a compound of Formula II, or a pharmaceutically acceptable salt thereof, selected from:

thiophene-2,5-dicarboxylic acid, bis[(1,3-benzodioxol-5-ylmethyl)ester];

thiophene-2,5-dicarboxylic acid, bis[(1,3-benzodioxol-5-ylmethyl)amide];

thiophene-2,5-dicarboxylic acid, 3-methoxy-, bis[(1,3-benzodioxol-5-ylmethyl)ester]; and thiophene-2,5-dicarboxylic acid, 3-methoxy-, bis[(1,3-benzodioxol-5-ylmethyl)amide].

Also still more preferred is a compound of Formula II, or a pharmaceutically acceptable salt thereof, named 3-methoxy-thiophene-2,5-dicarboxylic acid bis-benzylamide.

Another preferred embodiment of the present invention is a compound of Formula III

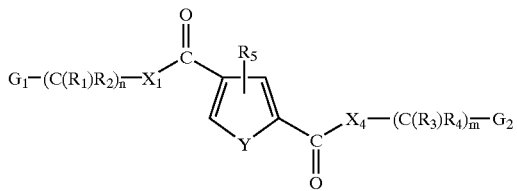

III or a pharmaceutically acceptable salt thereof, wherein Y is O, S, or N—CH$_3$, and G$_1$, G$_2$, R$_1$, R$_2$, R$_3$, R$_4$, n, m, X$_1$, X$_4$, and R$_5$ are as defined above for Formula I.

More preferred is a compound of Formula III, or a pharmaceutically acceptable salt thereof, wherein Y is S or N—CH$_3$, and G$_1$, G$_2$, R$_1$, R$_2$, R$_3$, R$_4$, n, m, X$_1$, X$_4$, and R$_5$ are as defined above for Formula I.

Still more preferred is a compound of Formula III, or a pharmaceutically acceptable salt thereof, wherein Y is S, G$_1$ and G$_2$ are independently phenyl or substituted phenyl, and R$_1$, R$_2$, R$_3$, R$_4$, R$_5$, n, m, X$_1$, and X$_4$ are as defined above for Formula I.

Still more preferred is a compound of Formula III, or a pharmaceutically acceptable salt thereof, wherein Y is S or N—CH$_3$, G$_1$ and G$_2$ are independently substituted phenyl, n and m are each 1, and R$_1$, R$_2$, R$_3$, R$_4$, X$_1$, X$_4$, and R$_5$ are as defined above for Formula I.

Still more preferred is a compound of Formula III, or a pharmaceutically acceptable salt thereof, wherein Y is S or N—CH$_3$, G$_1$ and G$_2$ are independently substituted phenyl, wherein the substituents are selected from 1,2-methylenedioxy, methoxy, ethoxy, —O—C(O)CH$_3$, carboxy, carbomethoxy, and carboethoxy, n and m are each 1, and R$_1$, R$_2$, R$_3$, R$_4$, X$_1$, X$_4$, and R$_5$ are as defined above for Formula I.

Still more preferred is a compound of Formula III, or a pharmaceutically acceptable salt thereof, wherein Y is S, G$_1$, and G$_2$ are each

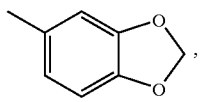

n and m are each 1, and R$_1$, R$_2$, R$_3$, R$_4$, R$_5$, X$_1$, and X$_4$ are as defined above for Formula I.

Also still more preferred is a compound of Formula III, or a pharmaceutically acceptable salt thereof, wherein Y is N—CH$_3$, G$_1$ and G$_2$ are each

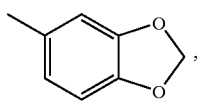

n and m are each 1, and R$_1$, R$_2$, R$_3$, R$_4$, R$_5$, X$_1$, and X$_4$ are as defined above for Formula I.

Still more preferred is a compound of Formula III, or a pharmaceutically acceptable salt thereof, selected from:
 thiophene-2,4-dicarboxylic acid, bis[(1,3-benzodioxol-5-ylmethyl)ester];
 thiophene-2,4-dicarboxylic acid, bis[(1,3-benzodioxol-5-ylmethyl)amide];
 1H-pyrrole-2,4-dicarboxylic acid, 1-methyl-, bis[(1,3-benzodioxol-5-ylmethyl)ester]; and 1H-pyrrole-2,4-dicarboxylic acid, 1-methyl-, bis[(1,3-benzodioxol-5-ylmethyl)amide].

Also still more preferred is a compound of Formula III, or a pharmaceutically acceptable salt thereof, named 4-({[5-(4-methoxy-benzylcarbamoyl)-2-methylamino-thiophene-3-carbonyl]-amino}-methyl)-2-methyl-benzoic acid.

Another preferred embodiment of the present invention is a compound of Formula IV

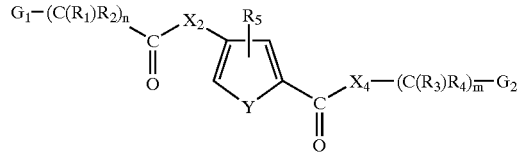

IV or a pharmaceutically acceptable salt thereof, wherein Y is O, S, or N—CH$_3$, and G$_1$, G$_2$, R$_1$, R$_2$, R$_3$, R$_4$, n, m, X$_2$, X$_4$, and R$_5$ are as defined above for Formula I.

More preferred is a compound of Formula IV, or a pharmaceutically acceptable salt thereof, wherein Y is S and G$_1$, G$_2$, R$_1$, R$_2$, R$_3$, R$_4$, n, m, X$_2$, X$_4$, and R$_5$ are as defined above for Formula I.

Still more preferred is a compound of Formula IV, or a pharmaceutically acceptable salt thereof, wherein Y is S, G$_1$ and G$_2$ are independently phenyl or substituted phenyl, and R$_1$, R$_2$, R$_3$, R$_4$, R$_5$, n, m, X$_2$, and X$_4$ are as defined above for Formula I.

Still more preferred is a compound of Formula IV, or a pharmaceutically acceptable salt thereof, wherein Y is S, G$_1$ and G$_2$ are independently phenyl or substituted phenyl, n and m are each 1, R$_5$ is methyl, and R$_1$, R$_2$, R$_3$, R$_4$, X$_2$, and X$_4$ are as defined above for Formula I.

Still more preferred is a compound of Formula IV, or a pharmaceutically acceptable salt thereof, wherein Y is S, G$_1$ and G$_2$ are independently phenyl or substituted phenyl, wherein the substituents are selected from 1,2-methylenedioxy, methoxy, ethoxy, —O—C(O)CH$_3$, carboxy, carbomethoxy, and carboethoxy, n and m are each 1, and R$_1$, R$_2$, R$_3$, R$_4$, X$_2$, X$_4$, and R$_5$ are as defined above for Formula I.

Still more preferred is a compound of Formula IV, or a pharmaceutically acceptable salt thereof, wherein Y is S, G$_1$ is phenyl or substituted phenyl, n and m are each 1, R$_5$ is methyl, G$_2$ is

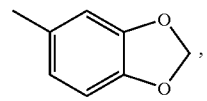

and R$_1$, R$_2$, R$_3$, R$_4$, X$_2$, and X$_4$ are as defined above for Formula I.

Still more preferred is a compound of Formula IV, or a pharmaceutically acceptable salt thereof, selected from:
 thiophene-2-carboxylic acid, 5-methyl-4-phenylacetylamino-, benzyl ester;
 thiophene-2-carboxylic acid, 5-methyl-4-phenylacetylamino-, benzyl amide;
 thiophene-2-carboxylic acid, 5-methyl-4-phenylacetylamino-, 1,3-benzodioxol-5-ylmethyl ester; and
 thiophene-2-carboxylic acid, 5-methyl-4-phenylacetylamino-, 1,3-benzodioxol-5-ylmethyl amide.

Another preferred embodiment of the present invention is a compound of Formula V

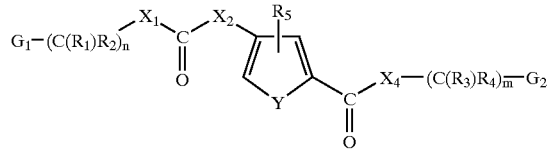

V

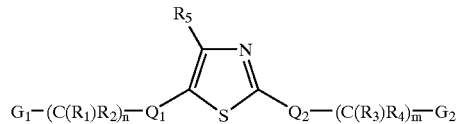

VI or a pharmaceutically acceptable salt thereof, wherein Y is O, S, or N—CH$_3$, and G$_1$, G$_2$, R$_1$, R$_2$, R$_3$, R$_4$, n, m, X$_1$, X$_2$, X$_4$, and R$_5$ are as defined above for Formula I.

More preferred is a compound of Formula V, or a pharmaceutically acceptable salt thereof, wherein Y is S, and G$_1$, G$_2$, R$_1$, R$_2$, R$_3$, R$_4$, n, m, X$_1$, X$_2$, X$_4$, and R$_5$ are as defined above for Formula I.

Still more preferred is a compound of Formula V, or a pharmaceutically acceptable salt thereof, wherein Y is S, G$_1$ is phenyl or substituted phenyl, G$_2$ is phenyl, substituted phenyl, or C$_1$–C$_{12}$ alkyl, and R$_1$, R$_2$, R$_3$, R$_4$, X$_1$, X$_2$, X$_4$, and R$_5$ are as defined above for Formula I.

Still more preferred is a compound of Formula V, or a pharmaceutically acceptable salt thereof, wherein Y is S, G$_1$ is phenyl or substituted phenyl, G$_2$ is phenyl, substituted phenyl, or C$_1$–C$_{12}$ alkyl, n and m are each 1, and R$_1$, R$_2$, R$_3$, R$_4$, X$_1$, X$_2$, X$_4$, and R$_5$ are as defined above for Formula I.

Still more preferred is a compound of Formula V, or a pharmaceutically acceptable salt thereof, wherein Y is S, G$_1$ is phenyl or substituted phenyl, wherein the substituents are selected from 1,2-methylenedioxy, methoxy, ethoxy, —O—C(O)CH$_3$, carboxy, carbomethoxy, and carboethoxy, G$_2$ is phenyl, substituted phenyl, wherein the substituents are selected from 1,2-methylenedioxy, methoxy, ethoxy, —O—C(O)CH$_3$, carboxy, carbomethoxy, and carboethoxy, or C$_1$–C$_{12}$ alkyl, n and m are each 1, and R$_1$, R$_2$, R$_3$, R$_4$, X$_1$, X$_2$, X$_4$, and R$_5$ are as defined above for Formula I.

Still more preferred is a compound of Formula V, or a pharmaceutically acceptable salt thereof, wherein Y is S, G$_1$ is phenyl, G$_2$ is methyl or

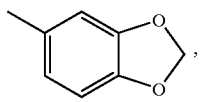

n and m are each 1, R$_5$ is methyl, and R$_1$, R$_2$, R$_3$, R$_4$, X$_1$, X$_2$, and X$_4$ are as defined above for Formula I.

Still more preferred is a compound of Formula V, or a pharmaceutically acceptable salt thereof, selected from:

thiophene-2-carboxylic acid, 4-(3-benzyl-ureido)-5-methyl-, methyl ester;

thiophene-2-carboxylic acid, 4-(3-benzyl-ureido)-5-methyl-, methyl amide;

thiophene-2-carboxylic acid, 4-(3-benzyl-ureido)-5-methyl-, benzyl ester;

thiophene-2-carboxylic acid, 4-(3-benzyl-ureido)-5-methyl-, benzyl amide;

thiophene-2-carboxylic acid, 4-(3-benzyl-ureido)-5-methyl-, (1,3-benzodioxol-5-ylmethyl)ester; and thiophene-2-carboxylic acid, 4-(3-benzyl-ureido)-5-methyl-, (1,3-benzodioxol-5-ylmethyl)amide.

Another embodiment of the present invention is a compound of Formula VI or a pharmaceutically acceptable salt thereof, wherein G$_1$, G$_2$, R$_1$, R$_2$, R$_3$, R$_4$, R$_5$, n, m, Q$_1$, and Q$_2$ are as defined above for Formula I.

Another embodiment of the present invention is a compound of Formula VI, or a pharmaceutically acceptable salt thereof, which is 3-methoxy-cyclopentanecarboxylic acid 5-(2-naphthalen-2-yl-ethylcarbamoyl)-4-phenyl-thiazol-2-yl ester.

Another embodiment of the present invention is a compound of Formula VII

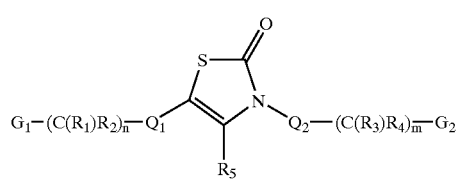

VII or a pharmaceutically acceptable salt thereof, wherein G$_1$, G$_2$, R$_1$, R$_2$, R$_3$, R$_4$, R$_5$, n, m, Q$_1$, and Q$_2$ are as defined above for Formula I.

Another embodiment of the present invention is a compound of Formula VII, or a pharmaceutically acceptable salt thereof, which is [2-(1H-indol-3-yl)-2-oxo-ethyl]-carbamic acid 3-(3-methyl-but-2-enylcarbamoyl)-2-oxo-2,3-dihydro-thiazol-5-yl ester.

Another embodiment of the present invention is a compound of Formula VIIIa

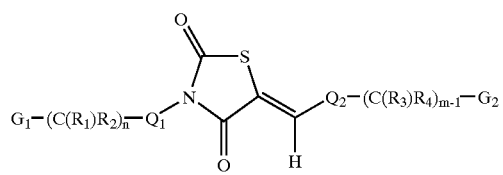

VIIIa or a pharmaceutically acceptable salt thereof, or a compound of Formula VIIIb

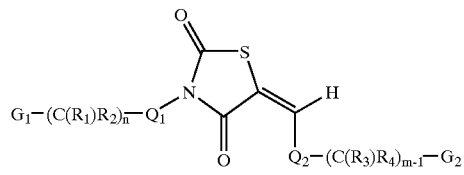

VIIIb or a pharmaceutically acceptable salt thereof, wherein G$_1$, G$_2$, R$_1$, R$_2$, R$_3$, R$_4$, R$_5$, n, m, Q$_1$, and Q$_2$ are as defined above for Formula I.

Another embodiment of the present invention is a compound of Formula VIIIa or VIIIb, or a pharmaceutically acceptable salt thereof, which is (Z)-5-(2,2-difluoro-hex-5-ynoyloxymethylene)-2,4-dioxo-thiazolidine-3-carboxylic acid 5-chloro-thiophen-2-ylmethyl ester or (E)-5-(2,2- difluoro-hex-5-ynoyloxymethylene)-2,4-dioxo-thiazolidine-3-carboxylic acid 5-chloro-thiophen-2-ylmethyl ester, respectively.

Another embodiment of the present invention is a compound of Formula IX

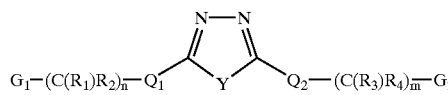

IX or a pharmaceutically acceptable salt thereof, wherein Y, $G_1$, $G_2$, $R_1$, $R_2$, $R_3$, $R_4$, n, m, $Q_1$, and $Q_2$ are as defined above for Formula I.

More preferred is a compound of Formula IX, or a pharmaceutically acceptable salt thereof, wherein Y is S and $G_1$, $G_2$, $R_1$, $R_2$, $R_3$, $R_4$, n, m, $Q_1$, and $Q_2$ are as defined above for Formula I.

Still more preferred is a compound of Formula IX, or a pharmaceutically acceptable salt thereof, wherein Y is S and $G_1$ and $G_2$ are independently phenyl or substituted phenyl, and $R_1$, $R_2$, $R_3$, $R_4$, n, m, $Q_1$, and $Q_2$ are as defined above for Formula I.

Still more preferred is a compound of Formula IX, or a pharmaceutically acceptable salt thereof, wherein Y is S, $G_1$ and $G_2$ independently are phenyl or substituted phenyl, n and m are each 1, and $R_1$, $R_2$, $R_3$, $R_4$, $Q_1$, and $Q_2$ are as defined above for Formula I.

Still more preferred is a compound of Formula IX named 5-(3-benzyl-ureido)-1,3,4-thiadiazole-2-carboxylic acid benzyl ester, or a pharmaceutically acceptable salt thereof.

A further embodiment of this invention is a pharmaceutical composition, comprising a compound of Formula I, or a pharmaceutically acceptable salt thereof, in admixture with a pharmaceutically acceptable carrier, excipient, or diluent. Preferred compositions comprise a compound of Formulas II, III, IV, V, VI, VII, VIIIa, or VIIIb. Other preferred compositions comprise a compound of Formula IX.

Another embodiment of this invention is a method of treating a patient that has a disease mediated by MMP-13 and optionally from 0 to 15 additional MMP enzymes, comprising administering to said patient a therapeutically effective amount of a pharmaceutical composition which comprises a compound of Formula I, or a pharmaceutically acceptable salt thereof, in admixture with a pharmaceutically acceptable carrier, excipient, or diluent. Preferred methods administer a pharmaceutical composition which comprises a compound of Formulas II, III, IV, V, VI, VII, VIIIa, or VIIIb. Other preferred methods administer a pharmaceutical composition which comprises a compound of Formula IX.

Another embodiment of this invention is a method for inhibiting MMP-13, comprising administering to a patient in need thereof an MMP-13 inhibiting amount of a compound of Formula I, or a pharmaceutically acceptable salt thereof. Preferred methods administer a compound of Formulas II, III, IV, V, VI, VII, VIIIa, or VIIIb. Other preferred methods administer a compound of Formula IX.

Another embodiment of this invention is a method of preventing connective tissue or extracellular matrix degradation mediated by MMP-13 and optionally from 0 to 15 additional MMP enzymes, comprising administering to a patient in need of thereof an MMP-13 inhibiting amount of a compound of Formula I, or a pharmaceutically acceptable salt thereof. Preferred methods of preventing administer a compound of Formulas II, III, IV, V, VI, VII, VIIIa, or VIIIb. Other preferred methods of preventing administer a compound of Formula IX.

Preferred is a method of preventing connective tissue or extracellular matrix degradation mediated by MMP-13 and optionally from 0 to 15 additional MMP enzymes, comprising administering to a patient in need thereof an MMP-13 inhibiting amount of a compound of Formula I, or a pharmaceutically acceptable salt thereof, wherein the patient being treated is at risk for, or has, a disease selected from: cancer, especially breast carcinoma, inflammation, heart failure, asthma, cancer metastasis, multiple sclerosis, corneal epidermal ulceration, gastric ulceration, stroke, renal disease, macular degeneration, atherosclerosis, neointimal proliferation, osteoporosis, periodontitis, gingivitis, an autoimmune disease, a hyper-immune disease, and arthritis, including osteoarthritis and rheumatoid arthritis.

Another preferred method of preventing according to this invention is prevention of connective tissue or extracellular matrix degradation in a patient at risk for, or has, an autoimmune disease.

Another preferred method of preventing according to this invention is prevention of connective tissue or extracellular matrix degradation in a patient at risk for, or has, a hyper-immune disease.

Another preferred method of preventing according to this invention is prevention of connective tissue or extracellular matrix degradation in a patient at risk for, or has, cancer.

Another preferred method of preventing according to this invention is prevention of connective tissue or extracellular matrix degradation in a patient at risk for, or has, cancer, which cancer is a breast carcinoma.

Another preferred method of preventing according to this invention is prevention of connective tissue or extracellular matrix degradation in a patient at risk for, or has, inflammation.

Another preferred method of preventing according to this invention is prevention of connective tissue or extracellular matrix degradation in a patient at risk for, or has, heart failure.

Another preferred method of preventing according to this invention is prevention of connective tissue or extracellular matrix degradation in a patient at risk for, or has, rheumatoid arthritis.

Another preferred method of preventing according to this invention is prevention of connective tissue or extracellular matrix degradation in a patient at risk for, or has, osteoarthritis.

Another preferred method of preventing according to this invention is prevention of connective tissue or extracellular matrix degradation in a patient at risk for, or has, asthma.

Another preferred method of preventing according to this invention is prevention of connective tissue or extracellular matrix degradation in a patient at risk for, or has, osteoporosis.

Another preferred method of preventing according to this invention is prevention of connective tissue or extracellular matrix degradation in a patient at risk for, or has, multiple sclerosis.

Another preferred method of preventing according to this invention is prevention of connective tissue or extracellular matrix degradation in a patient at risk for, or has, cancer metastasis.

A further embodiment is a method of treating a patient that has a disease mediated by MMP-13 enzymes and optionally from 0 to 15 additional MMP enzymes, comprising administering to said patient a therapeutically effective amount of a compound of Formula I, or a pharmaceutically acceptable salt thereof. Preferred methods administer a compound of Formulas II, III, IV, V, VI, VII, VIIIa, or VIIIb. Other preferred methods administer a compound of Formula IX.

A preferred method of treating according to this invention is treatment of a patient that has a disease selected from cancer, especially breast carcinoma, inflammation, and heart failure. Other preferred methods of treating according to this invention include treatment of a patient that has asthma, cancer metastasis, multiple sclerosis, osteoporosis, an autoimmune disease, a hyper-immune disease, arthritis, including osteoarthritis and rheumatoid arthritis, periodontitis, gingivitis, corneal epidermal ulceration, gastric ulceration, stroke, renal disease, macular degeneration, atherosclerosis, or neointimal proliferation.

Another preferred method of treating according to this invention is treatment of a patient that has an autoimmune disease.

Another preferred method of treating according to this invention is treatment of a patient that has a hyper-immune disease.

Another preferred method of treating according to this invention is treatment of a patient that has cancer.

Another preferred method of treating according to this invention is treatment of a patient that has cancer, wherein the cancer is a breast carcinoma.

Another preferred method of treating according to this invention is treatment of a patient that has inflammation.

Another preferred method of treating according to this invention is treatment of a patient that has heart failure.

Another preferred method of treating according to this invention is treatment of a patient that has rheumatoid arthritis.

Another preferred method of treating according to this invention is treatment of a patient that has osteoarthritis.

Another preferred method of treating according to this invention is treatment of a patient that has asthma Another preferred method of treating according to this invention is treatment of a patient that has osteoporosis.

Another preferred method of treating according to this invention is treatment of a patient that has multiple sclerosis.

Another preferred method of treating according to this invention is treatment of a patient that has cancer metastasis.

Another embodiment of the present invention is a pharmaceutical composition, comprising a means for inhibiting MMP-13 and a pharmaceutically acceptable carrier, diluent, or excipient.

Still another embodiment of the present invention is an inhibitor of MMP-13, comprising an inhibitor of MMP-13 of Formula I

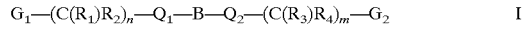

or a pharmaceutically acceptable salt thereof, wherein:

$G_1$ and $G_2$ are independently selected from:
hydrogen,
$C_1$–$C_{12}$ alkyl,
substituted $C_1$–$C_{12}$ alkyl,
$C_2$–$C_{12}$ alkenyl,
substituted $C_2$–$C_{12}$ alkenyl,
$C_2$–$C_{12}$ alkynyl,
substituted $C_2$–$C_{12}$ alkynyl,
$C_3$–$C_{12}$ cycloalkyl,
substituted $C_3$–$C_{12}$ cycloalkyl,
phenyl,
substituted phenyl,
naphthyl,
substituted naphthyl,
heteroaryl, and
substituted heteroaryl;

$R_1$, $R_2$, $R_3$, and $R_4$ are independently, at each occurrence, selected from:
hydrogen,
methyl,
cyano, and
fluoro, or $R_1$ and $R_2$, or $R_3$ and $R_4$, may be taken together with the carbon atom to which they are each attached to form C=O;

n and m are independently an integer of from 1 to 3;

$Q_1$ is $X_1$—C(=O)—, —C(=O)—$X_2$, or $X_1$—C(=O)—$X_2$, wherein $X_1$ and $X_2$ are independently O or N(H);

$Q_2$ is $X_3$—C(=O)—, —C(=O)—$X_4$, or $X_3$—C(=O)—$X_4$, wherein $X_3$ and $X_4$ are independently O or N(H); and B is a 5-membered heterocyclene selected from:

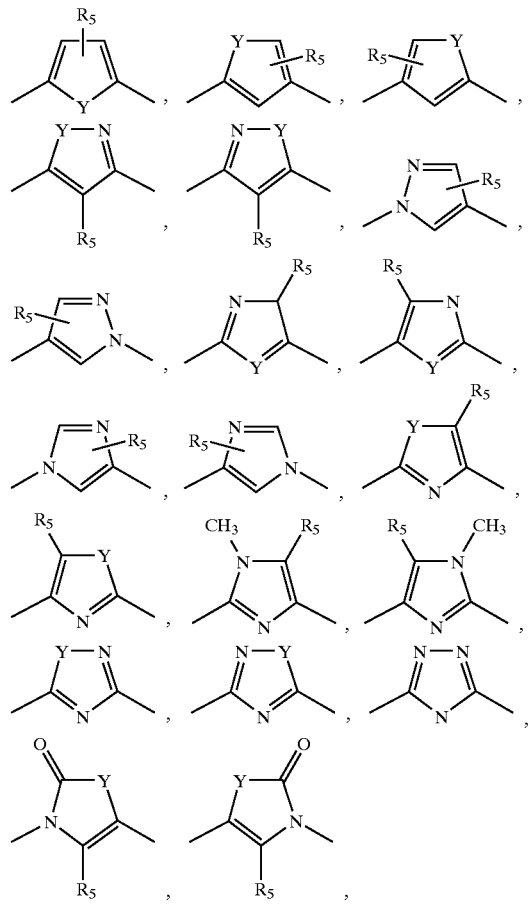

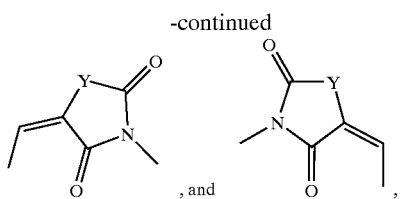

wherein Y is O, S, or N—CH$_3$, and
R$_5$ is selected from:
  hydrogen,
  C$_1$–C$_{12}$ alkyl,
  substituted C$_1$–C$_{12}$ alkyl,
  C$_2$–C$_{12}$ alkenyl,
  substituted C$_2$–C$_{12}$ alkenyl,
  C$_2$–C$_{12}$ alkynyl,
  substituted C$_2$–C$_{12}$ alkynyl,
  C$_3$–C$_{12}$ cycloalkyl,
  substituted C$_3$–C$_{12}$ cycloalkyl,
  phenyl,
  substituted phenyl,
  benzyl,
  substituted benzyl,
  O—R$_6$, wherein R$_6$ is hydrogen, C$_1$–C$_{12}$ alkyl, phenyl, or benzyl,
  S—R$_6$, wherein R$_6$ is hydrogen, C$_1$–C$_{12}$ alkyl, phenyl, or benzyl,
  C(O)—R$_6$, wherein R$_6$ is hydrogen, C$_1$–C$_{12}$ alkyl, phenyl, or benzyl,
  CO$_2$R$_6$, wherein R$_6$ is hydrogen, C$_1$–C$_{12}$ alkyl, phenyl, or benzyl,
  C(O)—N(H)OR$_6$, wherein R$_6$ is hydrogen, C$_1$–C$_{12}$ alkyl, phenyl, or benzyl,
  C(=NOR$_6$)—H, wherein R$_6$ is hydrogen, C$_1$–C$_{12}$ alkyl, phenyl, or benzyl,
  C(=NOR$_6$)—CH$_3$, wherein R$_6$ is hydrogen, C$_1$–C$_{12}$ alkyl, phenyl, or benzyl,
  CH$_2$OR$_6$, wherein R$_6$ is hydrogen, C$_1$–C$_{12}$ alkyl, phenyl, or benzyl,
  CH$_2$N(R$_6$)R$_7$, wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A)

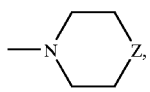

(A), wherein Z is CH$_2$, O, S, or N—R, wherein R is H or CH$_3$,
  C(H)F—OH,
  CF$_2$—OH,
  O—C(O)—R$_6$, wherein R$_6$ is hydrogen, C$_1$–C$_{12}$ alkyl, phenyl, or benzyl,
  C(O)—N(R$_6$)R$_7$, wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
  N(R$_6$)R$_7$, wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
  N(R$_6$)—C(O)—R$_7$, wherein R$_6$ and R$_7$ are independently hydrogen, C$_1$–C$_{12}$ alkyl, phenyl, or benzyl,
  N(H)—C(O)—N(R$_6$)R$_7$, wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
  N(H)—C(O)—OR$_6$, wherein R$_6$ is independently hydrogen, C$_1$–C$_{12}$ alkyl, phenyl, or benzyl,
  N(H)—S(O)$_2$—(C$_1$–C$_{12}$ alkyl),
  O—C(O)—N(R$_6$)R$_7$, wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
  NO$_2$,
  N$_3$,
  N(H)—C(NR$_8$)—N(R$_6$)R$_7$, wherein R$_6$ and R$_7$ are independently hydrogen, C$_1$–C$_4$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and R$_8$ is hydrogen, hydroxy, methoxy, or CN,
  CN,
  halo,
  S(O)—(C$_1$–C$_{12}$ alkyl),
  S(O)$_2$—(C$_1$–C$_{12}$ alkyl),
  S(O)$_2$—N(R$_6$)—(R$_7$), wherein R$_6$ and R$_7$ are independently hydrogen, C$_1$–C$_{12}$ alkyl, phenyl, or benzyl, or R$_6$ and R$_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and
  S(O)$_2$CF$_3$, wherein at least one of R$_1$, R$_2$, R$_3$, R$_4$, or R$_5$ is not hydrogen, or at least one of G$_1$ or G$_2$ is substituted C$_1$–C$_{12}$ alkyl, substituted C$_2$–C$_{12}$ alkenyl, substituted C$_2$–C$_{12}$ alkynyl, substituted C$_3$–C$_{12}$ cycloalkyl, substituted phenyl, substituted naphthyl, or substituted heteroaryl.

Preferred is the inhibitor of MMP-13 wherein the inhibitor selectively inhibits MMP-13 over MMP-1.
Also preferred is the inhibitor of MMP-13 wherein the inhibitor selectively inhibits MMP-13 over MMP-2.
Also preferred is the inhibitor of MMP-13 wherein the inhibitor selectively inhibits MMP-13 over MMP-3.
Also preferred is the inhibitor of MMP-13 wherein the inhibitor selectively inhibits MMP-13 over MMP-7.
Also preferred is the inhibitor of MMP-13 wherein the inhibitor selectively inhibits MMP-13 over MMP-8.

Also preferred is the inhibitor of MMP-13 wherein the inhibitor selectively inhibits MMP-13 over MMP-9.

Also preferred is the inhibitor of MMP-13 wherein the inhibitor selectively inhibits MMP-13 over MMP-10.

Also preferred is the inhibitor of MMP-13 wherein the inhibitor selectively inhibits MMP-13 over MMP-11.

Also preferred is the inhibitor of MMP-13 wherein the inhibitor selectively inhibits MMP-13 over MMP-12.

Also preferred is the inhibitor of MMP-13 wherein the inhibitor selectively inhibits MMP-13 over MMP-14.

Also preferred is the inhibitor of MMP-13 wherein the inhibitor selectively inhibits MMP-13 over MMP-15.

Also preferred is the inhibitor of MMP-13 wherein the inhibitor selectively inhibits MMP-13 over MMP-16.

Also preferred is the inhibitor of MMP-13 wherein the inhibitor selectively inhibits MMP-13 over MMP-17.

Also preferred is the inhibitor of MMP-13 wherein the inhibitor selectively inhibits MMP-13 over MMP-18.

Also preferred is the inhibitor of MMP-13 wherein the inhibitor selectively inhibits MMP-13 over MMP-19.

Also preferred is the inhibitor of MMP-13 wherein the inhibitor selectively inhibits MMP-13 over TNF-α converting enzyme.

DETAILED DESCRIPTION OF THE INVENTION

This invention provides a compound of Formula I

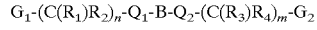

$$G_1-(C(R_1)R_2)_n-Q_1-B-Q_2-(C(R_3)R_4)_m-G_2 \qquad I$$

or a pharmaceutically acceptable salt thereof, wherein $G_1$, $G_2$, $R_1$, $R_2$, $R_3$, $R_4$, n, m, $Q_1$, $Q_2$, and B are as defined above for Formula I.

If n=m=0 and $G_1$ and $G_2$ are phenyl or substituted phenyl, the compounds are not selective inhibitors of MMP-13, and are not part of the instant invention compounds.

As used herein, the term "$C_1$–$C_{12}$ alkyl" means a straight or branched, unsubstituted hydrocarbon group having from 1 to 12 carbon atoms. Preferred $C_1$–$C_{12}$ alkyl groups are $C_1$–$C_6$ alkyl. Typical examples of $C_1$–$C_{12}$ alkyl groups include methyl, ethyl, 1-propyl, 2-propyl, 1-butyl, 2-butyl, 2,2-dimethylethyl, 1-pentyl, 2-pentyl, 2,2-dimethylpropyl, and 1-hexyl, which are all also $C_1$–$C_6$ alkyl groups, and 1-heptyl, 4-heptyl, 2-octyl, 2-methyl-hept-2-yl, 1-nonyl, 1-decyl, 1-undecyl, 1-dodecyl, 2-dodecyl, 2,4-dimethyl-2-decyl, and 2-(1-methylethyl)-1-nonyl.

The phrase "substituted $C_1$–$C_{12}$ alkyl" means a straight or branched, hydrocarbon group having from 1 to 12 carbon atoms, which is substituted with from 1 to 4 substituents as described below. Illustrative examples of substituted $C_1$–$C_{12}$ alkyl are provided below.

The term "$C_1$–$C_4$ alkyl" means a straight or branched unsubstituted hydrocarbon group having from 1 to 4 carbon atoms. Illustrative $C_1$–$C_4$ alkyl groups include methyl, ethyl, 1-propyl, 2-propyl, 1-butyl, 2-butyl, and 1,1-dimethylethyl.

The term "$C_2$–$C_{12}$ alkenyl" means a straight or branched, unsubstituted hydrocarbon group having from 2 to 12 carbon atoms and 1 or 2 sites of unsaturation (i.e., 1 or 2 C═C bonds). Preferred $C_2$–$C_{12}$ alkenyl groups are $C_2$–$C_6$ alkenyl. Typical examples of $C_2$–$C_{12}$ alkenyl groups include ethenyl, 1-propen-1-yl, 1-propen-2-yl, 2-propen-1-yl, 1-buten-3-yl, 2-penten-2-yl, and 1-hexen-6-yl, which are all also $C_2$–$C_6$ alkenyl groups, and 1-hepten-3-yl, 3-hepten-1-yl, 2-octen-6-yl, 2-methyl-hept-2-en-4-yl, 1-nonen-8-yl, 1-decen-1-yl, 1-undecen-5-yl, and 2,4-dimethyl-2-decen-1-yl.

The phrase "substituted $C_2$–$C_{12}$ alkenyl" means a straight or branched, hydrocarbon group having from 2 to 12 carbon atoms, and 1 or 2 sites of unsaturation (i.e., 1 or 2 C═C bonds), which is substituted with from 1 to 4 substituents as described below. Illustrative examples of substituted $C_2$–$C_{12}$ alkenyl are provided below.

The term "$C_2$–$C_{12}$ alkynyl" means a straight or branched, unsubstituted hydrocarbon group having from 2 to 12 carbon atoms and 1 or 2 sites of double unsaturation (i.e., 1 or 2 C≡C bonds). Preferred $C_2$–$C_{12}$ alkynyl groups are $C_2$–$C_6$ alkynyl. Typical examples of $C_2$–$C_{12}$ alkynyl groups include ethenyl, 1-propyn-1-yl, 1-propyn-3-yl, 1-butyn-3-yl, 2-pentyn-1-yl, and 1-hexyn-6-yl, which are all also $C_2$–$C_6$ alkynyl groups, and 1-heptyn-3-yl, 3-heptyn-1-yl, 2-octyn-6-yl, 2-methyl-hept-3-yn-5-yl, 1-nonyn-8-yl, 1-decyn-1-yl, 1-undecyn-5-yl, and 2,4-dimethyl-5-decyn-1-yl.

The phrase "substituted $C_2$–$C_{12}$ alkynyl" means a straight or branched, hydrocarbon group having from 2 to 12 carbon atoms, and 1 or 2 sites of unsaturation (i.e., 1 or 2 C≡C bonds), which is substituted with from 1 to 4 substituents as described below. Illustrative examples of substituted $C_2$–$C_{12}$ alkynyl are provided below.

The term "$C_3$–$C_6$ cycloalkyl" means an unsubstituted cyclic hydrocarbon group having from 3 to 6 carbon atoms. The group $C_3$–$C_6$ cycloalkyl includes cyclopropyl, cyclobutyl, cyclopentyl, and cyclohexyl.

The term "$C_3$–$C_{12}$ cycloalkyl" means an unsubstituted cyclic hydrocarbon group having from 3 to 12 carbon atoms. Preferred $C_3$–$C_{12}$ cycloalkyl groups are $C_3$–$C_6$ cycloalkyl. Illustrative examples of $C_3$–$C_{12}$ cycloalkyl groups are cyclopropyl, cyclobutyl, cyclopentyl, cyclohexyl, cycloheptyl, cyclooctyl, cyclononyl, cyclodecyl, cycloundecyl, and cyclododecyl.

The phrase "substituted $C_3$–$C_{12}$ cycloalkyl" means a cyclic hydrocarbon group having from 3 to 12 carbon atoms, which is substituted with from 1 to 4 substituents as described below. Illustrative examples of substituted $C_3$–$C_{12}$ cycloalkyl are provided below.

As described above, substituted $C_1$–$C_{12}$ alkyl, substituted $C_2$–$C_{12}$ alkenyl, substituted $C_2$–$C_{12}$ alkynyl, and substituted $C_3$–$C_{12}$ cycloalkyl are substituted with from 1 to 4 substituents. The substituents are independently selected from:

oxo,

O—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 3 substituents as described below, S—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, $CO_2R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—N(H)O$R_z$, wherein $R_z$ is hydrogen, $C_1$–$C_{12}$ alkyl, phenyl, or benzyl, C(═NO$R_z$)—H, wherein $R_z$ is hydrogen, $C_1$–$C_{12}$ alkyl, phenyl, or benzyl, C(═NO$R_z$)—CH$_3$, wherein $R_z$ is hydrogen, $C_1$–$C_{12}$ alkyl, phenyl, or benzyl,

C(H)F—OH,

O—C(O)—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z)

(Z)

wherein Y is CH$_2$, O, S, or N—R, wherein R is H or CH$_3$,

N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(R$_z$)—C(O)—R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, N(H)—C(O)—N(R$_z$)R$_y$, wherein R$_z$ and R$_y$ are independently hydrogen, C$_1$–C$_4$ alkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(H)—C(O)—OR$_z$, wherein R$_z$ is independently hydrogen, C$_1$–C$_4$ alkyl, C$_3$–C$_6$ cycloalkyl, phenyl, or benzyl, wherein phenyl and benzyl may be substituted with from 1 to 4 substituents as described below, O—C(O)—N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,

NO$_2$,

N$_3$,

N(H)—C(NR$_x$)—N(R$_z$)R$_y$, wherein R$_z$ and R$_y$ are independently hydrogen, C$_1$–C$_4$ alkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and R$_x$ is hydrogen, hydroxy, methoxy, or CN,

CN, halo,

S(O)—(C$_1$–C$_4$ alkyl),

S(O)$_2$—(C$_1$–C$_4$ alkyl),

S(O)$_2$—N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and N(H)—S(O)$_2$—(C$_1$–C$_4$ alkyl).

Illustrative examples of substituted C$_1$–C$_{12}$ alkyl groups include CH$_2$OH, CF$_2$OH, CH$_2$C(CH$_3$)$_2$CO$_2$CH$_3$, CF$_3$, C(O)CF$_3$, C(O)—CH$_3$, (CH$_2$)$_4$—S—CH$_3$, CH(CO$_2$H)CH$_2$CH$_2$C(O)NMe$_2$, (CH$_2$)$_5$NH—C(O)—NH$_2$, CH$_2$—CH$_2$—C(H)—(4-fluorophenyl), CH(OCH$_3$)CH$_2$CH$_3$, (CH$_2$)$_9$-(morpholin-4-yl), CH$_2$SO$_2$NH$_2$, and CH(CH$_3$)CH$_2$CH$_2$OC(O)CH$_3$.

Illustrative examples of substituted C$_2$–C$_{12}$ alkenyl groups include C(H)=C(H)CH$_2$OH, CH=CF$_2$, CH$_2$C(H)=C(H)—(CH$_2$)$_2$CF$_2$OH, CH$_2$C(=CH$_2$)CO$_2$CH$_3$, C(H)=C(H)—CF$_3$, CH$_2$—CH$_2$—C(H)=C(H)—C(O)—CH$_3$, C(H)=C(CH$_3$)—S—CH$_3$, C(H)=C(H)—C(H)=C(CH$_3$)—CO$_2$Me, (CH$_2$)$_{12}$—CH$_2$-phenyl, and C(H)=C=C(H)OC(O)CH$_3$.

Illustrative examples of substituted C$_2$–C$_{12}$ alkynyl groups include C≡CCH$_2$OH, C≡CF, CH$_2$C≡C—(CH$_2$)$_2$CF$_2$OH, C≡C—CH$_2$CO$_2$CH$_3$, CH$_2$C≡C—CF$_3$, CH$_2$—CH$_2$—C≡C—C(O)—CH$_3$, C≡C—S—CH$_3$, and C≡C—C(O)OC(O)CH$_3$.

Illustrative examples of substituted C$_3$–C$_{12}$ cycloalkyl groups include 1-hydroxy-cyclopropyl, cyclobutanon-3-yl, 3-(3-phenyl-ureido)-cyclopent-1-yl, 4-carboxy-cyclohexyl, and 9-trifluromethyl-cyclododecanyl.

The phrase "5-membered heterocyclene" means a 5-membered, monocyclic, aromatic or pseudo aromatic ring diradical, wherein two of the five ring atoms each bear a radical, having carbon atoms, which carbon atoms may be unsubstituted or substituted with oxo or the group R$_5$, wherein R$_5$ is as defined above, and from 1 to 3 heteroatoms selected from N, O, and S, with the provisos that (i) each of the two ring atoms bearing a radical are not directly bonded to each other and (ii) not more than 1 heteroatom atom which is O or S is present.

Illustrative examples of unsubstituted 5-membered heterocyclene include thiophen-2,5-diyl, furan-2,4-diyl, pyrrol-3,5-diyl, pyrrol-1,3-diyl, imidazol-1,4-diyl, isoxazol-3,5-diyl, oxazol-2,4-diyl, thiazol-2,5-diyl, 1,2,4-oxadiazol-3,5-diyl, 1,2,4-triazol-1,3-diyl, and pyrazol-1,3-diyl.

Illustrative examples of substituted 5-membered heterocyclene include 3-methyl-thiophen-2,5-diyl, 3-carbomethoxy-furan-2,4-diyl, 1-benzyl-pyrrol-3,5-diyl, 2-chloro-imidazol-1,4-diyl, 4-cyano-isoxazol-3,5-diyl, 5-methoxy-oxazol-2,4-diyl, 4-acetyl-thiazol-2,5-diyl, and 5-imino-pyrazol-1,3-diyl.

The phrase "substituted phenyl" means phenyl substituted with from 1 to 4 substituents as described below. Illustrative examples of substituted phenyl are provided below.

The phrase "substituted benzyl" means a substituted phenyl, wherein substituted phenyl is as described above, bonded through a CH$_2$ group. Illustrative examples of substituted benzyl are provided below.

The term "naphthyl" includes 1-naphthyl and 2-napthyl.

The phrase "substituted naphthyl" means substituted 1-naphthyl or substituted 2-naphthyl, each substituted with from 1 to 4 substituents as described below. Illustrative examples of substituted naphthyl are provided below.

The term "heteroaryl" means a 5-membered, monocyclic heteroaryl, a 6-membered, monocyclic heteroaryl, or a 9- or 10-membered, fused-bicyclic heteroaryl, which are as defined below:

(i) The phrase "5-membered, monocyclic heteroaryl" means a 5-membered, monocyclic, aromatic ring group having carbon atoms and from 1 to 4 heteroatoms selected from N, O, and S, with the proviso that not more than 1 heteroatom atom which is O or S is present;

(ii) The phrase "6-membered, monocyclic heteroaryl" means a 6-membered, monocyclic, aromatic ring group having carbon atoms and 1 or 2 nitrogen atoms; and (iii) The phrase "9- or 10-membered, fused-bicyclic heteroaryl" means a 9-membered or 10-membered, aromatic, fused-bicyclic ring group having carbon atoms and from 1 to 4 heteroatoms selected from N, O, and S, with the proviso that not more than 2 heteroatoms which are oxygen atoms and/or sulfur atoms are present, and further that when 2 heteroatoms which are O and/or S are present, the oxygen atoms and/or sulfur atoms are not bonded to each other.

Illustrative examples of a 5-membered, monocyclic heteroaryl include thiophen-2-yl, furan-2-yl, pyrrol-3-yl, pyrrol-1-yl, imidazol-4-yl, isoxazol-3-yl, oxazol-2-yl, thiazol-4-yl, tetrazol-1-yl, 1,2,4-oxadiazol-3-yl, 1,2,4-triazol-1-yl, and pyrazol-3-yl. Substituted 5-membered, monocyclic heteroaryl is described below.

Illustrative examples of a 6-membered, monocyclic heteroaryl include pyridin-2-yl, pyridin-4-yl, pyrimidin-2-yl, pyridazin-4-yl, and pyrazin-2-yl. Substituted 6-membered, monocyclic heteroaryl is described below.

Illustrative examples of a 9- or 10-membered, fused-bicyclic heteroaryl include indol-2-yl, indol-6-yl, iso-indol-2-yl, benzimidazol-2-yl, benzimidazol-1-yl, benztriazol-1-yl, benztriazol-5-yl, quinolin-2-yl, isoquinolin-7-yl, benzopyrimidin-2-yl, benzoxazol-2-yl, benzothiophen-5-yl, and benzofuran-3-yl. Substituted 9- or 10-membered, bicyclic heteroaryl is described below.

The phrase "substituted heteroaryl" means a substituted 5-membered, monocyclic heteroaryl, a substituted 6-membered, monocyclic heteroaryl, or a substituted 9- or 10-membered, fused-bicyclic heteroaryl, which are as defined below:

(i) The phrase "substituted 5-membered, monocyclic heteroaryl" means a 5-membered, monocyclic, aromatic ring group having carbon atoms and from 1 to 4 heteroatoms selected from N, O, and S, which is substituted with 1 or 2 substituents as defined below, with the proviso that not more than 1 heteroatom atom which is O or S is present, and further that each substituent is not bonded to an oxygen atom or a sulfur atom;

(ii) The phrase "substituted 6-membered, monocyclic heteroaryl" means a 6-membered, monocyclic, aromatic ring group having carbon atoms and 1 or 2 nitrogen atoms, which is substituted with 1 or 2 substituents as defined below, with the proviso that each substituent is not bonded to a nitrogen atom; and (iii) The phrase "substituted 9- or 10-membered, fused-bicyclic heteroaryl" means a 9-membered or 10-membered, fused-bicyclic, aromatic ring group having carbon atoms and from 1 to 4 heteroatoms selected from N, O, and S, which is substituted with from 1 to 3 substituents as defined below, with the proviso that not more than 2 heteroatoms which are O and/or S are present, and further that when 2 heteroatoms which are O and/or S atoms are present, the O and/or S atoms are not bonded to each other, and further that each substituent is not bonded to an oxygen atom or a sulfur atom.

Illustrative examples of a substituted, 5-membered, monocyclic heteroaryl, substituted, 6-membered, monocyclic heteroaryl, and substituted 9- or 10-membered, fused-bicyclic heteroaryl are provided below.

The substituents for substituted phenyl, substituted benzyl, substituted naphthyl (i.e., substituted 1-naphthyl or substituted 2-naphthyl), substituted 5-membered, monocyclic heteroaryl, substituted 6-membered, monocyclic heteroaryl, and substituted 9- or 10-membered, fused-bicyclic heteroaryl are independently selected from:

$C_1$–$C_{12}$ alkyl, $C_2$–$C_{12}$ alkenyl, $C_2$–$C_{12}$ alkynyl, $C_3$–$C_{12}$ cycloalkyl, phenyl, benzyl, O—$R_z$, wherein $R_z$ is hydrogen, $C_1$–$C_{12}$ alkyl, phenyl, or benzyl, S—$R_z$, wherein $R_z$ is hydrogen, $C_1$–$C_{12}$ alkyl, phenyl, or benzyl, 1,2-methylenedioxy, C(O)—$R_z$, wherein $R_z$ is hydrogen, $C_1$–$C_{12}$ alkyl, phenyl, or benzyl, $CO_2R_z$, wherein $R_z$ is hydrogen, $C_1$–$C_{12}$ alkyl, phenyl, or benzyl, C(O)—N(H)O$R_z$, wherein $R_z$ is hydrogen, $C_1$–$C_{12}$ alkyl, phenyl, or benzyl, C(=NO$R_z$)—H, wherein $R_z$ is hydrogen, $C_1$–$C_{12}$ alkyl, phenyl, or benzyl, C(=NO$R_z$)—$CH_3$, wherein $R_z$ is hydrogen, $C_1$–$C_{12}$ alkyl, phenyl, or benzyl, $CH_2OR_z$, wherein $R_z$ is hydrogen, $C_1$–$C_{12}$ alkyl, phenyl, or benzyl, $CH_2N(R_z)R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,

C(H)F—OH, $CF_2$—OH,

O—C(O)—$R_z$, wherein $R_z$ is hydrogen, $C_1$–$C_{12}$ alkyl, phenyl, or benzyl, C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(R$_z$)—C(O)—R$_y$, wherein R$_z$ and R$_y$ are independently hydrogen, C$_1$–C$_{12}$ alkyl, phenyl, or benzyl, N(H)—C(O)—N(R$_z$)R$_y$, wherein R$_z$ and R$_y$ are independently hydrogen, C$_1$–C$_{12}$ alkyl, phenyl, or benzyl, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(H)—C(O)—OR$_z$, wherein R$_z$ is independently hydrogen, C$_1$–C$_{12}$ alkyl, phenyl, or benzyl, N(H)—S(O)$_2$—(C$_1$–C$_{12}$ alkyl), O—C(O)—N(R$_z$)R$_y$, wherein R$_z$ and R$_y$ are independently hydrogen, C$_1$–C$_{12}$ alkyl, phenyl, or benzyl, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,

NO$_2$,

N$_3$,

N(H)—C(NR$_x$)—N(R$_z$)R$_y$, wherein R$_z$ and R$_y$ are independently hydrogen, C$_1$–C$_4$ alkyl, phenyl, or benzyl, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and R$_x$ is hydrogen, hydroxy, methoxy, or CN,

CN, halo,

S(O)—(C$_1$–C$_{12}$ alkyl),

S(O)$_2$—(C$_1$–C$_{12}$ alkyl),

S(O)$_2$—N(R$_z$)—(R$_y$), wherein R$_z$ and R$_y$ are independently hydrogen, C$_1$–C$_{12}$ alkyl, phenyl, or benzyl, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and

S(O)$_2$CF$_3$.

Preferred substituents for substituted phenyl, substituted benzyl, substituted naphthyl (i.e., substituted 1-naphthyl or substituted 2-naphthyl), and preferred substituents at carbon atoms for substituted 5-membered, monocyclic heteroaryl, substituted 6-membered, monocyclic heteroaryl, and substituted 9- or 10-membered, fused-bicyclic heteroaryl are C$_1$–C$_4$ alkyl, halo, OH, O—C$_1$–C$_4$ alkyl, 1,2-methylenedioxy, CN, NO$_2$, N$_3$, NH$_2$, N(H)CH$_3$, N(CH$_3$)$_2$, C(O)CH$_3$, OC(O)—C$_1$–C$_4$ alkyl, C(O)—H, CO$_2$H, CO$_2$—(C$_1$–C$_4$ alkyl), C(O)—N(H)OH, C(O)NH$_2$, C(O)NHMe, C(O)N(Me)$_2$, NHC(O)CH$_3$, N(H)C(O)NH$_2$, SH, S—C$_1$–C$_4$ alkyl, C≡CH, C(=NOH)—H, C(=NOH)—CH$_3$, CH$_2$OH, CH$_2$NH$_2$, CH$_2$N(H)CH$_3$, CH$_2$N(CH$_3$)$_2$, C(H)F—OH, CF$_2$—OH, S(O)$_2$NH$_2$, S(O)$_2$N(H)CH$_3$, S(O)$_2$N(CH$_3$)$_2$, S(O)—CH$_3$, S(O)$_2$CH$_3$, S(O)$_2$CF$_3$, or NHS(O)$_2$CH$_3$.

Especially preferred substituents are 1,2-methylenedioxy, methoxy, ethoxy, —O—C(O)CH$_3$, carboxy, carbomethoxy, and carboethoxy.

Further as shown above, substituted 5-membered, monocyclic heteroaryl and substituted 9- or 10-membered, fused-bicyclic heteroaryl may optionally be substituted at a nitrogen atom, instead of a carbon atom, with 1 of certain substituents of said 1 or 2 substituents. Substitution at said nitrogen atom is possible when a ring —N(H)— group is present. The substituent replaces the hydrogen atom in the —N(H)— group and is selected from:

C$_1$–C$_{12}$ alkyl, which may be straight or branched,

C$_2$–C$_{12}$ alkenyl, which may be straight or branched,

C$_2$–C$_{12}$ alkynyl, which may be straight or branched,

C$_3$–C$_{12}$ cycloalkyl, phenyl, substituted phenyl, wherein substituted phenyl is as defined above, benzyl, substituted benzyl, wherein substituted benzyl is as defined above, C(O)—R$_z$, wherein R$_z$ is as defined above, CN, and S(O)$_2$—R$_z$, wherein R$_z$ is as defined above.

Illustrative examples of substituted 5-membered, monocyclic heteroaryl groups that are substituted at nitrogen include 1-methylimidazol-5-yl, 1-benzyl-pyrrol-2-yl, 1-acetyl-pyrazol-4-yl, 1-(4-fluorophenyl)-1,2,4-triazol-3-yl, and 2-decyl-tetrazol-5-yl.

Illustrative examples of substituted 9- or 10-membered, fused-bicyclic heteroaryl that may be substituted at nitrogen include 1-methylbenzimidazol-6-yl, 1-acetylbenztriazol-7-yl, 1-methanesulfonyl-indol-3-yl, 1-cyano-6-aza-indol-5-yl, and 1-(2,6-dichlorophenylmethyl)-benzpyrazol-3-yl.

Illustrative examples of:
(i) substituted phenyl include 4-methoxyphenyl, 2,6-difluorophenyl, 3-hydroxy-4-methylphenyl, 2-hydroxymethyl-3,4-dichloro-phenyl, 1,3-benzoxazol-5-yl, and 2-methoxy-4-nitrophenyl;

(ii) substituted 1-naphthyl include 5-trifluoromethanesulfonylaminonaphth-1-yl and 2-(N-hydroxy-carboxamido)-naphth-1-yl; and (iii) substituted 2-naphthyl includes 5-trifluoromethanesulfonylaminonaphth-2-yl and 1-(N-hydroxy-carboxamido)-naphth-2-yl.

Illustrative examples of:
(i) substituted 5-membered, monocyclic heteroaryl include 3-chloro-thiophen-2-yl, 5-hexyl-furan-2-yl, 1-methyl-pyrrol-3-yl, 2-carboxy-pyrrol-1-yl, 1,2-dimethyl-imidazol-4-yl, 5-(4-carboethoxy-7-fluoro-heptyl)-isoxazol-3-yl, 4-trifluoromethyl-oxazol-2-yl, 2-hydroxy-thiazol-4-yl, 5-acetylamino-tetrazol-1-yl, 5-(tert-butyl)-1,2,4-oxadiazol-3-yl, 3-cyano-1,2,4-triazol-1-yl, and 5-acetyl-pyrazol-3-yl;

(ii) substituted 6-membered, monocyclic heteroaryl include 4,6-difluoro-pyridin-2-yl, 2-methyl-pyridin-4-yl, 4-azido-pyrimidin-2-yl, 6-ureido-pyridazin-4-yl, and 5-methylthio-pyrazin-2-yl; and (iii) 9- or 10-membered, bicyclic heteroaryl include 6,7-dimethoxy-indol-2-yl, 1-propyl-indol-6-yl, 7-nitro-isoindol-2-yl, 1-benzyl-benzimidazol-2-yl, 4-chloro-benzimidazol-1-yl, 7-(2-propyl)-benztriazol-1-yl, 1-(2-hydroxyethyl)-benztriazol-5-yl, 4-iodo-quinolin-2-yl, 1-nitro-isoquinolin-7-yl, 4-cyano-benzopyrimidin-2-yl, 4,5,6-trifluoro-benzoxazol-2-yl, 2-carboxy-benzothiophen-5-yl, and 4-methylsulfinyl-benzofuran-3-yl.

The term "1,2-methylenedioxy" means the diradical group —O—CH$_2$—O—, wherein the substituent 1,2-methylenedioxy is bonded to adjacent carbon atoms of the group which is substituted to form a 5-membered ring. Illustrative examples of groups substituted by 1,2-methylenedioxy include 1,3-benzoxazol-5-yl of formula B

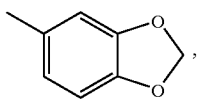

which is a phenyl group substituted by 1,2-methylenedioxy.

A fused-bicyclic group is a group wherein two ring systems share two, and only two, atoms.

It should be appreciated that the groups heteroaryl or heterocyclene may not contain two adjacent ring atoms which are oxygen and/or sulfur atoms.

The term "oxo" means =O. Oxo is attached at a carbon atom unless otherwise noted. Oxo, together with the carbon atom to which it is attached forms a carbonyl group (i.e., C=O).

The term "heteroatom" means N, O, or S.

The term "halo" means fluoro, chloro, bromo, or iodo.

The term "amino" means $NH_2$.

The phrase "tertiary organic amine" means a trisubstituted nitrogen group wherein the 3 substituents are independently selected from $C_1$–$C_{12}$ alkyl, $C_3$–$C_{12}$ cycloalkyl, benzyl, or wherein two of the substituents are taken together with the nitrogen atom to which they are attached to form a 5- or 6-membered, monocyclic heterocycle containing one nitrogen atom and carbon atoms, and the third substituent is selected from $C_1$–$C_{12}$ alkyl and benzyl, or wherein the three substituents are taken together with the nitrogen atom to which they are attached to form a 7- to 12-membered bicyclic heterocycle containing 1 or 2 nitrogen atoms and carbon atoms, and optionally a C=N double bond when 2 nitrogen atoms are present. Illustrative examples of tertiary organic amine include triethylamine, diisopropylethylamine, benzyl diethylamino, dicyclohexylmethyl-amine, 1,8-diazabicycle[5.4.0]undec-7-ene (DBU), 1,4-diazabicyclo[2.2.2]octane (TED), and 1,5-diazabicycle[4.3.0]non-5-ene.

The term "comprising," which is synonymous with the terms "including," "containing," or "characterized by," is inclusive or open-ended, and does not exclude additional, unrecited elements or method steps from the scope of the invention that is described following the term.

The phrase "consisting of" is closed-ended, and excludes any element, step, or ingredient not specified in the description of the invention that follows the phrase.

The phrase "consisting essentially of" limits the scope of the invention that follows to the specified elements, steps, or ingredients, and those further elements, steps, or ingredients that do not materially affect the basic and novel characteristics of the invention.

The phrase "pharmaceutical composition" means a composition suitable for administration in medical or veterinary use.

The phrase "in admixture" means in a state of being in a homogeneous or heterogeneous mixture. Preferred is a homogeneous mixture.

The term "patient" means a mammal. Preferred patients are humans, cats, dogs, cows, horses, pigs, and sheep.

The term "$IC_{50}$" means the concentration of test compound required to inhibit activity of a biological target, such as a receptor or enzyme, by 50%.

The phrase "autoimmune disease" means the diseases classified as "Highly probable" or "Probable" in Table 20-3. PUTATIVE AUTOIMMUNE DISORDERS of The Merck Manual of Diagnosis and Therapy, 16$^{th}$ edition, Robert Berkow ed., Merck Research Laboratories, Rahway, N.J., 1992:340, which is hereby incorporated herein by reference.

Diseases classified as highly probable include, to name a few, systemic lupus erythematosus, Grave's disease, myasthenia gravis, insulin resistance, and autoimmune hemolytic anemia. Diseases classified as probable include, to name a few, rheumatoid arthritis, scleroderma with anti-collagen antibodies (Abs), pernicious anemia, and some cases of diabetes mellitus.

The phrase "hyper-immune disease" means diseases which involve an inappropriate, especially excessive, immune response. These diseases include asthma.

The phrases "connective tissue degradation" and "connective tissue breakdown" are synonymous and mean the cleavage of the macromolecular components of connective tissue such as, for example, collagens or proteoglycans.

The phrase "connective tissue" means a tissue of mesodermal origin rich in intercellular substance or interlacing processes with little tendency for the cells to come together in sheets or masses, especially connective tissue of stellate or spindle-shaped cells with interlacing processes that pervades, supports, and binds together other tissues and forms ligaments, tendons, or aponeuroses.

The phases "extracellular matrix degradation" and extracellular matrix breakdown" are synonymous and may be used interchangeably with the phrases "connective tissue degradation" and "connective tissue breakdown."

An example of connective tissue or extracellular matrix is cartilage, which lines the surface of bone in joints. Other connective tissue or extracellular matrix tissue includes the tissue that binds the cells of the skin, cell lining blood vessels, and multi-cellular structures of the heart, kidney, lung, and other organs.

The phrases "effective amount" and "therapeutically effective amount" are synonymous and mean an amount of a compound of the present invention, or a pharmaceutically acceptable salt thereof, or a solvate thereof, sufficient to effect an improvement of the condition being treated when administered to a patient suffering from a disease that is mediated by MMP-13 and optionally from 0 to 12 additional MMP enzymes.

The term "(E)" means entgegen, and designates that the conformation about the double bond to which the term refers is the conformation having the two higher ranking substituent groups, as determined according to the Cahn-Ingold-Prelog ranking system, on opposite sides of the double bond. An (E) double bond is illustrated below by the compound of Formula (W)

wherein the two higher-ranking substituents are groups A and D.

The term "(Z)" means zusammen, and designates that the conformation about the double bond to which the term refers is the conformation having the two higher ranking substituent groups, as determined according to the Cahn-Ingold-Prelog ranking system, on the same side of the double bond. A (Z) double bond is illustrated below by the compound of Formula (X)

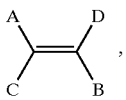 (X)

wherein the two higher-ranking substituents are groups A and D.

The phrase "pseudo aromatic" means similar to or derivable from an aromatic parent substance or tautomeric form thereof.

The phrase "inert atmosphere" means an atmosphere which consists essentially of nitrogen gas or argon gas, or mixtures thereof.

It should be appreciated that the matrix metalloproteinases include the following enzymes:

MMP-1, also known as interstitial collagenase, collagenase-1, or fibroblast-type collagenase;

MMP-2, also known as gelatinase A or 72 kDa Type IV collagenase;

MMP-3, also known as stromelysin or stromelysin-1;

MMP-7, also known as matrilysin or PUMP-1;

MMP-8, also known as neutrophil collagenase or polymorphonuclear-type ("PMN-type") collagenase;

MMP-9, also known as gelatinase B or 92 kDa Type IV collagenase;

MMP-10, also known as stromelysin-2;

MMP-11, also known as stromelysin-3;

MMP-12, also known as metalloelastase;

MMP-13, also known as collagenase-3;

MMP-14, also known as membrane-type ("MT") MMP-1 or MT-MMP-1;

MMP-15, also known as MT-MMP-2;

MMP-16, also known as MT-MMP-3;

MMP-17, also known as MT-MMP-4;

MMP-18; and

MMP-19.

As discussed above, one aspect of the present invention is novel compounds which are selective inhibitors of the enzyme MMP-13. A selective inhibitor of MMP-13, as used in the present invention, is a compound that is $\geq 10\times$more potent in vitro versus MMP-13 than versus at least one other matrix metalloproteinase enzyme such as, for example, MMP-1, MMP-2, MMP-3, MMP-7, MMP-8, MMP-9, or MMP-14, or versus TACE. A preferred aspect of the present invention is novel compounds which are selective inhibitors of MMP-13 versus TACE and/or MMP-1.

Some of the compounds of the present invention may exist as tautomeric forms, which interchange via, for example, enolization and the like. All tautomeric forms are within the scope of the present invention.

Some compounds of the present invention have chiral centers, in which case all stereoisomers thereof, both enantiomers, diastereomers, and mixtures thereof, are within the scope of the present invention.

Some compounds of the present invention have alkenyl groups, which may exist as entgegen or zusammen conformations, in which case all geometric forms thereof, both entgegen and zusammen, cis and trans, and mixtures thereof, are within the scope of the present invention.

Some compounds of the present invention have cycloalkyl groups, which may be substituted at more than one carbon atom, in which case all geometric forms thereof, both cis and trans, and mixtures thereof, are within the scope of the present invention.

The compounds to be used in the present invention can exist in unsolvated forms as well as solvated forms, including hydrated forms. In general, the solvated forms, including hydrated forms, are equivalent to unsolvated forms and are intended to be encompassed within the scope of the present invention.

The compounds of Formula I are capable of further forming pharmaceutically acceptable salts, including but not limited to acid addition and/or base salts.

Pharmaceutically acceptable acid addition salts of the compounds of Formula I include nontoxic salts derived from inorganic acids such as hydrochloric, nitric, phosphoric, sulfuric, hydrobromic, hydroiodic, phosphorus, and the like, as well as the nontoxic salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, malate, tartrate, methanesulfonate, and the like. Also contemplated are the salts of amino acids such as arginate, gluconate, galacturonate, and the like; see, for example, Berge et al., "Pharmaceutical Salts," *J. of Pharmaceutical Science,* 1977;66:1–19.

The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts include nontoxic salts formed with metal cations, such as alkali and alkaline earth metal cations, or with organic (i.e., substituted) ammonium cations. Examples of suitable metal cations include sodium ($Na^+$) cation, potassium ($K^+$) cation, magnesium ($Mg^{+2}$) cation, calcium ($Ca^{+2}$) cation, and the like. Examples of suitable organic amines are N,N'-dibenzylethylenediamine, chloroprocaine, choline, diethanolamine, ethylenediamine, N-methylglucamine, and procaine; see, for example, Berge et al., Supra., 1977.

The base addition salts of acidic compounds are prepared by contacting the free acid form with a sufficient amount of the desired base such as an alkali or alkaline earth metal hydroxide or an organic amine to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes of the present invention.

All of these forms, including the free acids, or free bases, pharmaceutically acceptable salts, solvates, enantiomers, diastereomers, geometric isomers, and tautomers can be used in the compositions and methods of the present invention.

It should be appreciated that the above-described embodiments of the invention are not the only embodiments of the invention. All compounds described by the genus of compounds of Formula I are expected to be inhibitors of MMP-13 and useful for the invention methods and compositions. The embodiments of the invention include all possible compounds of Formula I and subsets of the genus of compounds of Formula I, which are permutations of combinations of the species of compounds described by Formula I, and their pharmaceutically acceptable salts thereof. All possible subsets of compounds of Formula I, and pharmaceutically acceptable salts thereof, are incorporated herein, and all pharmaceutical compositions comprising said permutations, and methods of using said permutations, are also incorporated herein. The instant invention should not be limited to the above particularly described embodiments because these subsets of compounds of Formula I are too numerous to practically describe herein.

The compounds of the present invention can be formulated and administered in a wide variety of oral and parenteral dosage forms, including transdermal and rectal administration. All that is required is that an MMP inhibitor be administered to a mammal suffering from a disease in an effective amount, which is that amount required to cause an improvement in the disease and/or the symptoms associated with such disease. It will be recognized to those skilled in the art that the following dosage forms may comprise as the active component, either a compound of Formula I or a corresponding pharmaceutically acceptable salt or solvate of a compound of Formula I. Formulation of the compounds of the present invention is fully described below.

Further, syntheses of the compounds of the present invention may utilize starting materials, intermediates, or reaction products that contain a reactive functional group. A reactive functional group may be protected during chemical reactions using protecting groups which render the reactive groups substantially inert to the reaction conditions. At a step in a synthesis of a compound of the present invention subsequent to the chemical reaction requiring a protecting group, and appropriate to the synthetic strategy employed, the protecting group may be removed. See, for example, *Protective Groups in Organic Synthesis*, $2^{nd}$ ed., Greene T. W. and Wuts P. G., John Wiley & Sons, New York, N.Y., 1991, which is hereby incorporated by reference. Thus, for example, protecting groups such as the following may be utilized to protect suitable amino, hydroxyl, and other groups of related reactivity: carboxylic acyl groups, such as formyl, acetyl, trifluoroacetyl; alkoxycarbonyl groups, such as ethoxycarbonyl, t-butoxycarbonyl (BOC), β,β,β-trichloroethoxycarbonyl (TCEC), β-iodoethoxycarbonyl; aryloxycarbonyl groups, such as benzyloxycarbonyl (CBZ), p-methoxybenzyloxycarbonyl, phenoxycarbonyl; trialkyl silyl groups, such as trimethylsilyl and t-butyldimethylsilyl (TBDMS); and groups such as trityl, tetrahydropyranyl, vinyloxycarbonyl, o-nitrophenylsulfenyl, diphenylphosphinyl, p-toluenesulfonyl, and benzyl may all be utilized. The protecting group may be removed, after completion of the synthetic reaction of interest, by procedures known to those skilled in the art. For example, a BOC group may be removed by acidolysis, a trityl group by hydrogenolysis, TBDMS by treatment with fluoride ions, and TCEC by treatment with zinc. Use of protecting groups in organic synthesis is well within the skill of the average artisan.

The compounds of the present invention can be prepared according to the various synthetic schemes that follow. Protecting groups may be used when appropriate throughout many of the schemes. Although specifically noted in certain schemes, the appropriate use and choice of protecting groups is well known by one skilled in the art, and is not limited to the specific examples below. It is also understood that such groups not only serve to protect chemically reactive sites, but also to enhance solubility or otherwise change physical properties. A good general reference for protecting group preparation and deprotection is "Protective Groups in Organic Synthesis" by Theodora Green, supra. A number of general reactions such as oxidations and reductions are not shown in detail but can be done by methods understood by one skilled in the art. General transformations are well reviewed in "Comprehensive Organic Transformation" by Richard Larock, and the series "Compendium of Organic Synthetic Methods" (1989) published by Wiley-Interscience.

It should be appreciated that reagents, solvents, and starting materials necessary for the preparation of the compounds of the invention may be purchased from a number of commercial sources or may be readily prepared by a number of methods well known to one of average skill in the art of organic chemistry. Further, reactions used to prepare the invention compounds can be carried out under a wide variety of conditions comprising solvents, reagents, catalysts, temperatures, time, atmosphere, and pressure.

Many different methods may be used to prepare the invention compounds. However for purposes of practicing the invention, which comprises compounds, pharmaceutical compositions, and methods of preventing or treating patients with the disorders or diseases recited above, it does not matter how the compounds are made.

A compound of Formula I, or a pharmaceutically acceptable salt thereof, may be prepared by one of ordinary skill in the art of organic chemistry by adapting various synthetic procedures which are well-known in the art of organic chemistry. These synthetic procedures may be found in the literature in, for example, *Reagents for Organic Synthesis*, by Fieser and Fieser, John Wiley & Sons, Inc., New York, 2000; *Comprehensive Organic Transformations*, by Richard C. Larock, VCH Publishers, Inc., New York, 1989; the series *Compendium of Organic Synthetic Methods* (1989) by Wiley-Interscience; the text *Advanced Organic Chemistry*, $5^{th}$ edition, by Jerry March, Wiley-Interscience, New York (2001); or the *Handbook of Heterocyclic Chemistry*, by Alan R. Katritzky, Pergamon Press Ltd., London, (1985), to name a few. Alternatively, a skilled artisan may find methods useful for preparing the invention compounds in the chemical literature by searching widely available databases such as, for example, those available from the Chemical Abstracts Service, Columbus, Ohio, or MDL Information Systems GmbH (formerly Beilstein Information Systems GmbH), Frankfurt, Germany.

Preparations of the compounds of the present invention may use starting materials, reagents, solvents, and catalysts that may be purchased from commercial sources or they may be readily prepared by adapting procedures in the references or resources cited above. Commercial sources of starting materials, reagents, solvents, and catalysts useful in preparing invention compounds include, for example, The Aldrich Chemical Company, and other subsidiaries of Sigma-Aldrich Corporation, St. Louis, Mo., BACHEM, BACHEM A.G., Switzerland, or Lancaster Synthesis Ltd., United Kingdom.

Typical syntheses of the invention compounds are illustrated in the schemes below.

Scheme 1

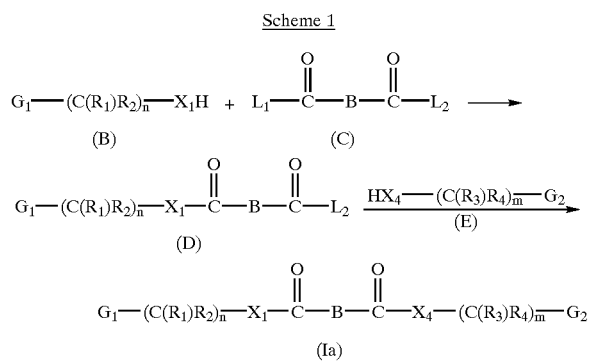

Scheme 1 outlines a preparation of a compound of Formula Ia, which is a compound of Formula I wherein $Q_1$ is $X_1$—C(O), $Q_2$ is C(O)—$X_4$, and $G_1$, $G_2$, $R_1$, $R_2$, $R_3$, $R_4$, n, m, and B are as defined above for Formula I. In Scheme 1, a compound of formula (B), wherein GI, $R_1$, $R_2$, n, and $X_1$ are as defined above for Formula I, is allowed to react with a compound of formula (C), wherein $L_1$ is a leaving group useful in coupling reactions of carboxylic acids such as, for example OH, Cl, F, O—C(O)C(CH$_3$)$_3$, O-(pentafluorophenyl), imidazol-1-yl, benzotriazol-1-yl, and the like and $L_2$ is as defined for $L_1$ or $L_2$ is O—$R_L$, wherein $R_L$ is methyl, ethyl, tert-butyl, benzyl, and the like, to give a compound of formula (D), which is a carboxylic ester (when $X_1$ is O) or an amide (when $X_1$ is NH). The reaction is a coupling reaction between an alcohol ($X_1$ is O) or an amine ($X_1$ is NH) of formula (B) with a carboxylic acid, or an activated derivative thereof, of formula (C), which is a reaction with many variations that are well known in the art of organic chemistry. For example, carboxylic esters and amides may be formed by coupling an alcohol or amine, respectively, with a carboxylic acid using a coupling reagent or reagent mixture such as, for example, N,N'-carbonyldiimidazole (CDI), N,N'-dicyclohexylcarbodiimide (DCC), P(Ph)$_3$ and diethylazodicarboxylate, bis(2-oxo-3-oxazolidinyl)phosphinic chloride (BOP—Cl), POCl$_3$, Ti(Cl)$_4$, and many more, in an aprotic solvent such as, for example, dichloromethane, tetrahydrofuran (THF), dimethylformamide (DMF), dioxane, ethyl acetate, ethyl ether, acetonitrile, and the like. The compound of formula (D) wherein $L_2$ is O—$R_L$, may be deprotected to give a compound of formula (D) wherein $L_2$ is as defined above for $L_1$, using well-known conditions for converting a carboxylic ester to a carboxylic acid such as, for example, saponification with an alkali or alkaline metal hydroxide such as, for example NaOH, KOH, or Mg(OH)$_2$, hydrolysis with an aqueous acid such as, for example, trifluoroacetic acid (TFA), aqueous sulfuric acid, aqueous amberlyst-15 resin, aqueous hydrochloric acid, and the like, or cleavage with a non-aqueous acid or reagent when $L_2$ is O-(tert-butyl) or O-benzyl such as, for example, hydrogen chloride or TFA in dichloromethane, hydrogen bromide in acetic acid, trimethylsilyliodide in dichloromethane, and the like. Alternatively when $L_2$ is O-benzyl, deprotection may be carried out using hydrogenation conditions such as, for example, hydrogen gas at 50 psi in the presence of a hydrogenation catalyst such as, for example, about 5% palladium on carbon or about 10% palladium on barium sulfate. In any event, in a manner similar to that described above for the coupling of a compound of formula (B) with a compound of formula (C), a compound of formula (D) is coupled with a compound of formula (E), wherein $G_2$, $R_3$, $R_4$, m, and $X_4$ are as defined above for Formula I, to give a compound of the present invention of Formula Ia. An alternative preparation of a compound of the present invention of Formula Ia is outlined below in Scheme 8. Compounds of the present invention of Formulas II and III may be prepared by the method outlined in Scheme 1.

Further, a preparation of a compound of Formula Ib, which is a compound of the present invention of Formula I wherein $Q_1$ is C(O)—$X_2$, $Q_2$ is C(O)—$X_4$, and $G_1$, $G_2$, $R_1$, $R_2$, $R_3$, $R_4$, n, m, and B are as defined above for Formula I, is outlined below in Scheme 2.

Scheme 2

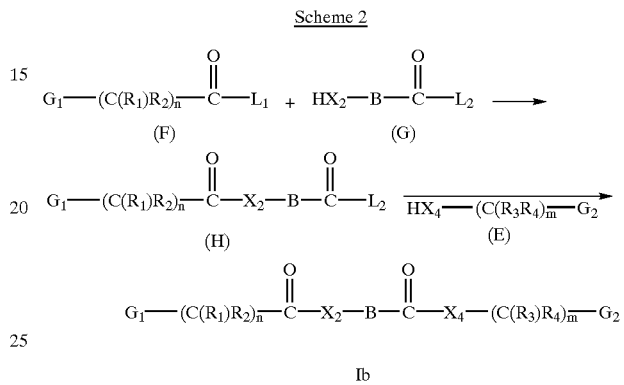

In Scheme 2, a compound of formula (F), wherein $L_1$ is a leaving group as defined above for Scheme 1 and $G_1$, $R_1$, $R_2$, and n are as defined above for Formula I, is allowed to react with a compound of formula (G), wherein $L_2$ is as defined above for Scheme 1 and $X_2$ and B are as defined above for Formula I, to give a compound of formula (H). The reaction is a coupling reaction between an alcohol ($X_2$ is O) or an amine ($X_2$ is NH) of formula (G) with a carboxylic acid, or an activated derivative thereof, of formula (F), which may be accomplished using the conditions described above for Scheme 1 for the coupling of a compound of formula (B) with a compound of formula (C). The compound of formula (H) wherein $L_2$ is O—$R_L$, may be deprotected to give a compound of formula (D) wherein $L_2$ is as defined above for $L_1$, using the well-known conditions for converting a carboxylic ester to a carboxylic acid described above in Scheme 1. In any event, in a manner similar to that described above for the coupling of a compound of formula (B) with a compound of formula (C) in Scheme 1, a compound of formula (H) is coupled with a compound of formula (E), wherein $G_2$, $R_3$, $R_4$, m, and $X_4$ are as defined above for Formula I, to give a compound of the present invention of Formula Ib. Compounds of the present invention of Formula IV may be prepared according to the method outlined in Scheme 2.

Further, a preparation of a compound of Formula Ic, which is a compound of the present invention of Formula I wherein $Q_1$ is $X_1$—C(O), $Q_2$ is $X_3$—C(O), and $G_1$, $G_2$, $R_1$, $R_2$, $R_3$, $R_4$, n, m, and B are as defined above for Formula I, is outlined below in Scheme 3.

Scheme 3

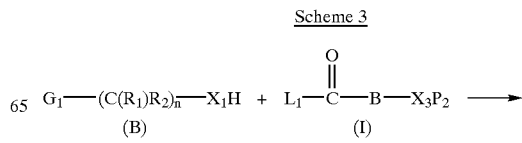

-continued

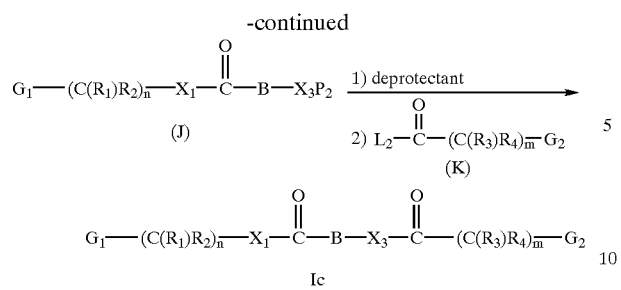

In Scheme 3, a compound of formula (B), which is as described above for Scheme 1, is allowed to react with a compound of formula (I), wherein $L_1$ is a leaving group as defined above for Scheme 1, $X_3$, and B are as defined above for Formula I, and $P_2$ is an alcohol ($X_3$ is O) or amine ($X_3$ is NH) protecting group such as, for example, $C(O)CH_3$, benzyl, trimethylsilyl, tetrahydropyran-2-yl, and the like when $X_3$ is O, or tert-butoxycarbonyl (BOC), benzyloxycarbonyl (CBZ), benzyl, 9-fluorenylmethyloxycarbonyl (FMOC), and the like when $X_3$ is NH, to give a compound of formula (J). The reaction is a coupling reaction between an alcohol ($X_3$ is O) or an amine ($X_3$ is NH) of formula (B) with a carboxylic acid, or an activated derivative thereof, of formula (I), which may be accomplished using the conditions described above for Scheme 1 for the coupling of a compound of formula (B) with a compound of formula (C). A compound of formula (J) is then deprotected using conditions well known in the art of organic chemistry for the deprotection of alcohols or amines. Methods for deprotection may be found above and in, for example, Greene and Wuts P. G., Supra, 1991. Once a compound of formula (J) is deprotected, it is allowed to react with a compound of formula (K), wherein $L_2$ is a protecting group as described above for Scheme 1, and $R_3$, $R_4$, m, and $G_2$ are as defined above for Formula I, in a manner similar to that described above in Scheme 1 for the coupling of a compound of formula (B) with a compound of formula (C), to give a compound of the present invention of Formula Ic.

Further, a preparation of a compound of Formula Id, which is a compound of the present invention of Formula I wherein $Q_1$ is $C(O)$—$X_2$, $Q_2$ is $X_3$—$C(O)$, and $G_1$, $G_2$, $R_1$, $R_2$, $R_3$, $R_4$, n, m, and B are as defined above for Formula I, is outlined below in Scheme 4.

Scheme 4

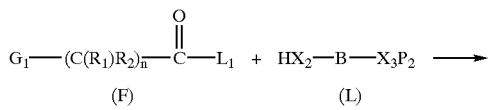

-continued

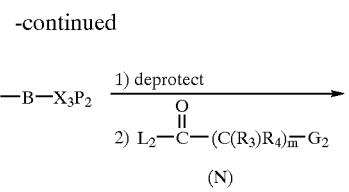

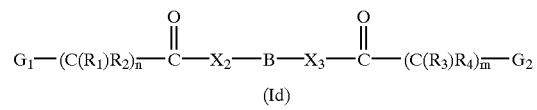

In Scheme 4, a compound of formula (F), which is as described above for Scheme 2, is allowed to react with a compound of formula (L), wherein $X_2$, $X_3$, and B are as described above for Formula I and $P_2$ is as described above for Scheme 3, to give a compound of formula (M). The reaction is a coupling reaction between an alcohol ($X_3$ is O) or an amine ($X_3$ is NH) of formula (L) with a carboxylic acid, or an activated derivative thereof, of formula (F), which may be accomplished using the conditions described above for Scheme 1 for the coupling of a compound of formula (B) with a compound of formula (C). A compound of formula (M) is then deprotected using conditions well-known in the art of organic chemistry for the deprotection of alcohols or amines, as described above for the deprotection of a compound of Formula (J) in Scheme 3. Once a compound of formula (M) is deprotected, it is allowed to react with a compound of formula (N), wherein $L_2$ is a protecting group as described above for Scheme 1, and $R_3$, $R_4$, m, and $G_2$ are as defined above for Formula I, in a manner similar to that described above in Scheme 1 for the coupling of a compound of formula (B) with a compound of formula (C), to give a compound of the present invention of Formula Id.

Further, a preparation of a compound of Formula Ie, which is a compound of the present invention of Formula I wherein $Q_1$ is $X_1$—$C(O)$—$X_2$, $Q_2$ is $X_3$—$C(O)$—$X_4$, and $G_1$, $G_2$, $R_1$, $R_2$, $R_3$, $R_4$, n, m, and B are as defined above for Formula I, is outlined below in Schemes 5 and 6. Scheme 5 outlines two preparations of an intermediate compound of formula (Q) and Scheme 6 outlines the conversion of a compound of Formula (Q) to a compound of the present invention of Formula Ie.

Scheme 5

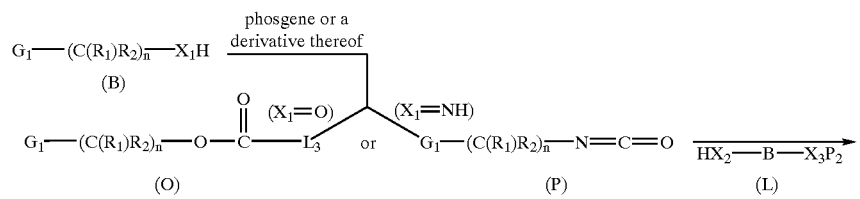

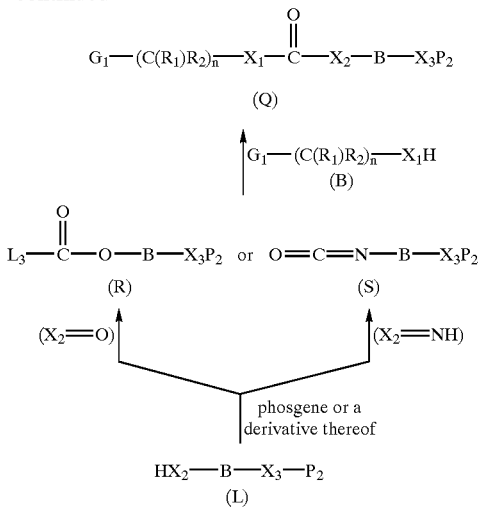

In Scheme 5, a compound of formula (B), which is as described above for Scheme 1, is allowed to react with phosgene, or a derivative thereof such as, for example, triphosgene or pentafluorophenyl chloroformate, in an aprotic solvent such as, for example, dichloromethane, THF, ethyl ether, acetonitrile, and the like, optionally in the presence of from 1 to 5 mole-equivalents of a suitable base such as pyridine or a tertiary organic amine, to give, when $X_1$ is O, a compound of formula (O), wherein $L_3$ is chloro, pentafluorophenoxy, and the like and $G_1$, $R_1$, $R_2$, and n are as defined above for Formula I, or, when $X_1$ is NH, a compound of formula (P), wherein $G_1$, $R_1$, $R_2$, and n are as defined above for Formula I. A compound of formula (O) or formula (P) is allowed to react with a compound of formula (L), which is as described above for Scheme 4, in an aprotic solvent such as, for example, dichloromethane, THF, ethyl ether, acetonitrile, and the like, optionally in the presence of from 1 to 5 mole-equivalents of a suitable base such as a anhydrous potassium carbonate, pyridine, or a tertiary organic amine, to give a compound of formula (Q), wherein $P_2$ is as defined above for Scheme 3 and $G_1$, $R_1$, $R_2$, n, $X_1$, $X_2$, B, and $X_3$ are as defined above for Formula I, which compound of Formula (Q) is a carbonate when $X_1=X_2=O$, a carbamate when $X_1$ or $X_2$ is O and the other of $X_1$ and $X_2$ is NH, or a urea when $X_1=X_2=NH$. Alternatively, a compound of formula (Q) may be prepared by reaction of compound of formula (R), wherein $L_3$ and $P_2$ are as described above and B and $X_3$ are as defined above for Formula I, or a compound of formula (S), wherein $P_2$ is as defined above and B and $X_3$ are as defined above for Formula I, with a compound of Formula (B) in a manner similar to that described above for the reaction of a compound of formula (O) or (P), respectively with a compound of Formula (L). Compounds of formulas (R) or (S) may be prepared from a compound of formula (L) in a manner similar to that described above for the preparation of a compound of formulas (O) or (P), respectively, from a compound of formula (B).

As mentioned above, Scheme 6 outlines the conversion of a compound of formula (Q) to a compound of the present invention of Formula Ie.

Scheme 6

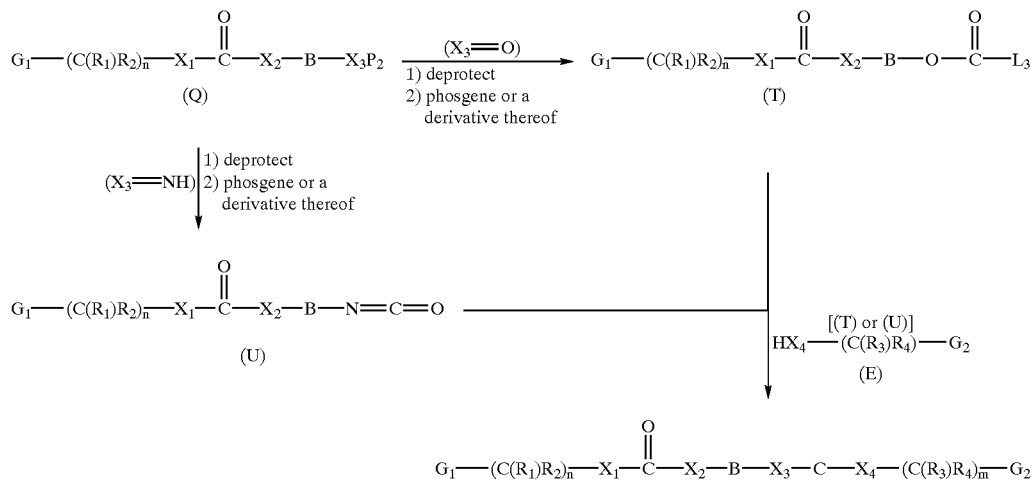

In Scheme 6, a compound of formula (Q), prepared according to Scheme 5 above, is deprotected in a manner similar to that described above for the deprotection of a compound of formula (M) in Scheme 4. Once a compound of formula (Q) is deprotected, it is allowed to react with phosgene, or a derivative thereof, to give, when $X_3$ is O, a compound of formula (T), wherein $L_3$ is as described above for Scheme 5 and $G_1$, $R_1$, $R_2$, n, $X_1$, $X_2$, B are as defined above for Formula I, or, when $X_3$ is NH, a compound of formula (U), wherein $G_1$, $R_1$, $R_2$, n, $X_1$, $X_2$, and B are as defined above for Formula I. The latter reaction is in a manner similar to that described above for Scheme 5 for the reaction of a compound of formula (B) with phosgene, or a derivative thereof, to give a compound of formula (O) or (P), respectively. A compound of formulas (T) or (U) is allowed to react with a compound of formula (E), which is as described above for Scheme 1, to give a compound of the present invention of Formula Ie. The last reaction is similar to that described above for Scheme 5 for the preparation of a compound of formula (Q) from a compound of formula (B) and a compound of formulas (R) or (S), respectively.

Further, a preparation of a compound of Formula If, which is a compound of the present invention of Formula I wherein $Q_1$ is $X_1$—C(O)—$X_2$, $Q_2$ is $X_3$—C(O), and $G_1$, $G_2$, $R_1$, $R_2$, $R_3$, $R_4$, n, m, and B are as defined above for Formula I, is outlined below in Scheme 7.

Scheme 7

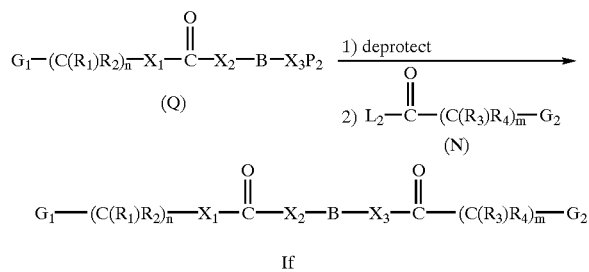

If

In Scheme 7, a compound of formula (Q), prepared according to Scheme 5, is deprotected according to Scheme 6, and the deprotected compound is allowed to react via a coupling reaction with a compound of formula (N), prepared according to Scheme 4, to give a compound of Formula If. The deprotection/coupling reaction sequence is done in a manner similar to the deprotection/reaction of a compound of formula (M) with a compound of formula (N) as described for Scheme 4. Compounds of the present invention of Formula V may be prepared according to the method of Scheme 7.

Further, a preparation of a compound of Formula Ia, which is a compound of the present invention of Formula I wherein $Q_1$ is $X_1$—C(O), $Q_2$ is C(O)—$X_3$, and $G_1$, $G_2$, $R_1$, $R_2$, $R_3$, $R_4$, n, m, and B are as defined above for Formula I, is outlined below in Scheme 8.

Scheme 8

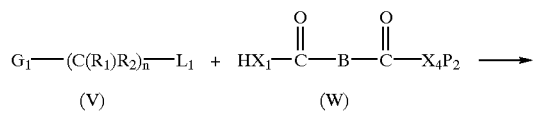

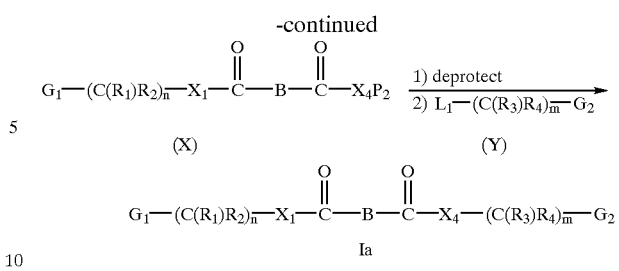

In Scheme 8, a compound of formula (V), wherein $L_1$ is as described above for Scheme 1 and $G_1$, $R_1$, $R_2$, and n are as defined above for Formula I, is allowed to react with a compound of formula (W), wherein $P_2$ is as described above for Scheme 3 and $X_1$, $X_4$, and B are as defined above for Formula I, to give a compound of formula (X). The reaction is carried out in a solvent such as, for example, THF, isopropanol, ethyl ether, dichloromethane, DMF, dimethylsulfoxide (DMSO), acetonitrile, acetone, and the like, optionally in the presence of from 1 to 4 mole-equivalents of a suitable base, such as, for example, n-butyl lithium, a tertiary organic amine, pyridine, sodium carbonate, potassium tert-butoxide, sodium hydride, and the like. A compound of formula (X) is deprotected according to the procedure described above for Scheme 3 for the deprotection of a compound of formula (J), and the deprotected intermediate is allowed to react with a compound of formula (Y), wherein $L_1$ is as defined above for Scheme 1 and $R_3$, $R_4$, m, and $G_2$ are as defined above for Formula I, to give a compound of the present invention of Formula Ia. The deprotection/coupling reaction sequence is done in a manner similar to the deprotection/reaction of a compound of formula (M) with a compound of formula (N) as described for Scheme 4. The synthetic strategy employed in Scheme 8 may also be adapted for the preparation of compounds of the present invention of Formulas Ib and Ic. Compounds of the present invention of Formulas II and III may be prepared according to the method of Scheme 8.

The following detailed examples further illustrate the synthesis of typical invention compounds of Formula I. The examples are representative only, and are not to be construed as limiting the invention in any respect.

The following specific starting materials can be prepared using literature procedures, according to the following references.

For the preparation of 3-Methoxy-2,5-thiophenedicarboxylic acid (Examples 3 and 4), see *Chem. Ber.,* 1954;87:841.

For the preparation of 2,4-Thiophenecarboxylic acid (Examples 5 and 6), see *Org. Prep. Proc. Int.,* 1971;3:295.

For the preparation of N-Methyl-2,4-pyrroledicarboxylic acid (Examples 7 and 8), see *Chem. Ber.,* 1970; 103:3196.

For the preparation of 1,3-Diisopropyl-2-benzylisourea (Example 9), see *Liebigs Ann. Chem.,* 1965;685:161.

For the preparation of 5-Methyl-4-amino-thiophene-2-carboxylic acid (Examples 10 and 12), see *Bull. Acad. Sci. USSR, Div. Chem. Sci.,* 1984;33:2338.

For the preparation of 5-Methyl-4-nitro-thiophene-2-carboxylic acid methyl ester (Example 14), see *J. Am. Chem. Soc.,* 1951 ;73:3812.

For the preparation of 5-Methyl-4-nitro-thiophene-2-carboxylic acid (Examples 9, 15, and 16), see *J. Chem. Soc.,* 1980;Perk 2:1331.

EXAMPLE 1

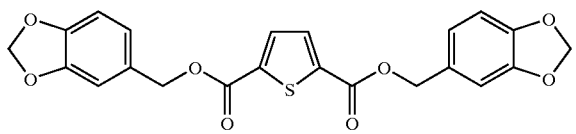

Thiophene-2,5-dicarboxylic Acid di-1,3-benzodioxol-5-ylmethyl Ester

Cesium carbonate (4.7 g, 14.4 mmol) was added to a stirred solution of 2,5-thiophenedicarboxylic acid in dimethylformamide (35 mL) under an inert atmosphere at room temperature. After 5 minutes, a solution of 3,4-methylenedioxybenzyl chloride in dichloromethane (3.7 mL, 14.3 mmol) was added. After 24 hours the mixture was stirred into water (150 mL) and acidified with dilute aqueous HCl. After several hours, the precipitate was filtered off, rinsed with water, and dried to afford 0.6 g of thiophene-2,5-dicarboxylic acid di-1,3-benzodioxol-5-ylmethyl ester. Recrystallization of a sample from ethanol gave product with a mp 141–148° C.

EXAMPLE 2

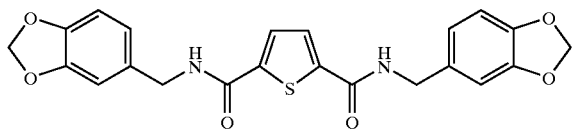

Thiophene-2,5-dicarboxylic Acid bis-[(1,3-benzodioxol-5-ylmethyl)-amide]

1,1'-Carbonyldiimidazole (1.2 g, 7.4 mmol) was added to a stirred solution of 2,5-thiophene-dicarboxylic acid (0.5 g, 3.0 mmol) in dimethylformamide (25 mL) under an inert atmosphere, and the mixture was heated to 55° C. to 60° C. After 30 minutes, the mixture was allowed to cool and piperonylamine (1.05 g, 6.7 mmol) was added. The mixture was reheated to 55° C. to 60° C. After 3 hours, the mixture was allowed to cool, and was poured into water (250 mL), and the aqueous mixture was stirred. After several hours, the precipitate was filtered off, rinsed with water, and dried to afford 1.2 g of thiophene-2,5-dicarboxylic acid bis-[(1,3-benzodioxol-5-ylmethyl)-amide]. Recrystallization of a sample from ethanol gave product with a mp 207–209° C.

EXAMPLE 3

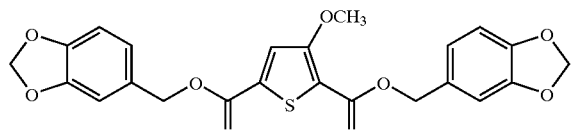

3-Methoxy-thiophene-2,5-dicarboxylic Acid di-1,3-benzodioxol-5-ylmethyl Ester

The title compound was prepared according to the procedure of Example 2 using carbonyldiimidazole (0.8 g, 4.8 mmol), 3-methoxy-2,5-thiophenedicarboxylic acid (0.4 g, 2.0 mmol), and piperonyl alcohol (0.62 g, 4.0 mmol). Acidification of the aqueous workup mixture with dilute hydrochloric acid prior to filtration afforded 0.8 g of 3-methoxy-thiophene-2,5-dicarboxylic acid di-1,3-benzodioxol-5-ylmethyl ester. Recrystallization of a sample from acetonitrile gave product with a mp 153–155° C.

EXAMPLE 4

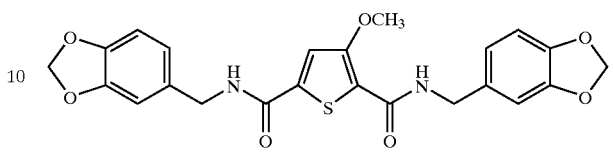

3-Methoxy-thiophene-2,5-dicarboxylic Acid bis-[(1,3-benzodioxol-5-ylmethyl)-amide]

The title compound was prepared according to the procedure of Example 2 using carbonyldiimidazole (1.0 g, 6.2 mmol), 3-methoxy-2,5-thiophenedicarboxylic acid (0.5 g, 2.5 mmol), and piperonylamine (0.85 g, 5.6 mmol) to afford 1.05 g of 3-methoxy-thiophene-2,5-dicarboxylic acid bis-[(1,3-benzodioxol-5-ylmethyl)-amide]. Recrystallization of a sample from dimethylformamide gave product with a mp 191–195° C.

EXAMPLE 5

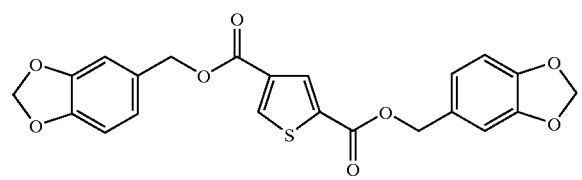

Thiophene-2,4-dicarboxylic Acid di-1,3-benzodioxol-5-ylmethyl Ester

The title compound was prepared according to the procedure described for Example 2 using carbonyldiimidazole (1.1 g, 6.8 mmol), 2,4-thiophene-dicarboxylic acid (0.5 g, 2.9 mmol) and piperonyl alcohol (0.45 g, 2.9 mmol). Acidification of the aqueous workup mixture with dilute hydrochloric acid prior to filtration afforded 0.71 g of thiophene-2,4-dicarboxylic acid di-1,3-benzodioxol-5-ylmethyl ester. Recrystallization of a sample from methanol followed by trituration in ethyl acetate then ether and drying gave product with a mp 164–165° C.

EXAMPLE 6

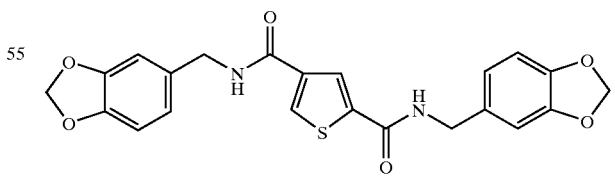

Thiophene-2,4-dicarboxylic Acid bis-[(1,3-benzodioxol-5-ylmethyl)-amide]

The title compound was prepared according to the procedure described for Example 2 using carbonyldiimidazole (1.2 g, 7.4 mmol), 2,4-thiophene-dicarboxylic acid (0.5 g, 3.0 mmol), and piperonylamine (1.05 g, 6.7 mmol) to afford 1.2 g of thiophene-2,4-dicarboxylic acid bis-[(1,3-benzodioxol-5-ylmethyl)-amide]. Recrystallization of a sample from ethanol gave product with a mp 174–175° C.

EXAMPLE 7

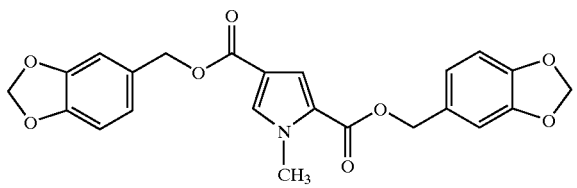

1-Methyl-1H-pyrrole-2,4-dicarboxylic Acid di-1,3-benzodioxol-5-ylmethyl Ester 1,1'-Carbonyldiimidazole (1.3 g, 8.0 mmol) was added to a stirred solution of N-methyl-2,4-pyrrole-dicarboxylic acid (0.6 g, 3.5 mmol) in dimethylformamide (6 mL) under an inert atmosphere and heated to 40° C. After 30 minutes the mixture was allowed to cool, and piperonyl alcohol (1.1 g, 7.1 mmol) was added. The mixture was heated to 60° C. for 3 hours, then poured into water (100 mL), stirred, and acidified with 4N HCl. The resulting mixture was extracted twice with ethyl acetate (60 mL), and the combined extracts were washed successively with water, 0.5 M aqueous sodium bicarbonate, and saturated brine, then dried over MgSO$_4$. The solvent was removed under reduced pressure, and the residue was dissolved in a minimum of hot acetonitrile, cooled, and filtered. The filtrate was taken to dryness under reduced pressure, and the residual product (0.9 g) was chromatographed on a column of silica gel under nitrogen pressure, eluting with ethyl acetate/petroleum ether 2:3. Evaporation of the appropriate fractions and drying afforded 1-methyl-1H-pyrrole-2,4-dicarboxylic acid di-1,3-benzodioxol-5-ylmethyl ester; mp 103–110° C.

EXAMPLE 8

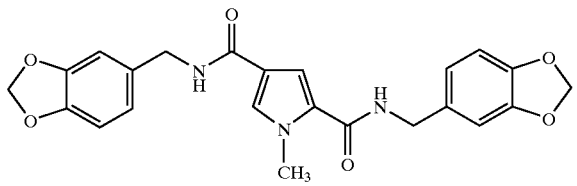

1-Methyl-1H-pyrrole-2,4-dicarboxylic Acid bis-[(1,3-benzodioxol-5-ylmethyl)-amide]

The title compound was prepared according to the procedure described for Example 2 using carbonyldiimidazole (1.2 g, 7.4 mmol), N-methyl-2,4-pyrroledicarboxylic acid (0.5 g, 3.0 mmol) and piperonylamine (1.1 g, 7.3 mmol) to afford 1.1 g of 1-methyl-1H-pyrrole-2,4-dicarboxylic acid bis-[(1,3-benzodioxol-5-ylmethyl)-amide]. Recrystallization of a sample from acetonitrile gave product with a mp 147–152° C.

EXAMPLE 9

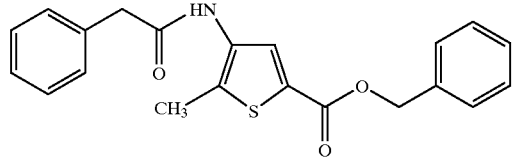

5-Methyl-4-phenylacetylamino-thiophene-2-carboxylic Acid Benzyl Ester

Step 1: 5-Methyl-4-nitro-thiophene-2-carboxylic Acid Benzyl Ester

A mixture of 5-methyl-4-nitro-thiophene-2-carboxylic acid (1.0 g, 5.3 mmol) and 1,3-diisopropyl-2-benzylisourea (1.54 g, 6.4 mmol) in acetonitrile (25 mL) was stirred under an inert atmosphere and heated to reflux. After 48 hours the mixture was cooled, the solvent was removed under reduced pressure, and the residue was triturated in diethyl ether and cooled. The precipitate was filtered off and rinsed with cold ether. The filtrate and washings were combined, and rotary evaporated under reduced pressure. The resulting residue was dissolved in a minimum of ethyl acetate, and the solution was filtered through a column of silica gel, eluting with more ethyl acetate. The filtrate was rotary evaporated to dryness under reduced pressure to afford 1.2 g of 5-methyl-4-nitro-thiophene-2-carboxylic acid benzyl ester. A sample was chromatographed on silica gel in ether/petroleum ether 1:1, then recrystallized from ethanol to give product with a mp 57–58° C.

Step 2: 5-Methyl-4-amino-thiophene-2-carboxylic Acid Benzyl Ester

Sponge nickel (0.6 g water wet) was added to a solution of 5-methyl-4-nitro-thiophene-2-carboxylic acid benzyl ester (0.93 g, 3.4 mmol), prepared as described in Step 1 above, in tetrahydrofuran (50 mL), and the mixture was hydrogenated at room temperature under hydrogen atmosphere at a starting pressure of 50 psi. After a reaction time of 2.4 hours, the pressure was released and the mixture filtered. The slurry was rinsed with tetrahydrofuran, and the filtrate was stripped of solvent under reduced pressure, leaving 0.9 g of 5-methyl-4-amino-thiophene-2-carboxylic acid benzyl ester as an oil.

Step 3: 5-Methyl-4-phenylacetylamino-thiophene-2-carboxylic Acid Benzyl Ester

Phenylacetyl chloride (0.26 g, 1.7 mmol) was added to a stirred solution of 5-methyl-4-amino-thiophene-2-carboxylic acid benzyl ester (0.4 g, 1.6 mmol), prepared as described above in Step 2, and diisopropylethylamine (0.26 g, 2.0 mmol) in tetrahydrofuran (15 mL) under an inert atmosphere at room temperature. After 18 hours, the mixture was diluted with water (100 mL) and acidified with aqueous HCl. The precipitate was filtered off, rinsed with water, then ethanol, then ether, and dried to afford 0.3 g of 5-methyl-4-phenylacetylamino-thiophene-2-carboxylic acid benzyl ester. Recrystallization of a sample from acetonitrile gave product with a mp 173–174° C.

EXAMPLE 10

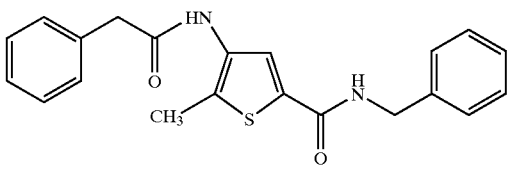

5-Methyl-4-phenylacetylamino-thiophene-2-carboxylic Acid Benzylamide

Step 1: 5-Methyl-4-phenylacetylamino-thiophene-2-carboxylic Acid

Diisopropylethylamine (3.33 g, 25.8 mmol) was added to a stirred suspension of 5-methyl-4-amino-thiophene-2-carboxylic acid hydrochloride (1.4 g, 7.0 mmol) in tetrahydrofuran (25 mL) under an inert atmosphere at room temperature. After 1½ hours, phenylacetyl chloride (1.1 g, 7.2 mmol) was added. After 24 hours, the mixture was diluted with water (200 mL) and acidified with dilute aqueous hydrochloric acid. After 12 hours the precipitate was filtered off, rinsed with water, and dried to afford 1.5 g of 5-methyl-4-phenylacetylamino-thiophene-2-carboxylic acid. Recrystallization of a sample from acetonitrile gave product with a mp 249–250° C.

Step 2: 5-Methyl-4-phenylacetylamino-thiophene-2-carboxylic Acid Benzylamide

The title compound was prepared according to the procedure described for Example 2 using carbonyldiimidazole (0.26 g, 1.7 mmol), 5-methyl-4-phenylacetylamino-thiophene-2-carboxylic acid from Step 1 (0.29 g, 1.1 mmol), and benzyl amine (0.11 g, 1.1 mmol). Acidification of the aqueous workup mixture with dilute hydrochloric acid prior to filtration afforded 0.37 g of 5-methyl-4-phenylacetylamino-thiophene-2-carboxylic acid benzylamide. A sample of the crude product was stirred in 2 M aqueous KHCO₃ for several hours, filtered off, rinsed with water, dried, and recrystallized from acetonitrile to give product with a mp 167–170° C.

EXAMPLE 11

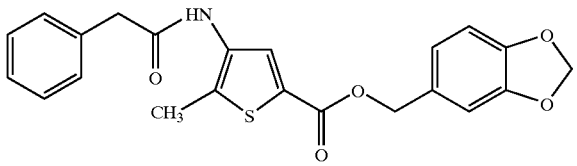

5-Methyl-4-phenylacetylamino-thiophene-2-carboxylic Acid 1,3-benzodioxol-5-ylmethyl Ester The title compound was prepared according to the procedure described for Example 2 using carbonyldiimidazole (0.26 g, 1.7 mmol), 5-methyl-4-phenylacetylamino-thiophene-2-carboxylic acid from Example 10, Step 1 (0.3 g, 1.1 mmol), and piperonyl alcohol (0.17 g, 1.1 mmol). Acidification of the aqueous workup mixture with dilute hydrochloric acid prior to filtration afforded 0.33 g of 5-methyl-4-phenylacetylamino-thiophene-2-carboxylic acid 1,3-benzodioxol-5-ylmethyl ester. A sample of the product was stirred in 2 M aqueous KHCO₃ for several hours, filtered off, rinsed with water, and dried to give product with a mp 191–195° C.

EXAMPLE 12

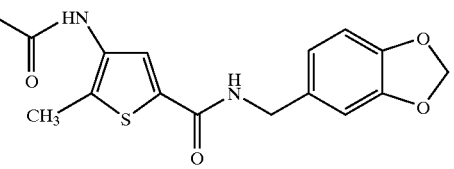

5-Methyl-4-phenylacetylamino-thiophene-2-carboxylic Acid (1,3-benzodioxol-5-ylmethyl)-amide The title compound was prepared according to the procedure described for Example 2 using carbonyldiimidazole (0.26 g, 1.7 mmol), 5-methyl-4-phenylacetylamino-thiophene-2-carboxylic acid from Example 10, Step 1 (0.3 g, 1.1 mmol), and piperonyl amine (0.17 g, 1.1 mmol) to afford 0.43 g of 5-methyl-4-phenylacetylamino-thiophene-2-carboxylic acid (1,3-benzodioxol-5-ylmethyl)-amide. A sample of the product was chromatographed on silica gel, eluting with ethyl acetate. Evaporation of the effluent under reduced pressure gave product with a mp 138–140° C.

EXAMPLE 13

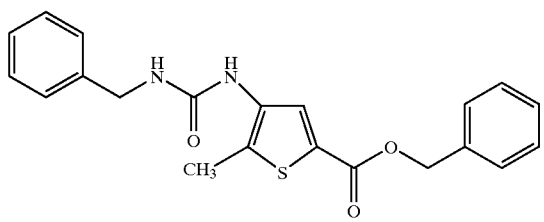

4-(3-Benzyl-ureido)-5-methyl-thiophene-2-carboxylic Acid Benzyl Ester

Benzyl isocyanate (0.29 g, 2.2 mmol) was added to a stirred solution of 5-methyl-4-amino-thiophene-2-carboxylic acid benzyl ester from Example 9, Step 2 (0.5 g, 2.0 mmol) in toluene (10–15 mL) at room temperature under an inert atmosphere. After 20 minutes, the mixture was heated to reflux for 10 minutes, allowed to cool, then diluted with an equal volume of diethyl ether. After 10 minutes, the precipitate was filtered off, rinsed with ether, and dried to afford 0.5 g of 4-(3-benzyl-ureido)-5-methyl-thiophene-2-carboxylic acid benzyl ester; mp 208–209° C.

EXAMPLE 14

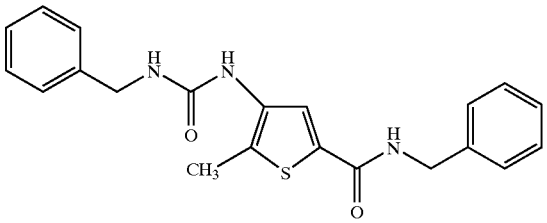

4-(3-Benzyl-ureido)-5-methyl-thiophene-2-carboxylic Acid Benzylamide

Step 1: 5-Methyl-4-(3-benzyl-ureido)-thiophene-2-carboxylic Acid

A 2N aqueous potassium hydroxide solution (16 mL) was added to a stirred solution of 5-methyl-4-(3-benzyl-ureido)-thiophene-2-carboxylic acid methyl ester from Step 2 of Example 16 below (0.4 g, 1.3 mmol) in warm methanol (4 mL), and the mixture was heated under reflux. After 1 hour the mixture was cooled, diluted with water (100 mL), and acidified with aqueous HCl. The precipitate was filtered off, rinsed with water, then ethanol, then ether, and dried to afford 0.29 g of 5-methyl-4-(3-benzyl-ureido)-thiophene-2-carboxylic acid; mp 259–260° C.

Step 2: 4-(3-Benzyl-ureido)-5-methyl-thiophene-2-carboxylic Acid Benzylamide

The title compound was prepared according to the procedure described for Example 2 using carbonyldiimidazole (0.24 g, 1.7 mmol), 4-(3-benzyl-ureido)-5-methyl-thiophene-2-carboxylic acid from Step 3 (0.27 g, 0.9 mmol), and benzyl amine (0.1 g, 0.9 mmol) to afford 0.33 g of 4-(3-benzyl-ureido)-5-methyl-thiophene-2-carboxylic acid benzylamide. A sample of the crude product was stirred in 2 M aqueous $KHCO_3$ for several hours, filtered off, rinsed with water, dried, and recrystallized from methanol to give product with a mp 180–181° C.

EXAMPLE 15a

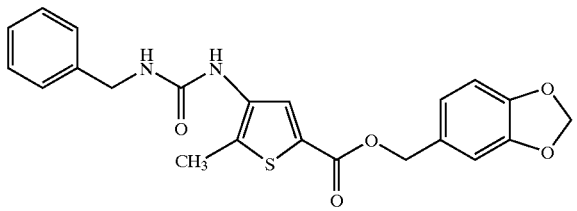

4-(3-Benzyl-ureido)-5-methyl-thiophene-2-carboxylic Acid 1,3-benzodioxol-5-ylmethyl Ester Step 1: 5-Methyl-4-nitro-thiophene-2-carboxylic Acid 1,3-benzodioxol-5-ylmethyl Ester The title compound was prepared according to the procedure described for Example 2 using carbonyldiimidazole (0.75 g, 4.3 mmol), 5-methyl-4-nitro-thiophene-2-carboxylic acid (0.6 g, 3.2 mmol), and piperonyl alcohol (0.5 g, 3.3 mmol) to afford 0.8 g of 5-methyl-4-nitro-thiophene-2-carboxylic acid 1,3-benzodioxol-5-ylmethyl ester. A sample of the product was triturated in ethanol, cooled, filtered, and dried to give product with a mp 78–79° C.

Step 2: 5-Methyl-4-amino-thiophene-2-carboxylic Acid 1,3-benzodioxol-5-ylmethyl Ester Sponge nickel (0.5 g water wet) was added to a solution of 5-methyl-4-nitro-thiophene-2-carboxylic acid 1,3-benzodioxol-5-ylmethyl ester (0.55 g, 1.7 mmol) from Step 1 in tetrahydrofuran (100 mL) and the mixture was hydrogenated at room temperature under a hydrogen atmosphere at a starting pressure of 50 psi. After a reaction time of 2.79 hours, the pressure was released, and the mixture was filtered. The slurry was washed with tetrahydrofuran, and the filtrate was stripped of solvent under reduced pressure to afford a crystalline residue. The residue was triturated in diethyl ether and filtered to afford 5-methyl-4-amino-thiophene-2-carboxylic acid 1,3-benzodioxol-5-ylmethyl ester. Chromatography on silica gel in ethyl acetate, then evaporation of the effluent under reduced pressure gave 0.14 g of 5-methyl-4-amino-thiophene-2-carboxylic acid 1,3-benzodioxol-5-ylmethyl ester.

Step 3: 4-(3-Benzyl-ureido)-5-methyl-thiophene-2-carboxylic Acid 1,3-benzodioxol-5-ylmethyl Ester 5-Methyl-4-amino-thiophene-2-carboxylic acid 1,3-benzodioxol-5-ylmethyl ester from Step 2 (0.15 g, 0.5 mmol) was dissolved in hot 1,4-dioxane (6–8 mL) under an inert atmosphere, stirred, and treated with benzyl isocyanate (0.07 g, 0.5 mmol). After 72 hours at room temperature, the mixture was diluted with diethyl ether (50 mL). After another hour the precipitate was filtered off, rinsed with ether, and dried to afford 0.14 g of 4-(3-benzyl-ureido)-5-methyl-thiophene-2-carboxylic acid 1,3-benzodioxol-5-ylmethyl ester; mp 216–217° C.

EXAMPLE 15b

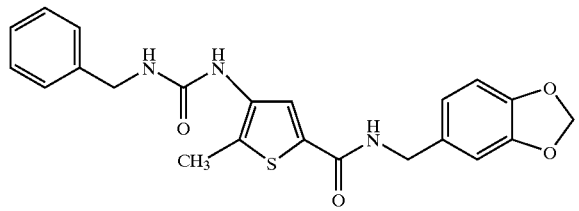

4-(3-Benzyl-ureido)-5-methyl-thiophene-2-carboxylic Acid (1,3-benzodioxol-5-ylmethyl)-amide Step 1: 5-Methyl-4-nitro-thiophene-2-carboxylic Acid (1,3-benzodioxol-5-ylmethyl)-amide The title compound was prepared according to the procedure described for Example 2 using carbonyldiimidazole (0.7 g, 4.3 mmol), 5-methyl-4-nitro-thiophene-2-carboxylic acid (0.6 g, 3.2 mmol), and piperonyl amine (0.5 g, 3.3 mmol). Acidification of the aqueous workup mixture with dilute hydrochloric acid prior to filtration afforded 1 g of 5-methyl-4-nitro-thiophene-2-carboxylic acid (1,3-benzodioxol-5-ylmethyl)-amide. A sample was dissolved in ethyl acetate and filtered through a short column of silica gel to give 5-methyl-4-nitro-thiophene-2-carboxylic acid (1,3-benzodioxol-5-ylmethyl)-amide; mp 181–183° C.

Step 2: 5-Methyl-4-amino-thiophene-2-carboxylic Acid (1,3-benzodioxol-5-ylmethyl)-amide Sponge nickel (0.7 g water wet) was added to a solution of 5-methyl-4-nitro-thiophene-2-carboxylic acid (1,3-benzodioxol-5-ylmethyl)-amide (0.72 g, 2.2 mmol) in methanol (50 mL), and the mixture was hydrogenated at room temperature under a hydrogen atmosphere at a starting pressure of 50 psi. After a reaction time of 1.77 hours, the pressure was released, and the mixture was filtered. The slurry was rinsed with methanol, and the filtrate was stripped of solvent under reduced pressure to afford 0.6 g of 5-methyl-4-amino-thiophene-2-carboxylic acid (1,3-benzodioxol-5-ylmethyl)-amide as an oil.

Step 3: 4-(3-Benzyl-ureido)-5-methyl-thiophene-2-carboxylic Acid (1,3-benzodioxol-5-ylmethyl)-amide A mixture of 5-methyl-4-amino-thiophene-2-carboxylic acid (1,3-benzodioxol-5-ylmethyl)-amide from Step 2 (0.6 g, 2.1 mmol) and benzyl isocyanate (0.28 g, 2.1 mmol) in 1,4-dioxane (100 mL) was stirred under an inert atmosphere and heated to reflux. After 30 minutes, the mixture was allowed to cool, and the solvent was removed under reduced pressure. The residue was triturated in a small amount of acetonitrile, cooled, and filtered to afford 0.33 g of 4-(3-benzyl-ureido)-5-methyl-thiophene-2-carboxylic acid (1,3- benzodioxol-5-ylmethyl)-amide. A sample was recrystallized from methanol to give product with a mp 194–195° C.

EXAMPLE 16

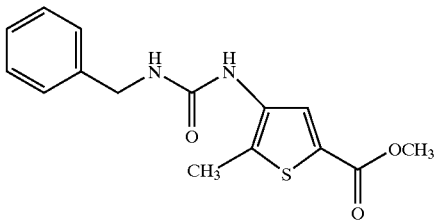

5-Methyl-4-(3-benzyl-ureido)-thiophene-2-carboxylic Acid Methyl Ester

Step 1: 5-Methyl-4-amino-thiophene-2-carboxylic Acid Methyl Ester

Sponge nickel (1.0 g water wet) was added to a solution of 5-methyl-4-nitro-thiophene-2-carboxylic acid methyl ester (1.79 g, 8.9 mmol) in methanol (50 mL), and the mixture was hydrogenated at room temperature under a hydrogen atmosphere at a starting pressure of 50 psi. After a reaction time of 25 hours, the pressure was released and the mixture filtered. The slurry was rinsed with methanol, and the filtrate was stripped of solvent under reduced pressure to afford 1.5 g of 5-methyl-4-amino-thiophene-2-carboxylic acid methyl ester. A sample was dissolved in ethyl acetate and filtered through a short column of silica gel. Evaporation of the effluent under reduced pressure gave product with a mp 90–91° C.

Step 2: 5-Methyl-4-(3-benzyl-ureido)-thiophene-2-carboxylic Acid Methyl Ester

The title compound was prepared according to the procedure described for Example 13 using benzyl isocyanate (0.4 g, 3.2 mmol) and 5-methyl-4-amino-thiophene-2-carboxylic acid methyl ester from Step 1 to afford 0.77 g of 5-methyl-4-(3-benzyl-ureido)-thiophene-2-carboxylic acid methyl ester. Recrystallization of a sample from acetonitrile gave product with a mp 185–187° C.

EXAMPLE 17

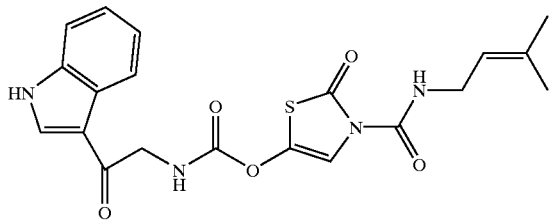

[2-(1H-Indol-3-yl)-2-oxo-ethyl]-carbamic Acid 3-(3-methyl-but-2-enylcarbamoyl)-2-oxo-2,3-dihydro-thiazol-5-yl Ester Step (a): Preparation of 3-(3-methyl-but-2-en-1-yl) aminocarbonyl-2,5-thiazolidinedione To a stirred solution or partial solution of 2,5-thiazolidinedione (0.010 mol) in tetrahydrofuran (THF) is added neat (or a solution in dichloromethane or THF) (3-methyl-but-2-en-1-yl)-isocyanate (0.010 mol), prepared by allowing (3-methyl-but-2-en-1-yl)amine with 0.33 mol equivalents of triphosgene in dichloromethane optionally in the presence of a tertiary amine base or pyridine, and the mixture is stirred. Reaction progress may be followed by thin layer chromatography (TLC) or high performance liquid chromatography (HPLC). When a sufficient amount of desired product is formed, the mixture (or, optionally, the residue which is obtained after first rotary evaporating off the reaction solvent) is partitioned between ethyl acetate and an excess of about 0.1 M hydrochloric acid. The organic layer is washed with brine, dried over sodium sulfate, and rotary evaporated to give 3-(3-methyl-but-2-en-1-yl) aminocarbonyl-2,5-thiazolidinedione, which may be purified, if needed or desired, by chromatography on silica gel or crystallization.

Step (b): Preparation of 3-acetyl-1-(tert-butoxycarbonyl)-indole

To a stirred solution of 3-acetylindole (0.01 mol) in THF is added (BOC)$_2$O (0.01 mol) and a tertiary amine base (0.01 mol), and the mixture is stirred. Reaction progress may be followed by TLC or HPLC. When a sufficient amount of desired product is formed, the mixture (or, optionally, the residue which is obtained after first rotary evaporating off the reaction solvent) is partitioned between ethyl acetate and an excess of about 0.1 M sodium hydroxide. The organic layer is washed with brine, dried over sodium sulfate, and rotary evaporated to give 3-acetyl-1-(tert-butoxycarbonyl)-indole, which may be purified, if needed or desired, by chromatography on silica gel or crystallization.

Step (c): Preparation of 3-bromoacetyl-1-(tert-butoxycarbonyl)-indole

To a stirred solution of 3-acetyl-1-(tert-butoxycarbonyl)-indole, which may be prepared as described in Step (b) above, (0.01 mol), in THF at a temperature of about –80° C. to about 25° C. is added bromine (0.01 mol), and the mixture is stirred from about 5 minutes to about 24 hours. Reaction progress may be followed by TLC or HPLC. When a sufficient amount of desired product is formed, the mixture (or, optionally, the residue which is obtained after first rotary evaporating off the reaction solvent) is partitioned between ethyl acetate and an excess of an aqueous solution of sodium bisulfite or an aqueous solution of sodium thiosulfate. The organic layer is washed with water, then brine, dried over sodium sulfate, and rotary evaporated to give 3-bromoacetyl-1-(tert-butoxycarbonyl)-indole, which may be purified, if needed or desired, by chromatography on silica gel or crystallization.

Step (d): Preparation of 3-azidoacetyl-1-(tert-butoxycarbonyl)-indole

To a stirred solution of 3-bromoacetyl-1-(tert-butoxycarbonyl)-indole, which may be prepared as described in Step (c) above, (0.01 mol), in THF is added a solution or suspension of sodium azide (0.01 to 0.05 mol) in THF, which optionally contains from 0% to 50% water or methanol, and the mixture is stirred. Reaction progress may be followed by TLC or HPLC. When a sufficient amount of desired product is formed, the mixture (or, optionally, the residue which is obtained after first rotary evaporating off the reaction solvent) is partitioned between ethyl acetate and water. The organic layer is washed with brine, dried over sodium sulfate, and rotary evaporated to give 3-azidoacetyl-1-(tert-butoxycarbonyl)-indole, which may be purified, if needed or desired, by chromatography on silica gel or crystallization.

Step (e): Preparation of 3-aminoacetyl-1-(tert-butoxycarbonyl)-indole

To a stirred solution of 3-azidoacetyl-1-(tert-butoxycarbonyl)-indole (0.01 mol), which may be prepared as described in Step (d) above, in THF is added a reducing agent such as, for example, a catalytic amount (0.0001 to 0.001 mol) of a hydrogenolysis catalyst such as, for example, 10% palladium on carbon, and the mixture is shaken under a hydrogen atmosphere at from atmospheric pressure to about 75 psi. (Alternatively, other reducing agents such as lithium aluminum hydride may be used. Reaction work-up conditions may be modified according to the reduction reaction employed.) Reaction progress may be followed by TLC or HPLC. When a sufficient amount of desired product is formed, the mixture is filtered, optionally through a filter aid such as, for example, CELITE (Celite Products Company, Los Angeles, Calif.), and the filter cake is washed with additional solvent (THF). The filtrate and washings rotary evaporated to give 3-aminoacetyl-1-(tert-butoxycarbonyl)-indole, which may be purified, if needed or desired, by chromatography on silica gel or crystallization. Alternatively, the 3-aminoacetyl-1-(tert-butoxycarbonyl)-indole can be dissolved in ethyl ether, which optionally contains minor amounts (i.e., <50% v/v) of THF, and 1 mol equivalent of a solution of either hydrogen chloride in ethyl ether or concentrated hydrochloric acid is added. The solid 3-aminoacetyl-1-(tert-butoxycarbonyl)-indole hydrochloride which precipitates, or if little or no solid precipitates, the 3-aminoacetyl-1-(tert-butoxycarbonyl)-indole hydrochloride obtained upon rotary evaporation of the mixture, may be purified, if needed or desired, by crystallization.

Step (f): Preparation of 2-(1-tert-butoxycarbonyl-indol-3-yl)-2-oxo-ethylisocyanate To a stirred solution of 3-aminoacetyl-1-(tert-butoxycarbonyl)-indole, which may be prepared as described in Step (e) above, (0.01 mol), optionally in the presence of from 1 to 3 mol equivalents of a volatile (i.e., boiling point <150° C.) non-nucleophilic base such as, for example, a volatile tertiary organic amine or pyridine, or a solid non-nucleophilic base such as, for example, sodium hydride, or 3-aminoacetyl-1-(tert-butoxycarbonyl)-indole hydrochloride, which may be prepared as described in Step (e) above, (0.01 mol), optionally in the presence of from 2 to 4 mol equivalents of said non-nucleophilic bases, in a solvent such as dichloromethane or ethyl acetate, is stirred. A suitable reagent such as, for example, 1 mol equivalent of phosgene or 0.33 mol equivalents of triphosgene is added. After stirring for from 10 minutes to about 24 hours, the mixture is diluted with up to an equal volume of a diluent such as diethyl ether or ethyl acetate (preferred diluent is diethyl ether), and any precipitates are filtered off. The filter cake is washed with additional diluent. The filtrate and washings are combined and rotary evaporated to give 2-(1-tert-butoxycarbonyl-indol-3-yl)-2-oxo-ethylisocyanate, which may be purified, if needed or desired, by vacuum distillation.

Step (g): Preparation of 2-[1-(tert-butoxycarbonyl)-indol-3-yl)-2-oxo-ethyl]carbamic Acid, [3-(3-methyl-but-2-en-1-yl)aminocarbonyl-2,3-dihydrothiazol-2-on-5-yl] Ester To a stirred solution of 3-(3-methyl-but-2-en-1-yl) aminocarbonyl-2,4-thiazolidinedione (0.01 mol), which may be prepared as described in Step (a) above, in a solvent such as, for example, THF is added 1 mol equivalent of a non-nucleophilic base such as described in Step (f) above, preferably sodium hydride, and the mixture is stirred for from 1 minute to about 1 hour. To the mixture is added a solution of 2-(1-tert-butoxycarbonyl-indol-3-yl)-2-oxo-ethylisocyanate (0.01 mol), which may be prepared as described in Step (f) above, in a solvent such as, for example, THF. Reaction progress may be followed by TLC or HPLC. When a sufficient amount of desired product is formed, the mixture is partitioned between ethyl acetate and water, or optionally the mixture is first rotary evaporated, and the residue is so partitioned. The organic layer is washed with 0.01 M hydrochloric acid, water, brine, and dried over sodium sulfate. The mixture is rotary evaporated to give 2-[1-(tert-butoxycarbonyl)-indol-3-yl)-2-oxo-ethyl] carbamic acid, [3-(3-methyl-but-2-en-1-yl)aminocarbonyl-2,3-dihydrothiazol-2-on-5-yl] ester, which may be purified, if needed or desired, by chromatography on silica gel or crystallization.

Step (h): Preparation of [2-(1H-indol-3-yl)-2-oxo-ethyl]-carbamic Acid 3-(3-methyl-but-2-enylcarbamoyl)-2-oxo-2,3-dihydro-thiazol-5-yl Ester To a stirred solution of 2-[1-(tert-butoxycarbonyl)-indol-3-yl)-2-oxo-ethyl]carbamic acid, [3-(3-methyl-but-2-en-1-yl)aminocarbonyl-2,4-thiazolidinedion-5-yl] ester (0.01 mol), which may be prepared as described in Step (g) above, in dichloromethane or diethyl ether is added an excess of either hydrogen chloride gas or trifluoroacetic acid, and the mixture is stirred for from 1 minute to about 24 hours. Reaction progress may be followed by TLC or HPLC. When a sufficient amount of desired product is formed, the mixture is partitioned between ethyl acetate and water, or optionally the mixture is first rotary evaporated, and the residue is so partitioned. The organic layer is washed with brine, dried over sodium sulfate, and rotary evaporated to give [2-(1H-indol-3-yl)-2-oxo-ethyl]-carbamic acid 3-(3-methyl-but-2-enylcarbamoyl)-2-oxo-2,3-dihydro-thiazol-5-yl ester, which may be purified, if needed or desired, by chromatography on silica gel or crystallization.

EXAMPLE 18

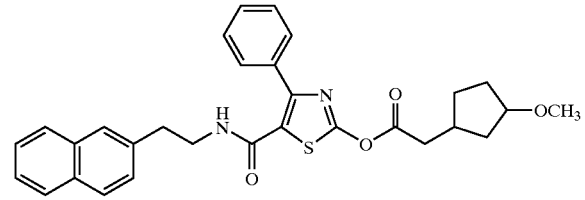

3-Methoxy-cyclopentylmethylcarboxylic Acid 5-(2-naphthalen-2-yl-ethylcarbamoyl)-4-phenyl-thiazol-2-yl Ester Step (a): Preparation of Thiocarbamic Acid, Benzyl Ester To a stirred solution of 1,1'-thiocarbonyldiimidazole (0.01 mol), in THF is added sodium benzyloxide (0.01 mol), and the mixture is stirred for from 1 minute to about 24 hours. To the mixture is added ammonia gas, and the mixture is stirred at atmospheric pressure or shaken at from atmospheric pressure to about 75 psi. Reaction progress may be followed by TLC or HPLC. (Alternatively, the imidazolyl leaving groups may be first activated (sequentially) by sulfonylation on nitrogen by pretreatment before each displacement with a suitable sulfonylating reagent such as trifluoromethanesulfonyl chloride or para-toluenesulfonyl chloride. This allows displacement of imidazolyl under less rigorous reaction conditions.) When a sufficient amount of desired product is formed, the mixture is partitioned between ethyl acetate and water, or optionally the mixture is first rotary evaporated, and the residue is so partitioned. The organic layer is washed with brine, dried over sodium sulfate, and rotary evaporated to give thiocarbamic acid, benzyl ester, which may be purified, if needed or desired, by chromatography on silica gel or crystallization.

Step (b): Preparation of 2-benzyloxy-4-phenyl-thiazol-5-carboxylic Acid, Ethyl Ester To a stirred solution of benzoylacetic acid, ethyl ester (0.01 mol) in a solvent such as, for example, chloroform is added N-bromosuccinimide (NBS, 0.01 mol), and the mixture is stirred. Reaction progress may be followed by TLC or HPLC. When a sufficient amount of benzoyl-bromoacetic acid, ethyl ester is formed, ethyl acetate is added, and the mixture is rotary evaporated to remove chloroform. To the resulting ethyl acetate mixture is added thiocarbamic acid, benzyl ester, which may be prepared as described in Step (a) above, and a suitable non-nucleophilic base such as those described in Example 17 above, and the mixture is stirred. Reaction progress may be followed by TLC or HPLC. When a sufficient amount of the desired product is formed, the reaction is washed with 0.01 M hydrochloric acid, water, brine, and dried over sodium sulfate. The mixture is rotary evaporated to give 2-benzyloxy-4-phenyl-thiazol-5-carboxylic acid, ethyl ester, which may be purified, if needed or desired, by chromatography on silica gel or crystallization.

Step (c): Preparation of 4-phenyl-thiazol-2-one-5-carboxylic Acid, Ethyl Ester

To a stirred solution of 2-benzyloxy-4-phenyl-thiazol-5-carboxylic acid, ethyl ester (0.01 mol) in a solvent such as THF is added a suitable hydrogenation catalyst such as 10% palladium on carbon. The mixture is shaken under a hydrogen atmosphere at a pressure of from atmospheric pressure to about 75 psi. Reaction progress may be followed by TLC or HPLC. When a sufficient amount of the desired product is formed, the mixture is rotary evaporated to give 4-phenyl-thiazol-2-one-5-carboxylic acid, ethyl ester, which may be purified, if needed or desired, by chromatography on silica gel or crystallization. Alternatively, to a stirred solution of 2-benzyloxy-4-phenyl-thiazol-5-carboxylic acid, ethyl ester (0.01 mol) in a solvent such as dichloromethane is added a suitable ether-cleaving reagent such as boron tribromide, and the mixture is stirred. Reaction progress may be followed by TLC or HPLC. When a sufficient amount of the desired product is formed, the mixture is washed with 0.01 M sodium bicarbonate, water, brine, and dried over sodium sulfate. The mixture is rotary evaporated to give 4-phenyl-thiazol-2-one-5-carboxylic acid, ethyl ester, which may be purified, if needed or desired, by chromatography on silica gel or crystallization.

Step (d): Preparation of (±)-2-(3-methoxycyclopentylmethylcarboxy)-4-phenyl-thiazol-5-carboxylic Acid, Ethyl Ester To a stirred solution of give 4-phenyl-thiazol-2-one-5-carboxylic acid, ethyl ester (0.01 mol), which may be prepared as described above in Step (c), in a solvent such as THF is added a suitable non-nucleophilic base such as those described above in Example 17, followed by addition of (±)-3-methoxycyclopentylmethylcarbonyl chloride, and the mixture is stirred. Reaction progress may be followed by TLC or HPLC. When a sufficient amount of the desired product is formed, the mixture is partitioned between ethyl acetate and 0.01 M sodium bicarbonate. The organic layer is washed with water, brine, and dried over sodium sulfate. The mixture is rotary evaporated to give (±)-2-(3-methoxycyclopentylmethylcarboxy)-4-phenyl-thiazol-5-carboxylic acid, ethyl ester, which may be purified, if needed or desired, by chromatography on silica gel or crystallization.

Step (e): Preparation of (±)-2-(3-methoxycyclopentylmethylcarboxy)-4-phenyl-thiazol-5-carboxylic Acid To a stirred solution of (±)-2-(3-methoxycyclopentylmethylcarboxy)-4-phenyl-thiazol-5-carboxylic acid, ethyl ester (0.01 mol), which may be prepared as described in Step (d) above, in a solvent such as ethanol, aqueous ethanol, or THF-ethanol, is added a solution of sodium or potassium hydroxide in ethanol at a concentration of from 1 M to about 2 M, and the mixture is stirred. Reaction progress may be followed by TLC or HPLC. When a sufficient amount of the desired product is formed, the mixture is rotary evaporated to remove most of the organic solvents, and the concentrated mixture is washed with ethyl acetate. The aqueous layer is acidified with hydrochloric acid to a pH of about 2 to about 4, and the product which precipitates is filtered off to give (±)-2-(3-methoxycyclopentylmethylcarboxy)-4-phenyl-thiazol-5-carboxylic acid, which may be purified, if needed or desired, by chromatography on silica gel or crystallization.

Step (f): 3-Methoxy-cyclopentylmethylcarboxylic Acid 5-(2-naphthalen-2-yl-ethylcarbamoyl)-4-phenyl-thiazol-2-yl Ester To a stirred solution of (±)-2-(3-methoxycyclopentylmethylcarboxy)-4-phenyl-thiazol-5-carboxylic acid (0.01 mol), which may be prepared as described above in Step (e), in a solvent such as THF is added 1,1'-carbonyldiimidazole, and the mixture is stirred from 10 minutes to about 24 hours. To this mixture is added naphth-2-ylethyl amine (0.01 mol), and the mixture is stirred. Reaction progress may be followed by TLC or HPLC. When a sufficient amount of the desired product is formed, the mixture is rotary evaporated. The residue is partitioned between ethyl acetate and 0.01 M sodium hydroxide, and the organic layer is washed with water, brine, and dried over sodium sulfate. The mixture is rotary evaporated to give 3-methoxy-cyclopentylmethylcarboxylic acid 5-(2-naphthalen-2-yl-ethylcarbamoyl)-4-phenyl-thiazol-2-yl ester, which may be purified, if needed or desired, by chromatography on silica gel or crystallization. Alternatively, the (±)-2-(3-methoxycyclopentylmethylcarboxy)-4-phenyl-thiazol-5-carboxylic acid and naphth-2-ylethyl amine may be combined in a solvent such as THF and a coupling reagent such as dicyclohexylcarbodiimide (DCC) added to give the title compound. Alternatively, especially in the case where the starting carboxylic acid or amine is poorly soluble in non-polar solvents such as THF, the reaction may be run in aqueous organic solvents using a water soluble carbodiimide coupling reagent.

EXAMPLE 19

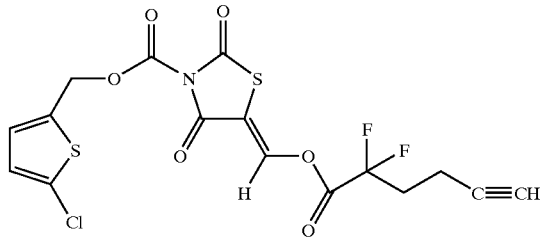

(E)-5-(2,2-Difluoro-hex-5-ynoyloxymethylene)-2,4-dioxo-thiazolidine-3-carboxylic acid 5-chloro-thiophen-2-ylmethyl Ester Step (a): Preparation of 2,4-dimethoxythiazole To a stirred solution of 2,4-thiazolidindione (0.01 mol) in a solvent such as THF is added from 2 to 4 mol equivalents of a non-nucleophilic base such as sodium hydride or LDA, followed by methyl iodide, and the mixture is stirred. Reaction progress may be followed by TLC or HPLC. When a sufficient amount of the desired product is formed, the mixture is partitioned between ethyl acetate and water. The organic layer is washed with brine, dried over sodium sulfate, and rotary evaporated to give 2,4-dimethoxythiazole, which may be purified, if needed or desired, by chromatography on silica gel or crystallization.

Step (b): Preparation of 2,4-dimethoxythiazole-5-carboxaldehyde

To a stirred solution of 2,4-dimethoxythiazole (0.01 mol), which may be prepared as described in Step (a) above, in dichloromethane is added N-phenyl-N-methylformamide (0.01 mol) and phosphorous oxychloride (POCl$_3$, 0.01 mol), or optionally phosgene or trifluoromethanesulfonic acid anhydride instead of POCl$_3$, and the mixture is stirred. Reaction progress may be followed by TLC or HPLC. When a sufficient amount of the desired product is formed, the mixture is partitioned between ethyl acetate and water. The organic layer is washed with brine, dried over sodium sulfate, and rotary evaporated to give 2,4-dimethoxythiazole-5-carboxaldehyde, which may be purified, if needed or desired, by chromatography on silica gel or crystallization.

Step (c): Preparation of (E)-5-(2,2-difluoro-hex-5-ynoyloxymethylene)-2-methoxy-4,5-dihydro-thiazolin-4-one To a stirred solution of 2,4-dimethoxythiazole-5-carboxaldehyde (0.01 mol), which may be prepared as described in Step (b) above, in a solvent such as dichloromethane is added phosphorous tribromide or another suitable ether cleaving reagent, and the mixture is stirred. Reaction progress may be followed by TLC or HPLC. When a sufficient amount of the corresponding 2,4-thiazolidindione-5-carboxaldehyde is formed, the reaction is partitioned between ethyl acetate and water. The organic layer is washed with brine, dried over sodium sulfate, and rotary evaporated. The residue is dissolved in THF, and 1 mol equivalent of a suitable non-nucleophilic base as described in Example 17 is added, followed by 1 mol equivalent of methyl iodide. Reaction progress may be followed by TLC or HPLC. When a sufficient amount of the corresponding 2-methoxy-4,5-dihydro-thiazolin-4-one-5-carboxaldehyde is formed, the mixture is partitioned and worked up as described above. The resulting residue is dissolved in THF, and 1 mol equivalent of a suitable non-nucleophilic base as described in Example 17 is added, followed by 1 mol equivalent of 2,2-difluoro-hex-5-ynoyl chloride, and the mixture is stirred. Reaction progress may be followed by TLC or HPLC. When a sufficient amount of the desired product is formed, the reaction is partitioned and worked up as described above to give (E)-5-(2,2-difluoro-hex-5-ynoyloxymethylene)-2-methoxy-4,5-dihydro-thiazolin-4-one, which may be purified, if needed or desired, by chromatography on silica gel or crystallization. Also formed is (Z)-5-(2,2-difluoro-hex-5-ynoyloxymethylene)-2-methoxy-4,5-dihydro-thiazolin-4-one, which may be purified, if needed or desired, by chromatography on silica gel or crystallization.

Step (d): Preparation of (E)-5-(2,2-difluoro-hex-5-ynoyloxymethylene)-2,4-thiazolidindione To a stirred solution of (E)-5-(2,2-difluoro-hex-5-ynoyloxymethylene)-2-methoxy-4,5-dihydro-thiazolin-4-one (0.01 mol), which may be prepared as described in Step (c) above, in dichloromethane is added phosphorous tribromide or another suitable ether cleaving reagent, and the mixture is stirred. Reaction progress may be followed by TLC or HPLC. When a sufficient amount of the desired product is formed, the reaction is partitioned and worked up as described in Step (c) above to give (E)-5-(2,2-difluoro-hex-5-ynoyloxymethylene)-2,4-thiazolidindione, which may be purified, if needed or desired, by chromatography on silica gel or crystallization.

Step (e): Preparation of (E)-5-(2,2-difluoro-hex-5-ynoyloxymethylene)-2,4-dioxo-thiazolidine-3-carboxylic Acid 5-chloro-thiophen-2-ylmethyl Ester To a stirred solution of (E)-5-(2,2-difluoro-hex-5-ynoyloxymethylidenyl)-2,4-thiazolidindione, which may be prepared as described in Step (d) above, in THF is added 2 mol equivalents of a non-nucleophilic base such as one of those described above in Example 17, followed by 1 mol equivalent of phosgene or 0.33 mol equivalents of triphosgene, and the mixture is stirred. After stirring for from 1 minute to about 1 hour, 5-chlorothiophen-2-ylmethyl alcohol is added, and the mixture is stirred. Reaction progress may be followed by TLC or HPLC. When a sufficient amount of the desired product is formed, the reaction is partitioned between ethyl acetate and water. The organic layer is washed with 0.01 M sodium bicarbonate, water, brine, and dried over sodium sulfate. The mixture is rotary evaporated to give (E)-5-(2,2-difluoro-hex-5-ynoyloxymethylene)-2,4-dioxo-thiazolidine-3-carboxylic acid 5-chloro-thiophen-2-ylmethyl ester, which may be purified, if needed or desired, by chromatography on silica gel or crystallization.

EXAMPLE 20

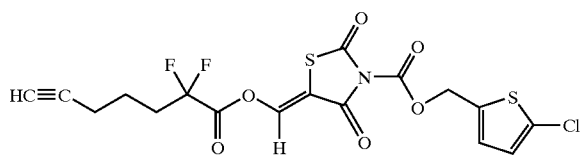

(Z)-5-(2,2-Difluoro-hex-5-ynoyloxymethylene)-2,4-dioxo-thiazolidine-3-carboxylic Acid 5-chloro-thiophen-2-ylmethyl Ester In a manner similar to Example 19, Steps (d) and (e), (Z)-5-(2,2-difluoro-hex-5-ynoyloxymethylene)-2-methoxy-4,5-dihydro-thiazolin-4-one, prepared according to the procedure described above in Example 19, Step (c), is converted to (Z)-5-(2,2-difluoro-hex-5-ynoyloxymethylene)-2,4-dioxo-thiazolidine-3-carboxylic acid 5-chloro-thiophen-2-ylmethyl ester, which may be purified, if needed or desired, by chromatograph on silica gel or crystallization.

EXAMPLE 21

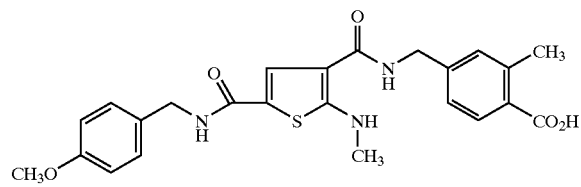

4-({[5-(4-Methoxy-benzylcarbamoyl)-2-methylamino-thiophene-3-carbonyl]-amino}-methyl)-2-methyl-benzoic Acid An amount (0.0863 g, 0.000170 mol) of the compound of Formula (Z)

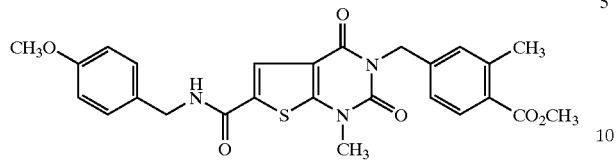

(Z)

and potassium carbonate (0.0773 g, 0.000559 mol) in a mixture of water (3 mL) and methanol (3 mL) was heated to reflux under nitrogen for 24 hours. After cooling to room temperature, the mixture was acidified with concentrated hydrochloric acid. A solid was filtered off and dried in vacuo to yield 0.078 g of 4-({[5-(4-methoxy-benzylcarbamoyl)-2-methylamino-thiophene-3-carbonyl]-amino}-methyl)-2-methyl-benzoic acid as a white powder; MS-APCI$^+$ (M+1): 468.2; Elem. Anal. Calc'd for $C_{24}H_{25}N_3O_5S$ 1.17 $H_2O$: C, 58.99; H, 5.64; N, 8.60; S, 6.56. Found: C, 58.61; H, 5.44; N, 8.52; S, 6.87.

EXAMPLE 22

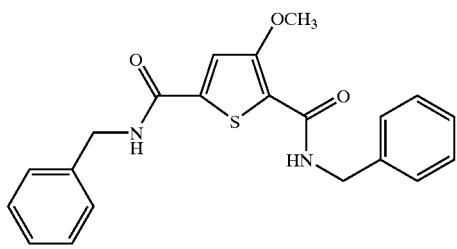

3-Methoxy-thiophene-2,5-dicarboxylic Acid Bis Benzylamide

A mixture of 3-methoxy-thiophene-2,5-dicarboxylic acid (0.382 g), benzylamine (0.41 mL), N,N'-carboxyl≈diimidazole (0.66 g), and DMF was heated at 60° C. to yield 0.39 g of 3-methoxy-thiophene-2,5-dicarboxylic acid bis benzylamide; MI-APCI$^+$ 381.1; Elem. Anal. ($C_{21}H_{20}N_2O_3S$); Calc'd: C, 66.30; H, 5.30; N, 7.36. Found: C, 66.52; H, 5.06; N, 7.41.

EXAMPLE 23

5-(3-Benzyl-ureido)-1,3,4-thiadiazole-2-carboxylic Acid Benzyl Ester

Step (a): Acrylic Acid Benzyl Ester

To a solution of benzyl alcohol (4.76 mL, 0.046 mol), 4-dimethylamino-pyridine ("DMAP," 0.790 g, 0.0065 mol) and triethylamine (12.85 mL, 0.09297 mol) in dichloromethane (92 mL) was added a solution of acryloyl chloride (7.54 mL, 0.09297 mol) slowly at 0° C., and the mixture was stirred at 0° C. for 2.5 hours. The mixture was quenched with aqueous sodium bicarbonate, and the quenched mixture was extracted with dichloromethane (2×100 mL). The extracts were combined, dried ($MgSO_4$), and rotary evaporated to give a yellow oil. The oil was purified by column chromatography, eluting with hexanes/ethyl acetate (95:5) to give 5.19 g (64%) of acrylic acid benzyl ester as a clear oil.

Step (b): Benzyl Glyoxalate

To a clear solution of the product of Step (a) (1 g, 0.006 mol) in water and dioxane was added osmium tetroxide (0.0216 g, 0.0000851 mol). After 5 minutes the clear solution had turned dark brown. Sodium periodate (2.43 g, 0.0114 mol) was added portionwise over 0.5 hour, and the mixture was stirred for 3 hours. The resulting cream-colored suspension was filtered. The filtrate was extracted with ethyl ether (3×50 mL). The extracts were combined, dried ($MgSO_4$), and rotary evaporated to give a dark brown oil; yield 0.92 g (99%), which was benzyl glyoxalate.

Step (c):

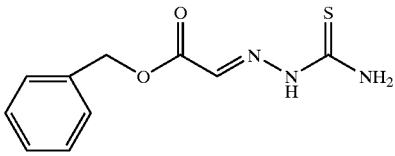

To a solution of acetic acid was added N-aminothiourea (0.555 g), and the mixture was heated at 80° C. until the yellow mixture became homogeneous. The temperature was lowered to 50° C., and the product of Step (b) (1 g, 0.006 mol) was added dropwise. After addition was complete, the heat was turned off, and the mixture stirred overnight at room temperature. After 24 hours, the mixture was filtered, and the filtercake was washed with acetic acid (5 mL), then cold water (2×5 mL). The resulting cream-colored filtercake was the Step (c) title compound according to $^1$H-NMR and MS; yield 0.8 g (55%).

Step (d): 5-Amino-1,3,4-thiadiazole-2-carboxylic Acid Benzyl Ester

To a solution of acetic acid was added the product of Step (c) (0.1 g, 0.00042 mol) followed by a solution of iron (III) chloride in water, after dissolving the iron (III) chloride completely in water at 50° C. The mixture was stirred at room temperature for 1 hour, then ice and water were added, and the mixture was stirred vigorously. After 5 minutes, the mixture was filtered to give a white powder. Additional solids were obtained by concentrating the filtrate and diluting the concentrated filtrate with water. Total yield 0.05 g of 5-amino-1,3,4-thiadiazole-2-carboxylic acid benzyl ester; mp 198–200° C.

Step (e): 5-(3-Benzyl-ureido)-1,3,4-thiadiazole-2-carboxylic Acid Benzyl Ester

To a solution of the product of Step (d) (0.1 g, 0.000425 mol) in THF (6.07 mL) was added benzyl isocyanate (0.0525 mL, 0.000425 mol), and the mixture was stirred overnight at room temperature. After 24 hours, the mixture was rotary evaporated and the concentrate was diluted with ethyl ether and dichloromethane. A solid was filtered and washed with ethyl ether. The mother filtrate was rotary evaporated and the residue triturated with ethyl ether and dichloromethane to give additional solids. The solids were combined to give 0.12 g of 5-(3-benzyl-ureido)-1,3,4-thiadiazole-2-carboxylic acid benzyl ester; mp 188–192° C.

The invention compounds of Formula I have been evaluated in standard assays for their ability to inhibit the activity of various MMP enzymes. The assays used to evaluate the biological activity of the invention compounds are well known and routinely used by those skilled in the study of MMP inhibitors and their use to treat clinical conditions.

The assays measure the amount by which a test compound inhibits the hydrolysis of a thiopeptolide substrate caused by a matrix metalloproteinase enzyme. Such assays are described in detail by Ye et al., in *Biochemistry*, 1992;31 (45):11231–11235, which is incorporated herein by reference.

Thiopeptolide substrates show virtually no decomposition or hydrolysis in the absence of a matrix metalloproteinase enzyme. A typical thiopeptolide substrate commonly utilized for assays is Ac-Pro-Leu-Gly-thioester;-Leu-Leu-Gly-OEt. A 100 µL assay mixture will contain 50 mM of 2-morpholinoethane sulfonic acid monohydrate (MES, pH 6.0) 10 mM $CaCl_2$, 100 µM thiopeptolide substrate, and 1 mM 5,5'-dithio-bis-(2-nitro-benzoic acid) (DTNB). The thiopeptolide substrate concentration is varied from 10 to 800 µM to obtain Km and Kcat values. The change in absorbance at 405 nm is monitored on a Thermo Max microplate reader (Molecular Devices, Menlo Park, Calif.) at room temperature (22° C.). The calculation of the amount of hydrolysis of the thiopeptolide substrate is based on $E_{412}=13600$ $m^{-1}$ $cm^{-1}$ for the DTNB-derived product 3-carboxy-4-nitrothiophenoxide. Assays are carried out with and without matrix metalloproteinase inhibitor compounds, and the amount of hydrolysis is compared for a determination of inhibitory activity of the test compounds.

Several representative compounds have been evaluated for their ability to inhibit various matrix metalloproteinase enzymes. The invention compounds are uniquely active in inhibiting MMP-13. Table 1 below presents inhibitory activity for invention compounds in the column labelled "MMP-13CD $IC_{50}$, µM". In the table, MMP-13CD refers to the catalytic domain of collagenase-3. It has been shown previously (Ye Qi-Zhuang, Hupe D., Johnson L., *Current Medicinal Chemistry*, 1996;3:407–418) that inhibitor activity against a catalytic domain of an MMP is predictive of the inhibitor activity against the respective full-length enzyme. Test compounds were evaluated at various concentrations in order to determine their respective $IC_{50}$ values, the micromolar concentration of compound required to cause a 50% inhibition of the hydrolytic activity of the respective enzyme.

TABLE 1

| Compound of Example No. | MMP-13CD $IC_{50}$, µM |
|---|---|
| 1 | 8.6 |
| 2 | 0.85 |
| 3 | 3.6 |
| 4 | 0.20 |
| 5 | 0.45 |
| 6 | 0.37 |
| 7 | 0.97 |
| 8 | 3.0 |
| 9 | 2.3 |
| 10 | 30 |
| 11 | 0.19 |
| 12 | 2.7 |
| 13 | 22 |
| 14 | 14 |
| 15b | 0.92 |
| 16 | 2 |
| 21 | 3.4 |
| 22 | ≧100 |
| 23 | 30 |

The foregoing data in Table 1 establish that the invention compounds are potent inhibitors of MMP-13.

The invention compounds are also selective inhibitors of MMP-13 versus other MMP enzymes, including versus MMP-7 and MMP-9. This is shown by comparing the $IC_{50}$ data presented below in Table 2 in the columns labeled "MMP-7 $IC_{50}$ (µM)," "MMP-9CD $IC_{50}$ (µM)," and "MMP-13CD $IC_{50}$ (µM)," respectively.

TABLE 2

| Compound of Example No. | MMP-7 $IC_{50}$ (µM) | MMP-9CD $IC_{50}$ (µM) | MMP-13CD $IC_{50}$ (µM) |
|---|---|---|---|
| 1 | 100 | 100 | 8.6 |
| 2 | 30 | 30 | 0.85 |
| 3 | 100 | 100 | 3.6 |
| 4 | 30 | 100 | 0.20 |
| 5 | 10 | 30 | 0.45 |
| 6 | 32 | 100 | 0.37 |
| 7 | 100 | 100 | 0.97 |
| 8 | 100 | 100 | 3.0 |
| 9 | 100 | 100 | 2.3 |
| 10 | 100 | 30 | 30 |
| 11 | 100 | 100 | 0.19 |
| 12 | 100 | 100 | 2.7 |
| 13 | 30 | 30 | 22 |
| 14 | 100 | 99 | 14 |
| 15a | N/A[a] | N/A | 0.35 |
| 15b | 45 | 30 | 0.92 |
| 16 | 100 | 100 | 2 |

[a]N/A means datum not available.

The foregoing data establish that the invention compounds of Formula I are potent inhibitors of MMP enzymes, and are especially useful due to their selective inhibition of MMP-13. Because of this potent and selective inhibitory activity, the invention compounds are especially useful to treat diseases mediated by the MMP enzymes, and particularly those mediated by MMP-13.

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Also, the compounds of the present invention can be administered by inhalation, for example, intranasally. Additionally, the compounds of the present invention can be administered transdermally. It will be obvious to those skilled in the art that the following dosage forms may comprise as the active component, either a compound of Formula I or a corresponding pharmaceutically acceptable salt of a compound of Formula I. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, preferably 10 mg to 100 mg according to the particular application and the potency of the active component. The composition can, if desired, also contain other compatible therapeutic agents.

In therapeutic use as agents to inhibit a matrix metalloproteinase enzyme for the treatment of atherosclerotic plaque rupture, aortic aneurism, heart failure, restenosis, periodontal disease, corneal ulceration, cancer metastasis, tumor angiogenesis, arthritis, or other autoimmune or inflammatory disorders dependent upon MMP-mediated breakdown of connective tissue, the compounds utilized in the pharmaceutical method of this invention are administered at a dose that is effective to inhibit the hydrolytic activity of one or more matrix metalloproteinase enzymes. The initial dosage of about 1 mg to about 100 mg per kilogram daily will be effective. A daily dose range of about 25 mg to about 75 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstance is reached. For convenience, the total daily dosage may be divided and administered in portions during the day if desired. Typical dosages will be from about 0.1 to about 500 mg/kg, and ideally about 25 to about 250 mg/kg, such that it will be an amount which is effective to treat the particular disease being prevented or controlled.

The following examples illustrate pharmaceutical compositions of the present invention. The examples are representative only, and are not to be construed as limiting the invention in any respect.

Formulation Example 1

| Tablet Formulation: | |
|---|---|
| Ingredient | Amount (mg) |
| The compound of Example 1 | 25 |
| Lactose | 50 |
| Cornstarch (for mix) | 10 |
| Cornstarch (paste) | 10 |
| Magnesium stearate (1%) | 5 |
| Total | 100 |

The compound of Example 1, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of disease caused by overactivity of matrix metalloproteinases.

Formulation Example 2

Coated Tablets:

The tablets of Formulation Example 1 are coated in a customary manner with a coating of sucrose, potato starch, talc, tragacanth, and colorant.

Formulation Example 3

Injection Vials:

The pH of a solution of 500 g of the compound of Example 4 and 5 g of disodium hydrogen phosphate is adjusted to pH 6.5 in 3 L of double-distilled water using 2 M hydrochloric acid. The solution is sterile filtered, and the filtrate is filled into injection vials, lyophilized under sterile conditions, and aseptically sealed. Each injection vial contains 25 mg of the compound of Example 4.

Formulation Example 4

Suppositories:

A mixture of 25 g of the compound of Example 6, 100 g of soya lecithin, and 1400 g of cocoa butter is fused, poured into molds, and allowed to cool. Each suppository contains 25 mg of the compound of Example 6.

Formulation Example 5

Solution:

A solution is prepared from 1 g of the compound of Example 5, 9.38 g of $NaH_2PO_4 \cdot 12H_2O$, 28.48 g of $Na_2HPO_4 \cdot 12H_2O$, and 0.1 g benzalkonium chloride in 940 mL of double-distilled water. The pH of the solution is adjusted to pH 6.8 using 2 M hydrochloric acid. The solution is diluted to 1.0 L with double-distilled water, and sterilized by irradiation. A 25 mL volume of the solution contains 25 mg of the compound of Example 5.

Formulation Example 6

Ointment:
500 mg of the compound of Example 2 is mixed with 99.5 g of petroleum jelly under aseptic conditions. A 5 g portion of the ointment contains 25 mg of the compound of Example 2.

Formulation Example 7

Capsules:
2 kg of the compound of Example 3 are filled into hard gelatin capsules in a customary manner such that each capsule contains 25 mg of the invention compound.

Formulation Example 8

Ampoules:
A solution of 2.5 kg of the compound of Example 8 is dissolved in 60 L of double-distilled water. The solution is sterile filtered, and the filtrate is filled into ampoules. The ampoules are lyophilized under sterile conditions and aseptically sealed. Each ampoule contains 25 mg of the compound of Example 8.

Having described the present invention above, certain embodiments of the present invention are hereupon claimed.

What is claimed is:

1. A compound of Formula II

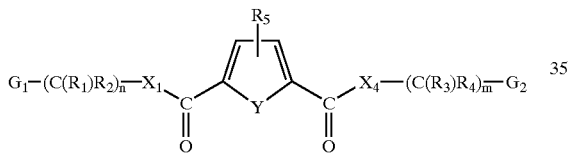

II or a pharmaceutically acceptable salt thereof;
wherein:
Y is S;
$X_1$ and $X_4$ are each independently NH;
$G_1$ and $G_2$ are independently phenyl or substituted phenyl;
$R_1$, $R_2$, $R_3$, and $R_4$ are independently, at each occurrence,
  hydrogen,
  methyl,
  cyano, and
  fluoro, or $R_1$, and $R_2$, or $R_3$ and $R_4$, may be taken together with the carbon atom to which they are each attached to form C=O; and
n and m are independently an integer of from 1 to 3;
$R_5$ is selected from;
  hydrogen,
  $C_1$–$C_{12}$ alkyl,
  substituted $C_1$–$C_{12}$ alkyl,
  $C_2$–$C_{12}$ alkenyl,
  substituted $C_2$–$C_{12}$ alkenyl,
  $C_2$–$C_{12}$ alkynyl,
  substituted $C_2$–$C_{12}$ alkynyl,
  $C_3$–$C_{12}$ cycloalkyl,
  substituted $C_3$–$C_{12}$ cycloalkyl,
  phenyl,
  substituted phenyl,
  benzyl,
  substituted benzyl,
  O—$R_6$, wherein $R_6$ is hydrogen, $C_1$–$C_{12}$ alkyl, phenyl, or benzyl,
  S—$R_6$, wherein $R_6$ is hydrogen, $C_1$–$C_{12}$ alkyl, phenyl, or benzyl,
  C(O)—$R_6$, wherein $R_6$ is hydrogen, $C_1$–$C_{12}$ alkyl, phenyl, or benzyl,
  $CO_2R_6$, wherein $R_6$ is hydrogen, $C_1$–$C_{12}$ alkyl, phenyl, or benzyl,
  C(O)—N(H)OH,
  C(=NOR$_6$)—H, wherein $R_6$ is hydrogen, $C_1$–$C_{12}$ alkyl, phenyl, or benzyl,
  C(=NOR$_6$)—$CH_3$, wherein $R_6$ is hydrogen, $C_1$–$C_{12}$ alkyl, phenyl, or benzyl,
  $CH_2OR_6$, wherein $R_6$ is hydrogen, $C_1$–$C_{12}$ alkyl, phenyl, or benzyl,
  $CH_2N(R_6)R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A)

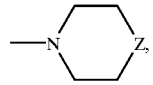

(A)

wherein Z is $CH_2$, O, S, or N—R, wherein R is H or $CH_3$,
C(H)F—OH,
$CF_2$—OH,
O—C(O)—$R_6$, wherein $R_6$ is hydrogen, $C_1$–$C_{12}$ alkyl, phenyl, or benzyl,
C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
N($R_6$)—C(O)—$R_7$, wherein $R_6$ and $R_7$ are independently hydrogen, $C_1$–$C_{12}$ alkyl, phenyl, or benzyl,
N(H)—C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
N(H)—C(O)—$OR_6$, wherein $R_6$ is independently hydrogen, $C_1$–$C_{12}$ alkyl, phenyl, or benzyl, N(H)—S(O)$_2$—($C_1$–$C_{12}$ alkyl),
O—C(O)—N($R_6$)$R_7$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, $NO_2$, $N_3$, N(H)—C($NR_8$)—N($R_6$)$R_7$, wherein $R_6$ and $R_7$ are independently hydrogen, $C_1$–$C_4$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and $R_8$ is hydrogen, hydroxy, methoxy, or CN,

CN, halo,

S(O)—($C_1$–$C_{12}$ alkyl), $S(O)_2$—($C_1$–$C_{12}$ alkyl), $S(O)_2$—N($R_6$)—($R_7$), wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and $S(O)_2CF_3$, wherein at least one of $R_1$, $R_2$, $R_3$, $R_4$, or $R_5$ is not hydrogen, or at least one of $G_1$ or $G_2$ is substituted phenyl;

wherein substituents for substituted phenyl and substituted benzyl are 1 to 4 substituents independently selected from:

$C_1$–$C_{12}$ alkyl, $C_2$–$C_{12}$ alkenyl, $C_2$–$C_{12}$ alkynyl, $C_3$–$C_{12}$ cycloalkyl, phenyl, benzyl, O—$R_z$, wherein $R_z$ is hydrogen, C 1–$C_{12}$ alkyl, phenyl, or benzyl, S—$R_z$, wherein $R_z$ is hydrogen, $C_1$–$C_{12}$ alkyl, phenyl, or benzyl, 1,2-methylenedioxy, C(O)—$R_z$, wherein $R_z$ is hydrogen, $C_1$–$C_{12}$ alkyl, phenyl, or benzyl, $CO_2R_z$, wherein $R_z$ is hydrogen, $C_1$–$C_{12}$ alkyl, phenyl, or benzyl, C(O)—N(H)$OR_z$, wherein $R_z$ is hydrogen, $C_1$–$C_{12}$ alkyl, phenyl, or benzyl, C(=$NOR_z$)—H, wherein $R_z$ is hydrogen, $C_1$–$C_{12}$ alkyl, phenyl, or benzyl, C(=$NOR_z$)—$CH_3$, wherein $R_z$ is hydrogen, $C_1$–$C_{12}$ alkyl, phenyl, or benzyl, $CH_2OR_z$, wherein $R_z$ is hydrogen, $C_1$–$C_{12}$ alkyl, phenyl, or benzyl, $CH_2$N($R_z$)$R_y$, wherein $R_z$ and $R_y$ are independently hydrogen, $C_1$–$C_{12}$ alkyl, phenyl, or benzyl, or $R_z$ and are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,

C(H)F—OH, $CF_2$—OH,

O—C(O)—$R_z$, wherein $R_1$ is hydrogen, $C_1$–$C_{12}$ alkyl, phenyl, or benzyl, C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N($R_z$)—C(O)—$R_y$, wherein $R_z$ and $R_y$ are independently hydrogen, $C_1$–$C_{12}$ alkyl, phenyl, or benzyl, N(H)—C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(H)—C(O)—$OR_z$, wherein $R_z$ is independently hydrogen, $C_1$–$C_{12}$ alkyl, phenyl, or benzyl, N(H)—$S(O)_2$—($C_1$–$C_{12}$ alkyl), O—C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, $NO_2$, $N_3$, N(H)—C($NR_x$)—N($R_z$)$R_y$, wherein $R_z$ and $R_y$ are independently hydrogen, $C_1$–$C_4$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and $R_x$ is hydrogen, hydroxy, methoxy, or CN,

CN, halo,

S(O)—($C_1$–$C_{12}$ alkyl), $S(O)_2$—($C_1$–$C_{12}$ alkyl), $S(O)_2$—N($R_z$)—($R_y$), wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and $S(O)_2CF_3$; and wherein substituted $C_1$–$C_{12}$ alkyl, substituted $C_1$–$C_{12}$ alkenyl, substituted $C_2$–$C_{12}$ alkynyl, and substituted $C_3$–$C_{12}$ cycloalkyl are substituted with from 1 to 4 substituents independently selected from:

oxo,

O—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 3 substituents as described below, S—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, $CO_2R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—N(H)O$R_z$, wherein $R_z$ is hydrogen, $C_1$–$C_{12}$ alkyl, phenyl, or benzyl, C(=NO$R_z$)—H, wherein $R_z$ is hydrogen, $C_1$–$C_{12}$ alkyl, phenyl, or benzyl, C(=NO$R_z$)—$CH_3$, wherein $R_z$ is hydrogen, $C_1$–$C_{12}$ alkyl, phenyl, or benzyl,

C(H)F—OH,

O—C(O)—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below, C(O)—N($R_z$)$R_y$, wherein $R_z$ and $R_y$ are independently hydrogen, $C_1$–$C_4$ alkyl, $C_3$–$C_6$ cycloalkyl, phenyl, or benzyl, wherein phenyl and benzyl may be substituted with from 1 to 4 substituents as described below, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z)

wherein Y is $CH_2$, O, S, or N—R, wherein R is H or $CH_3$,

N($R_z$)$R_y$, and are independently hydrogen, $C_1$–$C_4$ alkyl, $C_3$–$C_6$ cycloalkyl, phenyl, or benzyl, wherein phenyl and benzyl may be substituted with from 1 to 4 substituents as described below, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N($R_z$)—C(O)—$R_y$, and are independently hydrogen, $C_1$–$C_4$ alkyl, $C_3$–$C_6$ cycloalkyl, phenyl, or benzyl, wherein phenyl and benzyl may be substituted with from 1 to 4 substituents as described below, N(H)—C(O)—N($R_z$)$R_y$, wherein $R_z$ and $R_y$ are independently hydrogen, $C_1$–$C_4$ alkyl, phenyl, or benzyl, wherein phenyl and benzyl may be substituted with from 1 to 4 substituents as described below, or $R_z$ and are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(H)—C(O)—O$R_z$, wherein $R_z$ is independently hydrogen, $C_1$–$C_4$ alkyl, $C_3$–$C_6$ cycloalkyl, phenyl, or benzyl, wherein phenyl and benzyl may be substituted with from 1 to 4 substituents as described below, O—C(O)—N($R_z$)$R_y$, wherein $R_z$ and $R_y$ are indenendently hydrogen, $C_1$–$C_4$ alkyl, $C_3$–$C_6$ cycloalkyl, phenyl, or benzyl, wherein phenyl and benzyl may be substituted with from 1 to 4 substituents as described below, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, $NO_2$, $N_3$, N(H)—C(N$R_x$)—N($R_z$)$R_y$, wherein $R_z$ and $R_y$ are independently hydrogen, $C_1$–$C_4$ alkyl, phenyl, or benzyl, wherein phenyl and benzyl may be substituted with from 1 to 4 substituents as described below, or and are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and $R_x$ is hydrogen, hydroxy, methoxy, or CN,

CN, halo,

S(O)—($C_1$–$C_4$ alkyl), $S(O)_2$—($C_1$–$C_4$ alkyl), $S(O)_2$—N($R_z$)$R_y$, and are independently hydrogen, $C_1$–$C_4$ alkyl, $C_3$–$C_6$ cycloalkyl, phenyl, or benzyl, wherein phenyl and benzyl may be substituted with from 1 to 4 substituents as described below, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and N(H)—$S(O)_2$—($C_1$–$C_4$ alkyl).

2. The compound according to claim 1, or a pharmaceutically acceptable salt thereof, wherein n and m are each 1.

3. The compound according to claim 1, or a pharmaceutically acceptable salt thereof, wherein $G_1$ and $G_2$ are independently substituted phenyl, wherein the substituents are selected from 1,2-methylenedioxy, methoxy, ethoxy, —O—C(O)$CH_3$, carboxy, carbomethoxy, and carboethoxy, and n and m are each 1.

4. The compound according to claim 1, or a pharmaceutically acceptable salt thereof, wherein:

n and m are each 1;

$G_1$ and $G_2$ are each

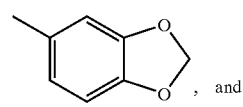, and $R_5$ is hydrogen or OMe.

5. The compound according to claim 1, or a pharmaceutically acceptable salt thereof, selected from:

thiophene-2,5-dicarboxylic acid, bis[(1,3-benzodioxol-5-ylmethyl)ester];

thiophene-2,5-dicarboxylic acid, bis[(1,3-benzodioxol-5-ylmethyl)amide];

thiophene-2,5-dicarboxylic acid, 3-methoxy-, bis[(1,3-benzodioxol-5-ylmethyl)ester]; and thiophene-2,5-dicarboxylic acid, 3-methoxy-, bis[(1,3-benzodioxol-5-ylmethyl)amide].

6. A compound of Formula III

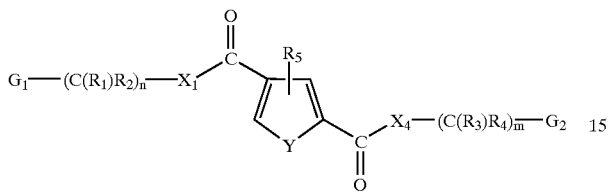

or a pharmaceutically acceptable salt thereof;
wherein:
n and m are each 1;
Y is S;
$X_1$ and $X_4$ are each independently NH;
$G_1$ and $G_2$ are independently phenyl or substituted phenyl;
$R_1, R_2, R_3,$ and $R_4$ are independently, at each occurrence, selected from:
 hydrogen,
 methyl,
 cyano, and
 fluoro, $R_1$ and $R_2$, or $R_3$ and $R_4$ may be taken together with the carbon atom to which they are each attached to form C=O;
$R_5$ is selected from:
 hydrogen,
 $C_1-C_{12}$ alkyl,
 substituted $C_1-C_{12}$ alkyl,
 $C_2-C_{12}$ alkenyl,
 substituted $C_2-C_{12}$ alkenyl,
 $C_2-C_{12}$ alkynyl,
 substituted $C_2-C_{12}$ alkynyl,
 $C_3-C_{12}$ cycloalkyl,
 substituted $C_3-C_{12}$ cycloalkyl,
 phenyl,
 substituted phenyl,
 benzyl,
 substituted benzyl,
 O—$R_6$, wherein $R_6$ is hydrogen, $C_1-C_{12}$ alkyl, phenyl, or benzyl,
 S—$R_6$, wherein $R_6$ is hydrogen, $C_1-C_{12}$ alkyl, phenyl, or benzyl,
 C(O)—$R_6$, wherein $R_6$ is hydrogen, $C_1-C_{12}$ alkyl, phenyl, or benzyl,
 $CO_2R_6$, wherein $R_6$ is hydrogen, $C_1-C_{12}$ alkyl, phenyl, or benzyl,
 C(O)—N(H)OH,
 C(=NOR$_6$)—H, wherein $R_6$ is hydrogen, $C_1-C_{12}$ alkyl, phenyl, or benzyl,
 C(=NOR$_6$)—CH$_3$, wherein $R_6$ is hydrogen, $C_1-C_{12}$ alkyl, phenyl, or benzyl,
 CH$_2$OR$_6$, wherein $R_6$ is hydrogen, $C_1-C_{12}$ alkyl, phenyl, or benzyl,
 CH$_2$N(R$_6$)R$_7$, wherein $R_6$ and $R_7$ are independently hydrogen, $C_1-C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A)

wherein Z is CH$_2$, O, S, or N—R, wherein R is H or CH$_3$,
 C(H)F—OH,
 CF$_2$—OH,
 O—C(O)—R$_6$, wherein $R_6$ is hydrogen, $C_1-C_{12}$ alkyl, phenyl, or benzyl,
 C(O)—N(R$_6$)R$_7$, wherein $R_6$ and $R_7$ are independently hydrogen, $C_1-C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
 N(R$_6$)R$_7$, wherein $R_6$ and $R_7$ are independently hydrogen, $C_1-C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
 N(R$_6$)—C(O)—R$_7$, wherein $R_6$ and $R_7$ are independently hydrogen, $C_1-C_{12}$ alkyl, phenyl, or benzyl,
 N(H)—C(O)—N(R$_6$)R$_7$, wherein $R_6$ and $R_7$ are independently hydrogen, $C_1-C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
 N(H)—C(O)—OR$_6$, wherein $R_6$ is independently hydrogen, $C_1-C_{12}$ alkyl, phenyl, or benzyl,
 N(H)—S(O)$_2$—($C_1-C_{12}$ alkyl),
 O—C(O)—N(R$_6$)R$_7$, wherein $R_6$ and $R_7$ are independently hydrogen, $C_1-C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above,
 NO$_2$,
 N$_3$,
 N(H)—C(NR$_8$)—N(R$_6$)R$_7$, wherein $R_6$ and $R_7$ are independently hydrogen, $C_1-C_4$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and $R_8$ is hydrogen, hydroxy, methoxy, or CN,
 CN,
 halo,
 S(O)—($C_1-C_{12}$ alkyl),
 S(O)$_2$—($C_1-C_{12}$ alkyl), $S(O)_2$—$N(R_6)$—$(R_7)$, wherein $R_6$ and $R_7$ are independently hydrogen, $C_1$–$C_{12}$ alkyl, phenyl, or benzyl, or $R_6$ and $R_7$ are taken together with the nitrogen atom to which they are attached to form a 5-membered, saturated heterocyclic ring having 1 nitrogen atom and 4 carbon atoms or a 6-membered, saturated heterocyclic ring of formula (A), wherein (A) is as defined above, and $S(O)_2CF_3$; and wherein at least one of $R_1$, $R_2$, $R_3$, $R_4$, or $R_5$ is not hydrogen, or at least one of G1 or G9 is substituted phenyl;

wherein substituents for substituted phenyl and substituted benzyl are 1 to 4 substituents independently selected from:

$C_1$–$C_{12}$ alkyl,
$C_1$–$C_{12}$ alkenyl,
$C_2$–$C_{12}$ alkynyl,
$C_3$–$C_{12}$ cycloalkyl,
phenyl,
benzyl,
O—$R_z$, is hydrogen, $C_1$–$C_{12}$ alkyl, phenyl, or benzyl,
S—$R_z$, wherein $R_z$ is hydrogen, $C_1$–$C_{12}$ alkyl, phenyl, or benzyl, 1,2-methylenedioxy,
C(O)—$R_z$, wherein $R_z$ is hydrogen, $C_1$–$C_{12}$ alkyl, phenyl, or benzyl,
$CO_2R_z$, wherein $R_z$ is hydrogen, $C_1$–$C_{12}$ alkyl, phenyl, or benzyl,
C(O)—N(H)O$R_z$, wherein $R_z$ is hydrogen, $C_1$–$C_{12}$ alkyl, phenyl, or benzyl,
C(=NO$R_z$)—H, wherein $R_z$ is hydrogen, $C_1$–$C_{12}$ alkyl, phenyl, or benzyl,
C(=NO$R_z$)—$CH_3$, wherein $R_z$ is hydrogen, $C_1$–$C_{12}$ alkyl, phenyl, or benzyl,
$CH_2OR_z$, wherein $R_z$ is hydrogen, $C_1$–$C_{12}$ alkyl, phenyl, or benzyl,
$CH_2N(R_z)R_y$, wherein $R_z$ and $R_y$ are independently hydrogen, $C_1$–$C_{12}$ alkyl, phenyl, or benzyl, or R and are taken together with the nitrogen atom to which they are attached to form a 5-membered, saturated heterocyclic ring having 1 nitrogen atom and 4 carbon atoms or a 6-membered, saturated heterocyclic ring of formula (Z), wherein Z) is as defined above,
C(H)F—OH,
$CF_2$—OH,
O—C(O)—$R_z$, wherein $R_z$ is hydrogen, $C_1$–$C_{12}$ alkyl, phenyl, or benzyl,
C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,
N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,
N($R_z$)—C(O)—$R_y$, wherein $R_z$ and $R_y$ are independently hydrogen, $C_1$–$C_{12}$ alkyl, phenyl, or benzyl,
N(H)—C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,
N(H)—C(O)—O$R_z$, wherein $R_z$ is independently hydrogen, $C_1$–$C_{12}$ alkyl, phenyl, or benzyl,
N(H)—$S(O)_2$—($C_1$–$C_{12}$ alkyl),
O—C(O)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,
$NO_2$,
$N_3$,
N(H)—C(N$R_x$)—N($R_z$)$R_y$, wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and $R_x$ is hydrogen, hydroxy, methoxy, or CN,
CN,
halo,
S(O)—($C_1$–$C_{12}$ alkyl),
$S(O)_2$—($C_1$–$C_{12}$ alkyl),
$S(O)_2$—N($R_z$)—($R_y$), wherein $R_z$ and $R_y$ are independently hydrogen, $C_1$–$C_{12}$ alkyl, phenyl, or benzyl, or $R_z$ and $R_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and $S(O)_2CF_3$; and wherein substituted $C_1$–$C_{12}$ alkyl, substituted $C_2$–$C_{12}$ alkenyl, substituted $C_2$–$C_{12}$ alkynyl, and substituted $C_3$–$C_{12}$ cycloalkyl are substituted with from 1 to 4 substituents independently selected from:
oxo,
O—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 3 substituents as described below,
S—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below,
C(O)—$R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below,
$CO_2R_z$, wherein $R_z$ is hydrogen, $C_1$–$C_4$ alkyl, $C_3$–$C_6$ cycloalkyl, phenyl, or benzyl, wherein phenyl and benzyl may be substituted with from 1 to 4 substituents as described below,
C(O)—N(H)O$R_z$, wherein $R_z$ is hydrogen, $C_1$–$C_{12}$ alkyl, phenyl, or benzyl,
C(=NO$R_z$)—H, wherein $R_z$ is hydrogen, $C_1$–$C_{12}$ alkyl, phenyl, or benzyl, C(=NOR$_z$)—CH$_3$, wherein R$_z$ is hydrogen, C$_1$–C$_{12}$ alkyl, phenyl, or benzyl,

C(H)F—OH,

O—C(O)—R$_z$, wherein R$_z$ is hydrogen, C$_1$–C$_4$ alkyl, C$_3$–C$_6$ cycloalkyl, phenyl, or benzyl, wherein phenyl and benzyl may be substituted with from 1 to 4 substituents as described below, C(O)—N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and are taken together with the nitrogen atom to which they are attached to form a 5-membered, saturated heterocyclic ring having 1 nitrogen atom and 4 carbon atoms or a 6-membered, saturated heterocyclic ring of formula (Z)

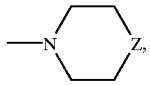

(A)

wherein Y is CH$_2$, O, S, or N—R, wherein R is H or CH$_3$,

N(R$_z$)R$_y$, and are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(R$_z$)—R$_y$, wherein R$_z$ and R$_y$ are independently hydrogen, C$_1$–C$_4$ alkyl, C$_3$–C$_6$ cycloalkyl, phenyl, or benzyl wherein phenyl and benzyl may be substituted with from 1 to 4 substituents as described below, N(H)—C(O)—N(R$_z$)R$_y$, wherein R$_z$ and R$_y$ are independently hydrogen, C$_1$–C$_4$ alkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, N(H)—C(O)—OR$_z$, wherein R$_z$ is independently hydrogen, C$_1$–C$_4$ alkyl, C$_3$–C$_6$ cycloalkyl, phenyl, or benzyl, wherein phenyl and benzyl may be substituted with from 1 to 4 substituents as described below, O—C(O)—N(R$_z$)R$_y$, wherein R$_z$ and R$_y$ are in dependently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above,

NO$_2$,

N$_3$,

N(H)—C(NR$_x$)—N(R$_z$)R$_y$, wherein R$_z$ and R$_y$ are independently hydrogen, C$_1$–C$_4$ alkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and R$_x$ is hydrogen, hydroxy, methoxy, or CN,

CN, halo,

S(O)—(C$_1$–C$_4$ alkyl),

S(O)$_2$—(C$_1$–C$_4$ alkyl),

S(O)$_2$—N(R$_z$)R$_y$, wherein R$_z$ and R$_y$ are independently hydrogen, C$_1$–C$_4$ alkyl, C$_3$–C$_6$ cycloalkyl, phenyl, or benzyl, wherein phenyl and benzyl may be substituted with from 1 to 4 substituents as described below, or R$_z$ and R$_y$ are taken together with the nitrogen atom to which they are attached to form a 5-membered, saturated heterocyclic ring having 1 nitrogen atom and 4 carbon atoms or a 6-membered, saturated heterocyclic ring of formula (Z), wherein (Z) is as defined above, and N(H)—S(O)$_2$—(C$_1$–C$_4$ alkyl).

7. The compound according to claim 6, a pharmaceutically acceptable salt thereof, wherein G$_1$ and G$_2$ are independently substituted phenyl.

8. The compound according to claim 6, or a pharmaceutically acceptable salt thereof, wherein G$_1$ and G$_2$ are independently substituted phenyl, wherein the substituents are selected from 1,2-methylenedioxy, methoxy, ethoxy, —O—C(O)CH$_3$, carboxy, carbomethoxy, and carboethoxy.

9. The compound according to claim 6, or a pharmaceutically acceptable salt thereof, wherein G$_1$ and G$_2$ are each

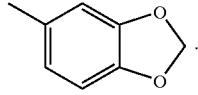

10. The compound according to claim 6, or a pharmaceutically acceptable salt thereof, selected from:

thiophene-2,4-dicarboxylic acid, bis[(1,3-benzodioxol-5-ylmethyl)ester];

thiophene-2,4-dicarboxylic acid, bis[(1,3-benzodioxol-5-ylmethyl)amide];

1H-pyrrole-2,4-dicarboxylic acid, 1-methyl-, bis[( 1,3-benzodioxol-5-ylmethyl)ester]; and 1H-pyrrole-2,4-dicarboxylic acid, 1-methyl-, bis[( 1,3-benzodioxol-5-ylmethyl)amide].

11. The compound according to claim 1, named 3-methoxy-thiophene-2,5-dicarboxylic acid bis benzylamide, or a pharmaceutically acceptable salt thereof.

12. The compound according to claim 6, named 4-({[5-(4-methoxy-benzylcarbamoyl)-2-methylamino-thiophene-3-carbonyl]-amino}-methyl)-2-methyl-benzoic acid, or a pharmaceutically acceptable salt thereof.

13. A pharmaceutical composition, comprising a compound according to claim 1 or 6, or a pharmaceutically acceptable salt thereof, in admixture with a pharmaceutically acceptable carrier, excipient, or diluent.

14. A method of treating a patient that has a disease mediated by MMP-13 enzymes and optionally from 0 to 15 additional MMP enzymes selected from MMP-1, MMP-2, MMP-3, MMP-7, MMP-8, MMP-9, MMP-10, MMP-11, MMP-12, MMP-14, MMP-15, MMP-16, MMP-17, MMP-18, and MMP-19, comprising administering to said patient a therapeutically effective amount of a compound according to claim 1, or a pharmaceutically acceptable salt thereof, wherein the disease is osteoarthritis.

* * * * *